United States Patent [19]

Beavo et al.

[11] Patent Number: 6,015,677
[45] Date of Patent: Jan. 18, 2000

[54] ASSAY METHODS USING DNA ENCODING MAMMALIAN PHOSPHODIESTERASES

[75] Inventors: Joseph A. Beavo; Kelley J. Bentley, both of Seattle, Wash.; Harry Charbonneau, W. Lafayette, Ind.; William K. Sonnenburg, Mountlake Terrace, Wash.

[73] Assignee: The Board of Regents of the University of Washington, Seattle, Wash.

[21] Appl. No.: 09/139,491

[22] Filed: Aug. 25, 1998

Related U.S. Application Data

[62] Division of application No. 08/455,525, May 31, 1995, Pat. No. 5,800,987, which is a division of application No. 08/297,494, Aug. 29, 1994, Pat. No. 5,580,771, which is a division of application No. 07/872,644, Apr. 20, 1992, Pat. No. 5,389,527, which is a continuation-in-part of application No. 07/688,356, Apr. 19, 1991, abandoned.

[51] Int. Cl.[7] ..................................................... C12Q 1/68
[52] U.S. Cl. ................................ 435/6; 435/29; 435/196; 435/254.21; 435/252.3
[58] Field of Search .................................. 435/6, 29, 196, 435/254.21, 252.3

[56] References Cited

U.S. PATENT DOCUMENTS 4,980,281  12/1990  Housey ..................................... 435/29

OTHER PUBLICATIONS

Ausubel, et al., eds., *Current Protocols in Molecular Biology,* 1: 1.7.1–1.7.2 and 9.2.1–9.2.3, John Wiley & Sons, New York (1989).

Beavo, J.A., "Multiple Isozymes of Cyclic Nucleotide Phosphodiesterase," *Advances in Second Messenger and Phosphoprotein Research,* 22: 1–38 (1988).

Beavo, J.A., "Multiple Phosphodiesterase Isoenzymes Background, Nomenclature and Implications", pp. 3–15; *Cyclic Nucleotide Phosphodiesterases; Structure, Regulation and Drug Action,* J. Beavo and Houslay, M.D., Eds.; John Wiley & Sond, Ltd., New York (1990).

Birnstiel, M.L., et al., "Transcription Termination and 3' Processing: The End Is in Sight!", *Cell,* 41: 349–359 (1985).

Bourne, H.R., et al., "Somatic Genetic Analysis of Cyclic AMP Action: Characterization of Unresponsive Mutants," *J. Cell. Physiol.,* 85: 611–620 (1985).

Bradford, M.M., "A Rapid and Sensitive Method for the Quantitation of Microgram Quantities of Protein Utilizing the Principle of Protein–Dye Binding," *Analytical Biochem.,* 72: 248–254 (1976).

Chen, C–N., et al., "Molecular Analysis of cDNA Clones and the Corresponding Genomic Coding Sequences of the Drosophila dunce[+] Gene, the Structural Gene for cAMP Phosphodiesterase," *Proc. Nat'l. Acad. Sci. (USA),* 83: 9313–9317 (1986).

Chomczynski, P., et al., "Single–Step Method of RNA Isolation by Acid Guanidinium Thiocyanate–Phenol–Chloroform Extraction," *Analytical Biochem.,* 162: 156–159 (1987).

Colicelli, J., et al., "Isolation and Characterization of a Mammalian Gene Encoding a High–Affinity cAMP Phosphodiesterase," *Proc. Nat'l. Acad. Sci. (USA),* 86: 3599–3603 (1989).

Davis, R.L., "Molecular Genetics of the Cyclic Nucleotide Phosphodiesterases", pp. 227–241 in *Cyclic Nucleotide Phosphodiesterases: Structure, Regulation and Drug Action,* J. Beavo and Houslay, M.D., Eds.; John Wiley & Sons, Ltd., New York (1990).

Davis, R.L., et al., "Cloning and Characterization of Mammalian Homologs of the Drosophila dunce[+] Gene," *Proc. Nat'l. Acad. Sci. (USA),* 86: 3604–3608 (1989).

Devereux, J., et al., "A Comprehensive Set of Sequence Analysis Programs for the VAX," *Nucleic Acids Res.,* 12: 387–395 (1984).

Erneux, C., et al., "A Mechanism in the Control of Intracelluar cAMP Level: The Activation of a Calmodulin–Sensitive Phosphodiesterase by a Rise of Intracellular Free Calcium," *Mol. Cell. Endocranial.,* 43: 123–134 (1985).

Faure, M., et al., "Disruption of *Dictyostelium discoideum* Morphogenesis by Overproduction of cAMP Phosphodiesterase," *Proc. Nat'l. Acad. Sci. (USA),* 85: 8076–8080 (1988).

Feinberg, A.P., et al., "A Technique for Radiolabeling DNA Restriction Endonuclease Fragments to High Specific Activity," *Analytical Biochem.,* 137: 266–267 (1984).

Greenberg, L.H., et al., "Enzymatic Regulation of the Concentration of Cyclic GMP in Mouse Brain," *Neuropharmacology,* 17: 737–745 (1978).

Hansen, R.S., et al., "Differential Recognition of Calmodulin–Enzyme Complexes by a Conformation–Specific Anti––Calmodulin Monoclonal Antibody," *J. Biol. Chem.,* 261: 14636–14645 (1986).

Hansen, R.S., et al., "Purification of Calmodulin–Stimulated Cyclic Nucleotide Phosphodiesterase by Monoclonal Antibody Affinity Chromatography," *Meth. Enzymol.,* 159: 543–557 (1988).

(List continued on next page.)

*Primary Examiner*—Rebecca E. Prouty
*Assistant Examiner*—Richard Hutson
*Attorney, Agent, or Firm*—Marshall, O'Toole, Gerstein, Murray & Borun

[57] ABSTRACT

The present invention relates to novel purified and isolated nucleotide sequences encoding mammalian $Ca^{2+}$/calmodulin stimulated phosphodiesterases (CaM-PDEs) and cyclic-GMP-stimulated phosphodiesterases (cGS-PDEs). Also provided are the corresponding recombinant expression products of said nucleotide sequences, immunological reagents specifically reactive therewith, and procedures for identifying compounds which modulate the enzymatic activity of such expression products.

4 Claims, 3 Drawing Sheets

OTHER PUBLICATIONS

Hansen, R.S., et al., "Purification of Two Calcium/Calmodulin–Dependent Forms of Cyclic Nucleotide Phosphodiesterase by Using Conformation–Specific Monoclonal antibody Chromatography," *Proc. Nat'l. Acad. Sci. (USA)*, 79: 2788–2792 (1982).

Hashimoto, Y., et al., "Regulation of $Ca^{2+}$/Caldmodulin–Dependent Cyclic Nucleotide Phosphodiesterase by the Autophosphorylated Form of $Ca^{2+}$/Calmodulin–Dependent Proteins Kinase II," *J. Biol. Chem.*, 264: 10884–10887 (1989).

Henikoff, S., "Unidirectional Digestion with Exonuclease III Creates Targeted Breakpoints for DNA Sequencing," *Gene*, 28: 351–359 (1984).

Kincaid, R.L., et al., "Differential Localization of Calmodulin–Dependent Enzymes in Rat Brain: Evidence for Selective Expression of Cyclic Nucleotide Phosphodiesterase in Specific Neurons," *Proc. Nat'l. Acad. Sci. (USA)*, 84: 1118–1122 (1987).

Kozak, M., " The Scanning Model for Translation: An Update," *J. Cell Biol.*, 108:229–241 (1989).

Krinks, M.H., et al., "Reversible and Irreversible Activation of Cyclic Nucleotide Phosphodiesterase: Separation of the Regulatory and Catalytic Domains by Limited Proteolysis," *Advances in Cyclic Nucleotide and Protein Phosphorylation Research*, 16: 31–47 (1984).

LaPorte, D.C., et al., "Cross–Linking of Iodine–125–Labeled, Calcium–Dependent Regulatory Protein to the $Ca^{2+}$–Sensitive Phosphodiesterase Purified from Bovine Heart," *Biochemistry*, 18: 2820–2825 (1979).

LeTrong, H., et al., "Amino Acid Sequence of the Cyclic GMP Stimulated Cyclic Nucleotide Phosphodiesterase from Bovine Heart," *Biochemistry*, 29: 10280–10288 (1990).

Livi, G.P., et al., "Cloning and Expression of cDNA for a Human Low–$K_m$ Rolipram–Sensitive Cyclic AMP Phosphodeisterase," *Mol. Cell. Biol.*, 10: 2678–2686 (1990).

Manganiello, V.C., et al. "Cyclic GMP–Stimulated Cyclic Nucleotide Phosphodiesterases", pp. 62–85 in *Cyclic Nucleotide Phosphodiesterases: Structure, Regulation and Drug Action*, Beavo, J. and Houslay, M.D., Eds.; John Wiley & Sons, Ltd., New York (1990).

Maniatis, et al., *Molecular Cloning: A Laboratory Manual*, pp. 324–328, Cold Spring Harbor Laboratory, Cold Spring Harbor, New York (1982).

Martins, T.J., et al., "Purification and Characterization of a Cyclic GMP–Stimulated Cyclic Nucleotide Phosphodiesterase from Bovine Tissues," *J. Biol. Chem.*, 257: 1973–1979 (1982).

Nikawa, J–I., et al., "Cloning and Characterization of the Low–Affinity Cyclic AMP Phosphodiesterase Gene of *Saccharomyces cerevisiae*," *Mol. Cell. Biol.*, 7: 3629–3636 (1987).

Nomenclature Committee of the International Union of Biochemistry (NCIUB), "Nomenclature for Incompletely Specified Bases in Nucleic Acid Sequences," *J. Biol. Chem.*, 261:13–17 (1986).

Novack, J.P., et al., "Sequence Comparison of the 63–, 61–, and 59–kDa Calmodulin–Dependent Cyclic Nucleotide Phosphodiesterases," *Biochemistry*, 30: 7940–7947 (1991).

Ovchinnikov, Y.A., et al., "Cyclic GMP Phosphodiesterase from Bovine Retina," *FEBS*, 223: 169–173 (1987).

Sanger, F., et al., "DNA Sequencing with Chain–Terminating Inhibitors," *Proc. Nat'l. Acad. Sci. (USA)*, 74: 5463–5467 (1977).

Sass, P., et al., "Cloning and Characterization of the High–Affinity cAMP Phosphodiesterase of *Saccharomyces cerevisiae*," *Proc. Nat'l. Acad. Sci. (USA)*, 83: 9303–9307 (1986).

Seed, B., "An LFA–3 cDNA encodes a Phospholipid–Linked Membrane Protein Homologous to Its Receptor CD2," *Nature*, 329: 840–842 (1987).

Sharma, R.K., et al., "Demonstration of Bovine Brain Calmodulin–Dependent Cyclic Nucleotide Phosphodiesterase Isozymes by Monoclonal Antibodies," *J. Biol. Chem.*, 259: 9248–9254 (1984).

Sharma, R.K., et al., "Differential Regulation of Bovine Brain Calmodulin–Dependent Cyclic Nucleotide Phosphodiesterase Isozymes by Cyclic AMP–Dependent Protein Kinase and Calmodulin–Dependent Phosphatase," *Proc. Nat'l. Acad. Sci. (USA)*, 82: 2603–2607 (1985).

Sharma, R.K., et al., "Purification and Characterization of Bovine Lung Calmodulin–Dependent Cyclic Nucleotide Phosphodiesterase," *J. Biol. Chem.*, 261: 14160–14166 (1986).

Short, M., et al., "ZAP: A Bacteriophage λ Expression Vector with in vivo Excision Properties," *Nucleic Acids Res.*, 16: 7583–7600 (1988).

Sonnenburg, W.K., et al., "Molecular Cloning of a Cyclic GMP–Stimulated Cyclic Nucleotide Phosphodiesterase cDNA," *J. Biol. Chem.*,266(26): 17655–17661 (1991).

Stroop, S.D., et al., "Direct Photolabeling of the cGMP––Stimulated Cyclic Nucleotide Phosphodiesterase," *J. Biol. Chem.*, 264: 13718–13725 (1989).

Swinnen, J.V., et al., "Molecular Cloning of Rat Homologous of the *Drosophila melanogaster* dunce cAMP Phosphodiesterase: Evidence for a Family of Genes," *Proc. Nat'l. Acad. Sci. (USA)*, 86: 5325–5329 (1989).

Tanner, L.I., et al., "Identification of the Phosphodiesterase Regulated by Muscarinic Cholinergic Receptors of the 1321N1 Human Astrocytoma Cells," *Mol. Pharmacol.*, 29: 455–460 (1986).

Thompson, W.J., et al., "Identification of Type II (Cyclic GMP–Stimulatable) Cyclic Nucleotide Phosphodiesterase (CNPDE) mRNA in Rat Pheochromocytoma Cells (PC12)," *FASEB J.*, 5(6): A1592 (Abstract No. 7092) (Mar. 1991).

Wang, J.H., et al., "Calmodulin–Stimulated Cyclic Nucleotide Phosphodiesterases", pp. 19–59; in *Cyclic Nucleotide Phosphodiesterases: Structure, Regulation and Drug Action*, Beavo, J. and Houslay, M.D., Eds.; John Wiley & Sons, Ltd., New York (1990).

Watson, et al., "An Alternative Procedure for the Synthesis of Double–Stranded cDNA for Cloning in Phage and Plasmid Vectors," pp. 79–88; in *DNA Cloning: A Practical Approach*, 1 (1985).

Wilson, R.B., et al., "SRA5 Encodes the Low–$K_M$ Cyclic AMP Phosphodiesterase of *Saccharomyces cerevisiae*," *Mol. Cell. Biol.*, 8: 505–510 (1988).

Charbonneau, H., et al., "Identification of a conserved domain among cyclic nucleotide phosphodiesterases from diverse species," *Proc. Nat'l. Acad. Sci. (USA)*, 83: 9308–9312 (1986).

Trong, H. L., et al., "Amino Acid Sequence of the Cyclic GMP Stimulated Cyclic Nucleotide Phosphodiesterase from Bovine Heart," *Biochemistry 1990*, 29: 10280–10288.

Epstein, P.M. et al., "Identification and characterization of a Ca2+ –calmodulin–sensitive cyclic nucleotide phosphodiesterase in a human lymphoblastoid cell line," *Biochem. J.*, 243:533–539 (1987).

Pennypacker, K.R. et al., "Expression of Calmodulin–Dependent Phosphodiesterase Calmodulin–Dependent Protein Phosphatase, and Other Calmodulin–Binding Proteins in Human SMS–KCNR Neuroblastoma Cells," *Journal of Neurochemistry*, 52(5):1438–1448 (1989).

```
59kDa:                ELFTRYDLINRFKIPVsCLIAFAEALEVGysKYKNPYHNLIHAADVTQTVHYIMLHTGIM
61kDa:                ELFTRYDLINRFKIPVSCLIAFAEALEVGYSKYKNPYHNLIHAADVTQTVHYIMLHTGIM
63kDa:                kIPTVFLMTFLDALETGYGK

59kDa:                HWLTELEILAMVFAAAIHDYEHTGTTNNFHIQtRSDVAILYNQRSVLENHHVSAAYR---
61kDa:                HWLTELEILAMVFAAAIHDYEHTGTTNNFHIQTRSDVAILYNQRSVLENHHVSAAYRLMQ
63kDa:                                                    kDETAILYNdRTVLEN

59kDa:                ---MNVLINLSKDDWRDLRNLVIEM-LST-------KNIRNSLQQPEGLDK-KTMSLI
61kDa:                EEEMNVLINLSKDDWRDLRNLVIEMVLSTDMSGHFQQIKNIRNSLQQPEGLDKAKTMSLI
63kDa:                                                          kTALQQLERIDK  kALSLL
```

FIGURE 1B

```
                                        370       380       390       400       410       420
                                         |         |         |         |         |         |
59kDa:                                  LHAADISHPAKSWKLHHRWTMALMEEFFLQGDKEAELGLPFSPLCDRKSTMVAQSQIGFI
61kDa:                                  LHAADISHPAKSWKLHHRWTMALMEEFFLQGDKEAELGLPFSPLCDRKSTMVAQSQIGFI
63kDa:                                  LHAADISHPTKQWSVHSRWTKALMEEFFRQGDK 430       440       450       460       470       480
                                         |         |         |         |         |         |
59kDa:                                  DFIVEPTFSLLTDSTEKIIIPLIEEDSKTKTPSYGASRRSNMKGTTNDGTYSPDYSLASV
61kDa:                                  DFIVEPTFSLLTDSTEKIIIPLIEEDSKTKTPSYGASRRSNMKGTTNDGTYSPDYSLASV
63kDa:

490       500       510       520       529
                                         |         |         |         |         |
59kDa:                                  DLKSFKNSLVDIIQQNKERWKELAAQGEPDPHKNSDLVNAEEKHAETHS
61kDa:                                  DLKSFKNSLVDIIQQNKERWKELAAQGEPDPHKNSDLVNAEEKHAETHS
63kDa:
```

FIGURE 1C

```
                            SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:1:

AARATGGGNA TGAARAARAA                                                  20

(2) INFORMATION FOR SEQ ID NO:2:

(i) SEQUENCE CHARACTERISTICS:
         (A) LENGTH: 8 amino acids
         (B) TYPE: amino acid
         (D) TOPOLOGY: linear (ii) MOLECULE TYPE: peptide (xi) SEQUENCE DESCRIPTION: SEQ ID NO:2:

Lys Met Gly Met Met Lys Lys Lys
1               5

(2) INFORMATION FOR SEQ ID NO:3:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO:3:

ACRTTCATYT CYTCYTCYTG CAT                                              23

(2) INFORMATION FOR SEQ ID NO:4:

(i) SEQUENCE CHARACTERISTICS:
         (A) LENGTH: 8 amino acids
         (B) TYPE: amino acid
         (D) TOPOLOGY: linear (ii) MOLECULE TYPE: peptide
```

(xi) SEQUENCE DESCRIPTION: SEQ ID NO:4:

```
Met Gln Glu Glu Glu Met Asn Val
1               5
```

(2) INFORMATION FOR SEQ ID NO:5:

(i) SEQUENCE CHARACTERISTICS:
        (A) LENGTH: 2291 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 100..1689

(xi) SEQUENCE DESCRIPTION: SEQ ID NO:5:

```
GGCTCAGAAA CTGTAGGAAT TCTGATGTGC TTCGGTGCAT GGAACAGTAA CAGATGAGCT         60

GCTTTGGGGA GAGCTGGAAC GCTCAGTCGG AGTATCATC ATG GGG TCT ACT GCT          114
                                           Met Gly Ser Thr Ala
                                             1               5

ACA GAA ACT GAA GAA CTG GAA AAC ACT ACT TTT AAG TAT CTC ATT GGA         162
Thr Glu Thr Glu Glu Leu Glu Asn Thr Thr Phe Lys Tyr Leu Ile Gly
                10                  15                  20

GAA CAG ACT GAA AAA ATG TGG CAA CGC CTG AAA GGA ATA CTA AGA TGC         210
Glu Gln Thr Glu Lys Met Trp Gln Arg Leu Lys Gly Ile Leu Arg Cys
        25                  30                  35

TTA GTG AAG CAG CTG GAA AAA GGT GAT GTT AAC GTC ATC GAC TTA AAG         258
Leu Val Lys Gln Leu Glu Lys Gly Asp Val Asn Val Ile Asp Leu Lys
    40                  45                  50

AAG AAT ATT GAA TAT GCA GCA TCT GTG TTG GAA GCA GTT TAT ATT GAT         306
Lys Asn Ile Glu Tyr Ala Ala Ser Val Leu Glu Ala Val Tyr Ile Asp
55                  60                  65

GAA ACA AGG AGA CTG CTG GAC ACC GAT GAT GAG CTC AGT GAC ATT CAG         354
Glu Thr Arg Arg Leu Leu Asp Thr Asp Asp Glu Leu Ser Asp Ile Gln
70                  75                  80                  85

TCG GAT TCC GTC CCA TCA GAA GTC CGG GAC TGG TTG GCT TCT ACC TTT         402
Ser Asp Ser Val Pro Ser Glu Val Arg Asp Trp Leu Ala Ser Thr Phe
            90                  95                 100

ACA CGG AAA ATG GGG ATG ATG AAA AAG AAA TCT GAG GAA AAA CCA AGA         450
Thr Arg Lys Met Gly Met Met Lys Lys Lys Ser Glu Glu Lys Pro Arg
       105                 110                 115

TTT CGG AGC ATT GTG CAT GTT GTT CAA GCT GGA ATT TTT GTG GAA AGA         498
Phe Arg Ser Ile Val His Val Val Gln Ala Gly Ile Phe Val Glu Arg
        120                 125                 130

ATG TAC AGA AAG TCC TAT CAC ATG GTT GGC TTG GCA TAT CCA GAG GCT         546
Met Tyr Arg Lys Ser Tyr His Met Val Gly Leu Ala Tyr Pro Glu Ala
   135                 140                 145

GTC ATA GTA ACA TTA AAG GAT GTT GAT AAA TGG TCT TTT GAT GTA TTT         594
Val Ile Val Thr Leu Lys Asp Val Asp Lys Trp Ser Phe Asp Val Phe
150                 155                 160                 165

GCC TTG AAT GAA GCA AGT GGA GAA CAC AGT CTG AAG TTT ATG ATT TAT         642
Ala Leu Asn Glu Ala Ser Gly Glu His Ser Leu Lys Phe Met Ile Tyr
            170                 175                 180

GAA CTA TTC ACC AGA TAT GAT CTT ATC AAC CGT TTC AAG ATT CCT GTT         690
Glu Leu Phe Thr Arg Tyr Asp Leu Ile Asn Arg Phe Lys Ile Pro Val
        185                 190                 195

TCT TGC CTA ATT GCC TTT GCA GAA GCT CTA GAA GTT GGT TAC AGC AAG         738
Ser Cys Leu Ile Ala Phe Ala Glu Ala Leu Glu Val Gly Tyr Ser Lys
        200                 205                 210
```

```
TAC AAA AAT CCA TAC CAC AAT TTG ATT CAT GCA GCT GAT GTC ACT CAA      786
Tyr Lys Asn Pro Tyr His Asn Leu Ile His Ala Ala Asp Val Thr Gln
        215                 220                 225

ACT GTG CAT TAC ATA ATG CTT CAT ACA GGT ATC ATG CAC TGG CTC ACT      834
Thr Val His Tyr Ile Met Leu His Thr Gly Ile Met His Trp Leu Thr
230                 235                 240                 245

GAA CTG GAA ATT TTA GCA ATG GTC TTT GCC GCT GCC ATT CAT GAC TAT      882
Glu Leu Glu Ile Leu Ala Met Val Phe Ala Ala Ala Ile His Asp Tyr
                    250                 255                 260

GAG CAT ACA GGG ACT ACA AAC AAT TTT CAC ATT CAG ACA AGG TCA GAT      930
Glu His Thr Gly Thr Thr Asn Asn Phe His Ile Gln Thr Arg Ser Asp
            265                 270                 275

GTT GCC ATT TTG TAT AAT GAT CGC TCT GTC CTT GAA AAT CAT CAT GTG      978
Val Ala Ile Leu Tyr Asn Asp Arg Ser Val Leu Glu Asn His His Val
        280                 285                 290

AGT GCA GCT TAT CGC CTT ATG CAA GAA GAA GAA ATG AAT GTC CTG ATA     1026
Ser Ala Ala Tyr Arg Leu Met Gln Glu Glu Glu Met Asn Val Leu Ile
    295                 300                 305

AAT TTA TCC AAA GAT GAC TGG AGG GAT CTT CGG AAC CTA GTG ATT GAA     1074
Asn Leu Ser Lys Asp Asp Trp Arg Asp Leu Arg Asn Leu Val Ile Glu
310                 315                 320                 325

ATG GTG TTG TCT ACA GAC ATG TCG GGT CAC TTC CAG CAA ATT AAA AAT     1122
Met Val Leu Ser Thr Asp Met Ser Gly His Phe Gln Gln Ile Lys Asn
                    330                 335                 340

ATA AGA AAT AGT TTG CAG CAA CCT GAA GGG CTT GAC AAA GCC AAA ACC     1170
Ile Arg Asn Ser Leu Gln Gln Pro Glu Gly Leu Asp Lys Ala Lys Thr
            345                 350                 355

ATG TCC CTG ATT CTC CAT GCA GCA GAC ATC AGT CAC CCA GCC AAA TCC     1218
Met Ser Leu Ile Leu His Ala Ala Asp Ile Ser His Pro Ala Lys Ser
        360                 365                 370

TGG AAG CTG CAC CAC CGA TGG ACC ATG GCC CTA ATG GAG GAG TTT TTC     1266
Trp Lys Leu His His Arg Trp Thr Met Ala Leu Met Glu Glu Phe Phe
375                 380                 385

CTA CAG GGA GAT AAA GAA GCT GAA TTA GGG CTT CCA TTT TCC CCG CTT     1314
Leu Gln Gly Asp Lys Glu Ala Glu Leu Gly Leu Pro Phe Ser Pro Leu
390                 395                 400                 405

TGC GAT CGG AAG TCA ACG ATG GTG GCC CAG TCC CAA ATA GGT TTC ATT     1362
Cys Asp Arg Lys Ser Thr Met Val Ala Gln Ser Gln Ile Gly Phe Ile
                    410                 415                 420

GAT TTC ATA GTA GAA CCA ACA TTT TCT CTT CTG ACA GAC TCA ACA GAG     1410
Asp Phe Ile Val Glu Pro Thr Phe Ser Leu Leu Thr Asp Ser Thr Glu
            425                 430                 435

AAA ATT ATT ATT CCT CTT ATA GAG GAA GAC TCG AAA ACC AAA ACT CCT     1458
Lys Ile Ile Ile Pro Leu Ile Glu Glu Asp Ser Lys Thr Lys Thr Pro
        440                 445                 450

TCC TAT GGA GCA AGC AGA CGA TCA AAT ATG AAA GGC ACC ACC AAT GAT     1506
Ser Tyr Gly Ala Ser Arg Arg Ser Asn Met Lys Gly Thr Thr Asn Asp
    455                 460                 465

GGA ACC TAC TCC CCC GAC TAC TCC CTT GCC AGC GTG GAC CTG AAG AGC     1554
Gly Thr Tyr Ser Pro Asp Tyr Ser Leu Ala Ser Val Asp Leu Lys Ser
470                 475                 480                 485

TTC AAA AAC AGC CTG GTG GAC ATC ATC CAG CAG AAC AAA GAG AGG TGG     1602
Phe Lys Asn Ser Leu Val Asp Ile Ile Gln Gln Asn Lys Glu Arg Trp
                    490                 495                 500

AAA GAG TTA GCT GCT CAA GGT GAA CCT GAT CCC CAT AAG AAC TCA GAT     1650
Lys Glu Leu Ala Ala Gln Gly Glu Pro Asp Pro His Lys Asn Ser Asp
            505                 510                 515

CTA GTA AAT GCT GAA GAA AAA CAT GCT GAA ACA CAT TCA TAGGTCTGAA      1699
Leu Val Asn Ala Glu Glu Lys His Ala Glu Thr His Ser
        520                 525                 530
```

```
ACACCTGAAA GACGTCTTTC ATTCTAAGGA TGGGAGGAAA CAAATTCACA AGAAATCATG    1759

AAGACATATA AAAGCTACAT ATGCATAAAA AACTCTGAAT TCAGGTCCCC ATGGCTGTCA    1819

CAAATGAATG AACAGAACTC CCAACCCCGC CTTTTTTTAA TATAATGAAA GTGCCTTAGC    1879

ATGGTTGCAG CTGTCACCAC TACAGTGTTT TACAGACGGT TTCTACTGAG CATCACAATA    1939

AAGAGAATCT TGCATTACAA AAAAAGAAA AAAATGTGGC TCGCTTTTAA GATGAAGCAT    1999

TTCCCAGTAT TTCTGAGTCA GTTGTAAGAT TCTTTAATCG ATACTAATAG TTTCACTAAT    2059

AGCCACTGTC AGTGTCACGC ACTGTGATGA AATCTTATAC TTAGTCCTTC AACAGTTCCA    2119

GAGTTGTGAC TGTGCTTAAT AGTTTGCATA TGAATTCTGG ATAGAAATCA AATCACAAAC    2179

TGCATAGAAA TTTTAAAAAC CAGCTCCATA TTAAATTTTT TTAAGATATT GTCTTGTATT    2239

GAAACTCCAA TACTTTGGCC ACCTGATGCA AAGAGCTGAC TCATTTGAAA CC            2291
```

(2) INFORMATION FOR SEQ ID NO:6:

(i) SEQUENCE CHARACTERISTICS:
        (A) LENGTH: 530 amino acids
        (B) TYPE: amino acid
        (D) TOPOLOGY: linear (ii) MOLECULE TYPE: protein (xi) SEQUENCE DESCRIPTION: SEQ ID NO:6:

```
Met Gly Ser Thr Ala Thr Glu Thr Glu Glu Leu Glu Asn Thr Thr Phe
  1               5                  10                  15

Lys Tyr Leu Ile Gly Glu Gln Thr Glu Lys Met Trp Gln Arg Leu Lys
                 20                  25                  30

Gly Ile Leu Arg Cys Leu Val Lys Gln Leu Glu Lys Gly Asp Val Asn
             35                  40                  45

Val Ile Asp Leu Lys Lys Asn Ile Glu Tyr Ala Ala Ser Val Leu Glu
         50                  55                  60

Ala Val Tyr Ile Asp Glu Thr Arg Arg Leu Leu Asp Thr Asp Asp Glu
 65                  70                  75                  80

Leu Ser Asp Ile Gln Ser Asp Ser Val Pro Ser Glu Val Arg Asp Trp
                 85                  90                  95

Leu Ala Ser Thr Phe Thr Arg Lys Met Gly Met Met Lys Lys Lys Ser
                100                 105                 110

Glu Glu Lys Pro Arg Phe Arg Ser Ile Val His Val Gln Ala Gly
                115                 120                 125

Ile Phe Val Glu Arg Met Tyr Arg Lys Ser Tyr His Met Val Gly Leu
            130                 135                 140

Ala Tyr Pro Glu Ala Val Ile Val Thr Leu Lys Asp Val Asp Lys Trp
145                 150                 155                 160

Ser Phe Asp Val Phe Ala Leu Asn Glu Ala Ser Gly Glu His Ser Leu
                165                 170                 175

Lys Phe Met Ile Tyr Glu Leu Phe Thr Arg Tyr Asp Leu Ile Asn Arg
            180                 185                 190

Phe Lys Ile Pro Val Ser Cys Leu Ile Ala Phe Ala Glu Ala Leu Glu
        195                 200                 205

Val Gly Tyr Ser Lys Tyr Lys Asn Pro Tyr His Asn Leu Ile His Ala
    210                 215                 220

Ala Asp Val Thr Gln Thr Val His Tyr Ile Met Leu His Thr Gly Ile
225                 230                 235                 240

Met His Trp Leu Thr Glu Leu Glu Ile Leu Ala Met Val Phe Ala Ala
                245                 250                 255
```

```
Ala Ile His Asp Tyr Glu His Thr Gly Thr Thr Asn Asn Phe His Ile
        260                 265                 270

Gln Thr Arg Ser Asp Val Ala Ile Leu Tyr Asn Asp Arg Ser Val Leu
        275                 280                 285

Glu Asn His His Val Ser Ala Ala Tyr Arg Leu Met Gln Glu Glu Glu
        290                 295                 300

Met Asn Val Leu Ile Asn Leu Ser Lys Asp Asp Trp Arg Asp Leu Arg
305                 310                 315                 320

Asn Leu Val Ile Glu Met Val Leu Ser Thr Asp Met Ser Gly His Phe
                325                 330                 335

Gln Gln Ile Lys Asn Ile Arg Asn Ser Leu Gln Gln Pro Glu Gly Leu
        340                 345                 350

Asp Lys Ala Lys Thr Met Ser Leu Ile Leu His Ala Ala Asp Ile Ser
        355                 360                 365

His Pro Ala Lys Ser Trp Lys Leu His His Arg Trp Thr Met Ala Leu
        370                 375                 380

Met Glu Glu Phe Phe Leu Gln Gly Asp Lys Glu Ala Glu Leu Gly Leu
385                 390                 395                 400

Pro Phe Ser Pro Leu Cys Asp Arg Lys Ser Thr Met Val Ala Gln Ser
        405                 410                 415

Gln Ile Gly Phe Ile Asp Phe Ile Val Glu Pro Thr Phe Ser Leu Leu
        420                 425                 430

Thr Asp Ser Thr Glu Lys Ile Ile Pro Leu Ile Glu Glu Asp Ser
        435                 440                 445

Lys Thr Lys Thr Pro Ser Tyr Gly Ala Ser Arg Arg Ser Asn Met Lys
        450                 455                 460

Gly Thr Thr Asn Asp Gly Thr Tyr Ser Pro Asp Tyr Ser Leu Ala Ser
465                 470                 475                 480

Val Asp Leu Lys Ser Phe Lys Asn Ser Leu Val Asp Ile Ile Gln Gln
                485                 490                 495

Asn Lys Glu Arg Trp Lys Glu Leu Ala Ala Gln Gly Glu Pro Asp Pro
        500                 505                 510

His Lys Asn Ser Asp Leu Val Asn Ala Glu Glu Lys His Ala Glu Thr
        515                 520                 525

His Ser
    530

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:7:

Met Asp Asp His Val Thr Ile
1               5

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA
```

(xi) SEQUENCE DESCRIPTION: SEQ ID NO:8:

ATGAGRAGRC AYGTHACNAT                          20

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:9:

Leu Arg Cys Leu Val Lys Gln
1               5

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:10:

CTGCTTCACT AAGCATCTTA G                        21

(2) INFORMATION FOR SEQ ID NO:11:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ATGAGAAGGC ACGTAACGAT CAGGAGGAAA CATCTCCAAA GACCCATCTT TAGACTAAGA     60

TGCTTAGTGA AGCAG                               75

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

ATGGAYGAYC ACGTAACGAT C                        21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iv) ANTI-SENSE: YES (xi) SEQUENCE DESCRIPTION: SEQ ID NO:13:

AAGTATCTCA TTGGAGAACA G                                              21

(2) INFORMATION FOR SEQ ID NO:14:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

ATGGATGATC ACGTAACGAT CAGGAGGAAA CATCTCCAAA GACCCATCTT TAGA           54

(2) INFORMATION FOR SEQ ID NO:15:

(i) SEQUENCE CHARACTERISTICS:
            (A) LENGTH: 18 amino acids
            (B) TYPE: amino acid
            (D) TOPOLOGY: linear (ii) MOLECULE TYPE: protein (xi) SEQUENCE DESCRIPTION: SEQ ID NO:15:

Met Asp Asp His Val Thr Ile Arg Arg Lys His Leu Gln Arg Pro Ile
1               5                   10                  15

Phe Arg (2) INFORMATION FOR SEQ ID NO:16:

(i) SEQUENCE CHARACTERISTICS:
            (A) LENGTH: 2656 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 136..1677

(xi) SEQUENCE DESCRIPTION: SEQ ID NO:16:

TTGCTGTCGA GAGAAAGAGG AAACTACTTT TGCCTTCTGG GCTCCTTGCA GGACAATAGA    60

TCAGGATAAG CTTCCACATT CTCTCCCTGG ATTTCTGGAG TGGTTTCCAG GAACAAGCTA   120

AACTTTCACC TTTAA ATG GAT GAC CAT GTC ACA ATC AGG AGG AAA CAT CTC    171
              Met Asp Asp His Val Thr Ile Arg Arg Lys His Leu
              1               5                   10

CAA AGA CCC ATC TTT AGA CTA AGA TGC TTA GTG AAG CAG CTG GAA AAA     219
Gln Arg Pro Ile Phe Arg Leu Arg Cys Leu Val Lys Gln Leu Glu Lys
        15                  20                  25

GGT GAT GTT AAC GTC ATC GAC TTA AAG AAG AAT ATT GAA TAT GCA GCA     267
Gly Asp Val Asn Val Ile Asp Leu Lys Lys Asn Ile Glu Tyr Ala Ala
    30                  35                  40

TCT GTG TTG GAA GCA GTT TAT ATT GAT GAA ACA AGG AGA CTG CTG GAC     315
Ser Val Leu Glu Ala Val Tyr Ile Asp Glu Thr Arg Arg Leu Leu Asp
45                  50                  55                  60

ACC GAT GAT GAG CTC AGT GAC ATT CAG TCG GAT TCC GTC CCA TCA GAA     363
Thr Asp Asp Glu Leu Ser Asp Ile Gln Ser Asp Ser Val Pro Ser Glu
            65                  70                  75

GTC CGG GAC TGG TTG GCT TCT ACC TTT ACA CGG AAA ATG GGG ATG ATG     411

-continued

| | | | | | | | | | | | | |
|---|---|---|---|---|---|---|---|---|---|---|---|---|
| Val | Arg | Asp | Trp | Leu | Ala | Ser | Thr | Phe | Thr | Arg | Lys | Met | Gly | Met | Met |
| | | | 80 | | | | | 85 | | | | | 90 | | |

```
AAA AAG AAA TCT GAG GAA AAA CCA AGA TTT CGG AGC ATT GTG CAT GTT      459
Lys Lys Lys Ser Glu Glu Lys Pro Arg Phe Arg Ser Ile Val His Val
            95                  100                 105

GTT CAA GCT GGA ATT TTT GTG GAA AGA ATG TAC AGA AAG TCC TAT CAC      507
Val Gln Ala Gly Ile Phe Val Glu Arg Met Tyr Arg Lys Ser Tyr His
        110                 115                 120

ATG GTT GGC TTG GCA TAT CCA GAG GCT GTC ATA GTA ACA TTA AAG GAT      555
Met Val Gly Leu Ala Tyr Pro Glu Ala Val Ile Val Thr Leu Lys Asp
125                 130                 135                 140

GTT GAT AAA TGG TCT TTT GAT GTA TTT GCC TTG AAT GAA GCA AGT GGA      603
Val Asp Lys Trp Ser Phe Asp Val Phe Ala Leu Asn Glu Ala Ser Gly
                145                 150                 155

GAA CAC AGT CTG AAG TTT ATG ATT TAT GAA CTA TTC ACC AGA TAT GAT      651
Glu His Ser Leu Lys Phe Met Ile Tyr Glu Leu Phe Thr Arg Tyr Asp
            160                 165                 170

CTT ATC AAC CGT TTC AAG ATT CCT GTT TCT TGC CTA ATT GCC TTT GCA      699
Leu Ile Asn Arg Phe Lys Ile Pro Val Ser Cys Leu Ile Ala Phe Ala
                175                 180                 185

GAA GCT CTA GAA GTT GGT TAC AGC AAG TAC AAA AAT CCA TAC CAC AAT      747
Glu Ala Leu Glu Val Gly Tyr Ser Lys Tyr Lys Asn Pro Tyr His Asn
            190                 195                 200

TTG ATT CAT GCA GCT GAT GTC ACT CAA ACT GTG CAT TAC ATA ATG CTT      795
Leu Ile His Ala Ala Asp Val Thr Gln Thr Val His Tyr Ile Met Leu
205                 210                 215                 220

CAT ACA GGT ATC ATG CAC TGG CTC ACT GAA CTG GAA ATT TTA GCA ATG      843
His Thr Gly Ile Met His Trp Leu Thr Glu Leu Glu Ile Leu Ala Met
                225                 230                 235

GTC TTT GCC GCT GCC ATT CAT GAC TAT GAG CAT ACA GGG ACT ACA AAC      891
Val Phe Ala Ala Ala Ile His Asp Tyr Glu His Thr Gly Thr Thr Asn
            240                 245                 250

AAT TTT CAC ATT CAG ACA AGG TCA GAT GTT GCC ATT TTG TAT AAT GAT      939
Asn Phe His Ile Gln Thr Arg Ser Asp Val Ala Ile Leu Tyr Asn Asp
                255                 260                 265

CGC TCT GTC CTT GAA AAT CAT CAT GTG AGT GCA GCT TAT CGC CTT ATG      987
Arg Ser Val Leu Glu Asn His His Val Ser Ala Ala Tyr Arg Leu Met
270                 275                 280

CAA GAA GAA GAA ATG AAT GTC CTG ATA AAT TTA TCC AAA GAT GAC TGG     1035
Gln Glu Glu Glu Met Asn Val Leu Ile Asn Leu Ser Lys Asp Asp Trp
285                 290                 295                 300

AGG GAT CTT CGG AAC CTA GTG ATT GAA ATG GTG TTG TCT ACA GAC ATG     1083
Arg Asp Leu Arg Asn Leu Val Ile Glu Met Val Leu Ser Thr Asp Met
                305                 310                 315

TCG GGT CAC TTC CAG CAA ATT AAA AAT ATA AGA AAT AGT TTG CAG CAA     1131
Ser Gly His Phe Gln Gln Ile Lys Asn Ile Arg Asn Ser Leu Gln Gln
            320                 325                 330

CCT GAA GGG CTT GAC AAA GCC AAA ACC ATG TCC CTG ATT CTC CAT GCA     1179
Pro Glu Gly Leu Asp Lys Ala Lys Thr Met Ser Leu Ile Leu His Ala
        335                 340                 345

GCA GAC ATC AGT CAC CCA GCC AAA TCC TGG AAG CTG CAC CAC CGA TGG     1227
Ala Asp Ile Ser His Pro Ala Lys Ser Trp Lys Leu His His Arg Trp
350                 355                 360

ACC ATG GCC CTA ATG GAG GAG TTT TTC CTA CAG GGA GAT AAA GAA GCT     1275
Thr Met Ala Leu Met Glu Glu Phe Phe Leu Gln Gly Asp Lys Glu Ala
365                 370                 375                 380

GAA TTA GGG CTT CCA TTT TCC CCG CTT TGC GAT CGG AAG TCA ACG ATG     1323
Glu Leu Gly Leu Pro Phe Ser Pro Leu Cys Asp Arg Lys Ser Thr Met
            385                 390                 395

GTG GCC CAG TCC CAA ATA GGT TTC ATT GAT TTC ATA GTA GAA CCA ACA     1371
```

-continued

```
Val Ala Gln Ser Gln Ile Gly Phe Ile Asp Phe Ile Val Glu Pro Thr
            400                 405                 410

TTT TCT CTT CTG ACA GAC TCA ACA GAG AAA ATT ATT ATT CCT CTT ATA         1419
Phe Ser Leu Leu Thr Asp Ser Thr Glu Lys Ile Ile Ile Pro Leu Ile
        415                 420                 425

GAG GAA GAC TCG AAA ACC AAA ACT CCT TCC TAT GGA GCA AGC AGA CGA         1467
Glu Glu Asp Ser Lys Thr Lys Thr Pro Ser Tyr Gly Ala Ser Arg Arg
    430                 435                 440

TCA AAT ATG AAA GGC ACC ACC AAT GAT GGA ACC TAC TCC CCC GAC TAC         1515
Ser Asn Met Lys Gly Thr Thr Asn Asp Gly Thr Tyr Ser Pro Asp Tyr
445                 450                 455                 460

TCC CTT GCC AGC GTG GAC CTG AAG AGC TTC AAA AAC AGC CTG GTG GAC         1563
Ser Leu Ala Ser Val Asp Leu Lys Ser Phe Lys Asn Ser Leu Val Asp
                465                 470                 475

ATC ATC CAG CAG AAC AAA GAG AGG TGG AAA GAG TTA GCT GCT CAA GGT         1611
Ile Ile Gln Gln Asn Lys Glu Arg Trp Lys Glu Leu Ala Ala Gln Gly
            480                 485                 490

GAA CCT GAT CCC CAT AAG AAC TCA GAT CTA GTA AAT GCT GAA GAA AAA         1659
Glu Pro Asp Pro His Lys Asn Ser Asp Leu Val Asn Ala Glu Glu Lys
        495                 500                 505

CAT GCT GAA ACA CAT TCA TAGGTCTGAA ACACCTGAAA GACGTCTTTC                1707
His Ala Glu Thr His Ser
    510

ATTCTAAGGA TGGGAGAGTG CTGTAACTAC AAAACTTTCA AGCTTCTAAG TAAAAGGAAA       1767

GCAAAAACAA AATTACAGAA AAATATTTTT GCAGCTCTGA GGCTATTTAG ATTGTCCTTG       1827

TTGTTTTAAA TACATGGGAA CCAAGTGAGA GAGGGGCTG CTCAGAAGTT GTAGTCGAAG        1887

TCCTAAGACA ACAATGAAGC ATCAGAGCCC TGACTCTGTG ACCTGATGAA CTCTTCGTTG       1947

TAACTCTCAA GCTGGGAAAC CACAGCGAAT CCTGTTCCTG AAAGCAGTGA ACCAGCCTGC       2007

ATCCACCACT GTTATTGCAA AGCACGAAAG CATCACCCAC GTGGGGGTCA TCACAATGCA       2067

AGTCACGCAA GACCTATGAC CAAGATGACA AGAACCTCCA GCCCTTGTTG GAGACAGACA      2127

CTAGAACTGA GAGTGGGATT TGCCTTCTGG GGTGTTAATC CCATCAGGAT GTAACAAAAT      2187

ATATTACAGG TCAAGGGATA AGGGACAAGA AGTGTGTGTC TGTGTGTGTG TGTGTGTATG      2247

TGCGCGCACT CAAAAATGTC TGTGAAAATG AAGCCCACA CTCTTCTGCA CAGAGAGCAT       2307

TATTTGATGT GATTTATAAT TTTACTACAA ACAAACGAAC TGCAGCCATT GGAGACTGCT      2367

TCCTTGTCAT GTTTTGCCTG AGCATGTGCA GAGCCTTGCC TTTGTTCCAA ATTGAAGAAC      2427

TACCTTTATT TGTTATTAGC TGCCAAGAAA GGTCAAGCCC AAGTAGGTGT TGTCATTTTC      2487

ACCGTACAAA CTCTTCAATG ATTGTTAGAC TAAAGGAATT TGTTTTTGTG AAAGGTAGAA      2547

ATTAGATGGA AAAGATCAAG AGTAGTCATC AATTAAAGAA GAAAGTGAAG GTGGATATGT      2607

CCATCCTAAT GAGTTTTCTG TTGCACCTGC TTCTTCCCTG CGACAGCAA                  2656
```

(2) INFORMATION FOR SEQ ID NO:17:

(i) SEQUENCE CHARACTERISTICS:
        (A) LENGTH: 514 amino acids
        (B) TYPE: amino acid
        (D) TOPOLOGY: linear (ii) MOLECULE TYPE: protein (xi) SEQUENCE DESCRIPTION: SEQ ID NO:17:

```
Met Asp Asp His Val Thr Ile Arg Arg Lys His Leu Gln Arg Pro Ile
 1               5                  10                  15

Phe Arg Leu Arg Cys Leu Val Lys Gln Leu Glu Lys Gly Asp Val Asn
            20                  25                  30
```

-continued

```
Val Ile Asp Leu Lys Lys Asn Ile Glu Tyr Ala Ala Ser Val Leu Glu
         35                  40                  45

Ala Val Tyr Ile Asp Glu Thr Arg Arg Leu Leu Asp Thr Asp Asp Glu
 50                  55                  60

Leu Ser Asp Ile Gln Ser Asp Ser Val Pro Ser Glu Val Arg Asp Trp
 65                  70                  75                  80

Leu Ala Ser Thr Phe Thr Arg Lys Met Gly Met Met Lys Lys Lys Ser
                 85                  90                  95

Glu Glu Lys Pro Arg Phe Arg Ser Ile Val His Val Gln Ala Gly
                100                 105                 110

Ile Phe Val Glu Arg Met Tyr Arg Lys Ser Tyr His Met Val Gly Leu
                115                 120                 125

Ala Tyr Pro Glu Ala Val Ile Val Thr Leu Lys Asp Val Asp Lys Trp
                130                 135                 140

Ser Phe Asp Val Phe Ala Leu Asn Glu Ala Ser Gly Glu His Ser Leu
145                 150                 155                 160

Lys Phe Met Ile Tyr Glu Leu Phe Thr Arg Tyr Asp Leu Ile Asn Arg
                165                 170                 175

Phe Lys Ile Pro Val Ser Cys Leu Ile Ala Phe Ala Glu Ala Leu Glu
                180                 185                 190

Val Gly Tyr Ser Lys Tyr Lys Asn Pro Tyr His Asn Leu Ile His Ala
                195                 200                 205

Ala Asp Val Thr Gln Thr Val His Tyr Ile Met Leu His Thr Gly Ile
210                 215                 220

Met His Trp Leu Thr Glu Leu Glu Ile Leu Ala Met Val Phe Ala Ala
225                 230                 235                 240

Ala Ile His Asp Tyr Glu His Thr Gly Thr Thr Asn Asn Phe His Ile
                245                 250                 255

Gln Thr Arg Ser Asp Val Ala Ile Leu Tyr Asn Asp Arg Ser Val Leu
                260                 265                 270

Glu Asn His His Val Ser Ala Ala Tyr Arg Leu Met Gln Glu Glu Glu
                275                 280                 285

Met Asn Val Leu Ile Asn Leu Ser Lys Asp Asp Trp Arg Asp Leu Arg
290                 295                 300

Asn Leu Val Ile Glu Met Val Leu Ser Thr Asp Met Ser Gly His Phe
305                 310                 315                 320

Gln Gln Ile Lys Asn Ile Arg Asn Ser Leu Gln Gln Pro Glu Gly Leu
                325                 330                 335

Asp Lys Ala Lys Thr Met Ser Leu Ile Leu His Ala Ala Asp Ile Ser
                340                 345                 350

His Pro Ala Lys Ser Trp Lys Leu His His Arg Trp Thr Met Ala Leu
                355                 360                 365

Met Glu Glu Phe Phe Leu Gln Gly Asp Lys Glu Ala Glu Leu Gly Leu
370                 375                 380

Pro Phe Ser Pro Leu Cys Asp Arg Lys Ser Thr Met Val Ala Gln Ser
385                 390                 395                 400

Gln Ile Gly Phe Ile Asp Phe Ile Val Glu Pro Thr Phe Ser Leu Leu
                405                 410                 415

Thr Asp Ser Thr Glu Lys Ile Ile Pro Leu Ile Glu Glu Asp Ser
                420                 425                 430

Lys Thr Lys Thr Pro Ser Tyr Gly Ala Ser Arg Arg Ser Asn Met Lys
                435                 440                 445

Gly Thr Thr Asn Asp Gly Thr Tyr Ser Pro Asp Tyr Ser Leu Ala Ser
```

```
                450           455           460
Val Asp Leu Lys Ser Phe Lys Asn Ser Leu Val Asp Ile Ile Gln Gln
465                 470                 475                 480

Asn Lys Glu Arg Trp Lys Glu Leu Ala Ala Gln Gly Glu Pro Asp Pro
                485                 490                 495

His Lys Asn Ser Asp Leu Val Asn Ala Glu Glu Lys His Ala Glu Thr
                500                 505                 510

His Ser
```

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

ATHCAYGAYT AYGARCAYAC NGG                                          23

(2) INFORMATION FOR SEQ ID NO:19:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:19:

```
Ile His Asp Tyr Glu His Thr Gly
1               5
```

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TCYTTRTCNC CYTGNCGRAA RAAYTCYTCC AT                          32

(2) INFORMATION FOR SEQ ID NO:21:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (xi) SEQUENCE DESCRIPTION: SEQ ID NO:21:

```
Met Glu Glu Phe Phe Arg Gln Gly Asp Lys Glu
1               5                   10
```

(2) INFORMATION FOR SEQ ID NO:22:

(i) SEQUENCE CHARACTERISTICS:
        (A) LENGTH: 412 base pairs
        (B) TYPE: nucleic acid
        (C) STRANDEDNESS: single (D) TOPOLOGY: linear (ii) MOLECULE TYPE: cDNA (ix) FEATURE:
    (A) NAME/KEY: CDS
    (B) LOCATION: 1..412

(xi) SEQUENCE DESCRIPTION: SEQ ID NO:22:

```
ATT CAT GAT TAT AAC ACA CGG GGC ACT ACC AAC AGC TTC CAC ATC CAG        48
Ile His Asp Tyr Asn Thr Arg Gly Thr Thr Asn Ser Phe His Ile Gln
 1               5                  10                  15

ACC AAA TCG GAA TGC GCC ATC CTG TAC AAC GAC CGC TCA GTG CTG GAG        96
Thr Lys Ser Glu Cys Ala Ile Leu Tyr Asn Asp Arg Ser Val Leu Glu
                20                  25                  30

AAT CAC CAC ATC AGC TCG GTT TTC CGA ATG ATG CAG GAC GAC GAC ATG       144
Asn His His Ile Ser Ser Val Phe Arg Met Met Gln Asp Asp Asp Met
            35                  40                  45

AAC ATC TTC ATC AAC CTC ACC AAG GAT GAG TTT GTA GAG CTG CGG GCT       192
Asn Ile Phe Ile Asn Leu Thr Lys Asp Glu Phe Val Glu Leu Arg Ala
        50                  55                  60

CTG GTC ATT GAG ATG GTG TTG GCC ACA GAC ATG TCC TGC CAT TTC CAG       240
Leu Val Ile Glu Met Val Leu Ala Thr Asp Met Ser Cys His Phe Gln
65                  70                  75                  80

CAA GTG AAG TCC ATG AAG ACA GCC TTG CAG CAG CTG GAG AGG ATT GAC       288
Gln Val Lys Ser Met Lys Thr Ala Leu Gln Gln Leu Glu Arg Ile Asp
                85                  90                  95

AAG TCC AAG GCC CTC TCT CTG CTG CTT CAT GCT GCT GAC ATC AGC CAC       336
Lys Ser Lys Ala Leu Ser Leu Leu Leu His Ala Ala Asp Ile Ser His
            100                 105                 110

CCC ACC AAG CAG TGG TCG GTT CAC AGC CGC TGG ACC AAG GCC CTC ATG       384
Pro Thr Lys Gln Trp Ser Val His Ser Arg Trp Thr Lys Ala Leu Met
        115                 120                 125

GAG GAG TTC TTC CGA CAA GGG GAC AAA G                                 412
Glu Glu Phe Phe Arg Gln Gly Asp Lys
130                 135
```

(2) INFORMATION FOR SEQ ID NO:23:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:23:

```
Ile His Asp Tyr Asn Thr Arg Gly Thr Thr Asn Ser Phe His Ile Gln
 1               5                  10                  15

Thr Lys Ser Glu Cys Ala Ile Leu Tyr Asn Asp Arg Ser Val Leu Glu
                20                  25                  30

Asn His His Ile Ser Ser Val Phe Arg Met Met Gln Asp Asp Asp Met
            35                  40                  45

Asn Ile Phe Ile Asn Leu Thr Lys Asp Glu Phe Val Glu Leu Arg Ala
        50                  55                  60

Leu Val Ile Glu Met Val Leu Ala Thr Asp Met Ser Cys His Phe Gln
65                  70                  75                  80

Gln Val Lys Ser Met Lys Thr Ala Leu Gln Gln Leu Glu Arg Ile Asp
                85                  90                  95

Lys Ser Lys Ala Leu Ser Leu Leu Leu His Ala Ala Asp Ile Ser His
            100                 105                 110

Pro Thr Lys Gln Trp Ser Val His Ser Arg Trp Thr Lys Ala Leu Met
```

```
              115                 120                 125
Glu Glu Phe Phe Arg Gln Gly Asp Lys
    130                 135

(2) INFORMATION FOR SEQ ID NO:24:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

AARAARAAYY TNGARTAYAC NGC                                              23

(2) INFORMATION FOR SEQ ID NO:25:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:25:

Lys Lys Asn Leu Glu Tyr Thr Ala
1               5

(2) INFORMATION FOR SEQ ID NO:26:

(i) SEQUENCE CHARACTERISTICS:
        (A) LENGTH: 1844 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 114..1715

(xi) SEQUENCE DESCRIPTION: SEQ ID NO:26:

GGCTGGGCAG CGGGAAAGGA GGAGCCGCAG GAACTGCAGC TCTGCCAGCT TGGGCCGAGC        60

TTTAGAGACC CCCGGCCTGG CTGGTCCCTG CCAGCCGCAG ACGGAGGCTG AGC ATG         116
                                                            Met
                                                             1

GAG CTG TCC CCC CGC AGC CCT CCC GAG ATG CTA GAG TCG GAC TGC CCT        164
Glu Leu Ser Pro Arg Ser Pro Pro Glu Met Leu Glu Ser Asp Cys Pro
        5                   10                  15

TCA CCC CTG GAG CTG AAG TCA GCC CCC AGC AAG AAG ATG TGG ATT AAG        212
Ser Pro Leu Glu Leu Lys Ser Ala Pro Ser Lys Lys Met Trp Ile Lys
    20                  25                  30

CTC CGG TCT CTG CTG CGC TAC ATG GTG AAG CAG TTG GAG AAC GGG GAG        260
Leu Arg Ser Leu Leu Arg Tyr Met Val Lys Gln Leu Glu Asn Gly Glu
 35                  40                  45

GTA AAC ATT GAG GAG CTG AAG AAA AAC CTG GAG TAC ACA GCT TCT CTG        308
Val Asn Ile Glu Glu Leu Lys Lys Asn Leu Glu Tyr Thr Ala Ser Leu
 50                  55                  60                  65

CTG GAG GCC GTC TAT ATA GAT GAG ACT CGG CAA ATC CTG GAC ACG GAG        356
Leu Glu Ala Val Tyr Ile Asp Glu Thr Arg Gln Ile Leu Asp Thr Glu
                 70                  75                  80

GAT GAG CTG CAG GAG CTG CGG TCT GAT GCG GTG CCT TCA GAG GTG CGG        404
Asp Glu Leu Gln Glu Leu Arg Ser Asp Ala Val Pro Ser Glu Val Arg
```

|  |  |
|---|---|
| GAC TGG CTG GCC TCC ACC TTC ACC CAG CAG ACC CGG GCC AAA GGC CCG<br>Asp Trp Leu Ala Ser Thr Phe Thr Gln Gln Thr Arg Ala Lys Gly Pro<br>                   100                        105                   110 | 452 |

```
                        85                      90                      95
GAC TGG CTG GCC TCC ACC TTC ACC CAG CAG ACC CGG GCC AAA GGC CCG       452
Asp Trp Leu Ala Ser Thr Phe Thr Gln Gln Thr Arg Ala Lys Gly Pro
            100                     105                     110

AGC GAA GAG AAG CCC AAG TTC CGG AGC ATC GTG CAC GCG GTG CAG GCT       500
Ser Glu Glu Lys Pro Lys Phe Arg Ser Ile Val His Ala Val Gln Ala
        115                     120                     125

GGC ATC TTT GTG GAG CGG ATG TTC CGG AGA ACG TAC ACC TCT GTG GGC       548
Gly Ile Phe Val Glu Arg Met Phe Arg Arg Thr Tyr Thr Ser Val Gly
130                     135                     140                 145

CCC ACC TAC TCC ACT GCC GTC CTC AAC TGT CTC AAG AAC GTG GAC CTT       596
Pro Thr Tyr Ser Thr Ala Val Leu Asn Cys Leu Lys Asn Val Asp Leu
                    150                     155                     160

TGG TGC TTT GAT GTC TTT TCC TTG AAC CGG GCA GCA GAT GAC CAC GCC       644
Trp Cys Phe Asp Val Phe Ser Leu Asn Arg Ala Ala Asp Asp His Ala
                165                     170                     175

CTG AGG ACC ATC GTT TTT GAG CTG CTG ACT CGG CAC AAC CTC ATC AGC       692
Leu Arg Thr Ile Val Phe Glu Leu Leu Thr Arg His Asn Leu Ile Ser
            180                     185                     190

CGC TTT AAG ATT CCC ACT GTG TTT TTG ATG ACT TTC CTG GAT GCC TTG       740
Arg Phe Lys Ile Pro Thr Val Phe Leu Met Thr Phe Leu Asp Ala Leu
195                     200                     205

GAG ACA GGC TAC GGA AAG TAC AAG AAC CCT TAC CAC AAC CAG ATC CAC       788
Glu Thr Gly Tyr Gly Lys Tyr Lys Asn Pro Tyr His Asn Gln Ile His
210                     215                     220                 225

GCA GCT GAC GTC ACC CAG ACG GTC CAC TGC TTC TTG CTC CGC ACA GGG       836
Ala Ala Asp Val Thr Gln Thr Val His Cys Phe Leu Leu Arg Thr Gly
                    230                     235                     240

ATG GTG CAC TGC CTG TCG GAG ATT GAG GTC CTG GCC ATC ATC TTT GCT       884
Met Val His Cys Leu Ser Glu Ile Glu Val Leu Ala Ile Ile Phe Ala
                245                     250                     255

GCA GCG ATC CAC GAC TAT GAG CAC ACT GGC ACT ACC AAC AGC TTC CAC       932
Ala Ala Ile His Asp Tyr Glu His Thr Gly Thr Thr Asn Ser Phe His
            260                     265                     270

ATC CAG ACC AAA TCG GAA TGC GCC ATC CTG TAC AAC GAC CGC TCA GTG       980
Ile Gln Thr Lys Ser Glu Cys Ala Ile Leu Tyr Asn Asp Arg Ser Val
275                     280                     285

CTG GAG AAT CAC CAC ATC AGC TCG GTT TTC CGA ATG ATG CAG GAC GAC      1028
Leu Glu Asn His His Ile Ser Ser Val Phe Arg Met Met Gln Asp Asp
290                     295                     300                 305

GAG ATG AAC ATC TTC ATC AAC CTC ACC AAG GAT GAG TTT GTA GAG CTG      1076
Glu Met Asn Ile Phe Ile Asn Leu Thr Lys Asp Glu Phe Val Glu Leu
                    310                     315                     320

CGG GCT CTG GTC ATT GAG ATG GTG TTG GCC ACA GAC ATG TCC TGC CAT      1124
Arg Ala Leu Val Ile Glu Met Val Leu Ala Thr Asp Met Ser Cys His
                325                     330                     335

TTC CAG CAA GTG AAG TCC ATG AAG ACA GCC TTG CAG CAG CTG GAG AGG      1172
Phe Gln Gln Val Lys Ser Met Lys Thr Ala Leu Gln Gln Leu Glu Arg
            340                     345                     350

ATT GAC AAG TCC AAG GCC CTC TCT CTG CTG CTT CAT GCT GCT GAC ATC      1220
Ile Asp Lys Ser Lys Ala Leu Ser Leu Leu Leu His Ala Ala Asp Ile
355                     360                     365

AGC CAC CCC ACC AAG CAG TGG TCG GTT CAC AGC CGC TGG ACC AAG GCC      1268
Ser His Pro Thr Lys Gln Trp Ser Val His Ser Arg Trp Thr Lys Ala
370                     375                     380                 385

CTC ATG GAG GAA TTC TTC CGC CAG GGT GAC AAG GAG GCT GAG CTG GGC      1316
Leu Met Glu Glu Phe Phe Arg Gln Gly Asp Lys Glu Ala Glu Leu Gly
                    390                     395                     400

CTG CCC TTT TCT CCG CTC TGT GAC CGC ACT TCC ACC CTC GTG GCG CAG      1364
Leu Pro Phe Ser Pro Leu Cys Asp Arg Thr Ser Thr Leu Val Ala Gln
```

|  | 405 |  |  |  | 410 |  |  |  | 415 |  |  |  |  |
|---|---|---|---|---|---|---|---|---|---|---|---|---|---|
| TCC | CAG | ATT | GGT | TTC | ATC | GAC | TTC | ATT | GTG | GAG | CCC | ACG | TTC TCT GTG | 1412 |
| Ser | Gln | Ile | Gly | Phe | Ile | Asp | Phe | Ile | Val | Glu | Pro | Thr | Phe Ser Val |
|  |  | 420 |  |  |  | 425 |  |  |  | 430 |  |  |

| CTC | ACC | GAT | GTG | GCT | GAG | AAG | AGT | GTC | CAG | CCC | ACC | GGG | GAC GAC GAC | 1460 |
| Leu | Thr | Asp | Val | Ala | Glu | Lys | Ser | Val | Gln | Pro | Thr | Gly | Asp Asp Asp |
|  | 435 |  |  |  | 440 |  |  |  | 445 |  |  |  |  |

| TCG | AAG | TCT | AAA | AAC | CAG | CCC | AGC | TTC | CAG | TGG | CGC | CAG | CCT TCT CTG | 1508 |
| Ser | Lys | Ser | Lys | Asn | Gln | Pro | Ser | Phe | Gln | Trp | Arg | Gln | Pro Ser Leu |
| 450 |  |  |  |  | 455 |  |  |  |  | 460 |  |  |  | 465 |

| GAT | GTA | GAA | GTG | GGA | GAC | CCC | AAC | CCT | GAC | GTG | GTC | AGC | TTC CGC TCC | 1556 |
| Asp | Val | Glu | Val | Gly | Asp | Pro | Asn | Pro | Asp | Val | Val | Ser | Phe Arg Ser |
|  |  |  | 470 |  |  |  | 475 |  |  |  |  | 480 |

| ACC | TGG | ACC | AAA | TAC | ATT | CAG | GAG | AAC | AAG | CAG | AAA | TGG | AAG GAA CGG | 1604 |
| Thr | Trp | Thr | Lys | Tyr | Ile | Gln | Glu | Asn | Lys | Gln | Lys | Trp | Lys Glu Arg |
|  |  | 485 |  |  |  |  | 490 |  |  |  |  | 495 |

| GCG | GCG | AGC | GGC | ATC | ACC | AAC | CAG | ATG | TCC | ATT | GAC | GAA | CTG TCC CCT | 1652 |
| Ala | Ala | Ser | Gly | Ile | Thr | Asn | Gln | Met | Ser | Ile | Asp | Glu | Leu Ser Pro |
|  |  | 500 |  |  |  | 505 |  |  |  |  | 510 |

| TGT | GAG | GAA | GAG | GCC | CCA | GCC | TCC | CCT | GCC | GAA | GAC | GAG | CAC AAC CAG | 1700 |
| Cys | Glu | Glu | Glu | Ala | Pro | Ala | Ser | Pro | Ala | Glu | Asp | Glu | His Asn Gln |
| 515 |  |  |  |  | 520 |  |  |  |  | 525 |

| AAC | GGG | AAT | CTG | GAC | TAGCGGGGCC | TGGCCAGGTC | CTCACTGAGT | CCTGAGTGTT | 1755 |
| Asn | Gly | Asn | Leu | Asp |
| 530 |

CGATGTCATC AGCACCATCC ATCGGGACTG GCTCCCCCAT CTGCTCCGAG GGCGAATGGA    1815

TGTCAAGGAA CAGAAAACCC ACCCGAAGA    1844

(2) INFORMATION FOR SEQ ID NO:27:

(i) SEQUENCE CHARACTERISTICS:
        (A) LENGTH: 534 amino acids
        (B) TYPE: amino acid
        (D) TOPOLOGY: linear (ii) MOLECULE TYPE: protein (xi) SEQUENCE DESCRIPTION: SEQ ID NO:27:

| Met | Glu | Leu | Ser | Pro | Arg | Ser | Pro | Glu | Met | Leu | Glu | Ser | Asp | Cys |
| 1 |  |  |  | 5 |  |  |  |  | 10 |  |  |  |  | 15 |

| Pro | Ser | Pro | Leu | Glu | Leu | Lys | Ser | Ala | Pro | Ser | Lys | Lys | Met | Trp | Ile |
|  |  |  | 20 |  |  |  |  | 25 |  |  |  |  | 30 |

| Lys | Leu | Arg | Ser | Leu | Leu | Arg | Tyr | Met | Val | Lys | Gln | Leu | Glu | Asn | Gly |
|  |  |  | 35 |  |  |  |  | 40 |  |  |  |  | 45 |

| Glu | Val | Asn | Ile | Glu | Glu | Leu | Lys | Lys | Asn | Leu | Glu | Tyr | Thr | Ala | Ser |
|  | 50 |  |  |  |  | 55 |  |  |  |  | 60 |

| Leu | Leu | Glu | Ala | Val | Tyr | Ile | Asp | Glu | Thr | Arg | Gln | Ile | Leu | Asp | Thr |
| 65 |  |  |  |  | 70 |  |  |  |  | 75 |  |  |  |  | 80 |

| Glu | Asp | Glu | Leu | Gln | Glu | Leu | Arg | Ser | Asp | Ala | Val | Pro | Ser | Glu | Val |
|  |  |  |  | 85 |  |  |  |  | 90 |  |  |  |  | 95 |

| Arg | Asp | Trp | Leu | Ala | Ser | Thr | Phe | Thr | Gln | Gln | Thr | Arg | Ala | Lys | Gly |
|  |  |  | 100 |  |  |  |  | 105 |  |  |  |  | 110 |

| Pro | Ser | Glu | Glu | Lys | Pro | Lys | Phe | Arg | Ser | Ile | Val | His | Ala | Val | Gln |
|  |  |  | 115 |  |  |  |  | 120 |  |  |  |  | 125 |

| Ala | Gly | Ile | Phe | Val | Glu | Arg | Met | Phe | Arg | Arg | Thr | Tyr | Thr | Ser | Val |
|  | 130 |  |  |  |  | 135 |  |  |  |  | 140 |

| Gly | Pro | Thr | Tyr | Ser | Thr | Ala | Val | Leu | Asn | Cys | Leu | Lys | Asn | Val | Asp |
| 145 |  |  |  |  | 150 |  |  |  |  | 155 |  |  |  |  | 160 |

```
Leu Trp Cys Phe Asp Val Phe Ser Leu Asn Arg Ala Ala Asp Asp His
            165                 170                 175

Ala Leu Arg Thr Ile Val Phe Glu Leu Leu Thr Arg His Asn Leu Ile
            180                 185                 190

Ser Arg Phe Lys Ile Pro Thr Val Phe Leu Met Thr Phe Leu Asp Ala
            195                 200                 205

Leu Glu Thr Gly Tyr Gly Lys Tyr Lys Asn Pro Tyr His Asn Gln Ile
210                 215                 220

His Ala Ala Asp Val Thr Gln Thr Val His Cys Phe Leu Leu Arg Thr
225                 230                 235                 240

Gly Met Val His Cys Leu Ser Glu Ile Glu Val Leu Ala Ile Ile Phe
                245                 250                 255

Ala Ala Ala Ile His Asp Tyr Glu His Thr Gly Thr Thr Asn Ser Phe
                260                 265                 270

His Ile Gln Thr Lys Ser Glu Cys Ala Ile Leu Tyr Asn Asp Arg Ser
            275                 280                 285

Val Leu Glu Asn His His Ile Ser Ser Val Phe Arg Met Met Gln Asp
290                 295                 300

Asp Glu Met Asn Ile Phe Ile Asn Leu Thr Lys Asp Glu Phe Val Glu
305                 310                 315                 320

Leu Arg Ala Leu Val Ile Glu Met Val Leu Ala Thr Asp Met Ser Cys
                325                 330                 335

His Phe Gln Gln Val Lys Ser Met Lys Thr Ala Leu Gln Gln Leu Glu
                340                 345                 350

Arg Ile Asp Lys Ser Lys Ala Leu Ser Leu Leu Leu His Ala Ala Asp
            355                 360                 365

Ile Ser His Pro Thr Lys Gln Trp Ser Val His Ser Arg Trp Thr Lys
370                 375                 380

Ala Leu Met Glu Glu Phe Phe Arg Gln Gly Asp Lys Glu Ala Glu Leu
385                 390                 395                 400

Gly Leu Pro Phe Ser Pro Leu Cys Asp Arg Thr Ser Thr Leu Val Ala
                405                 410                 415

Gln Ser Gln Ile Gly Phe Ile Asp Phe Ile Val Glu Pro Thr Phe Ser
            420                 425                 430

Val Leu Thr Asp Val Ala Glu Lys Ser Val Gln Pro Thr Gly Asp Asp
            435                 440                 445

Asp Ser Lys Ser Lys Asn Gln Pro Ser Phe Gln Trp Arg Gln Pro Ser
450                 455                 460

Leu Asp Val Glu Val Gly Asp Pro Asn Pro Asp Val Val Ser Phe Arg
465                 470                 475                 480

Ser Thr Trp Thr Lys Tyr Ile Gln Glu Asn Lys Gln Lys Trp Lys Glu
                485                 490                 495

Arg Ala Ala Ser Gly Ile Thr Asn Gln Met Ser Ile Asp Glu Leu Ser
            500                 505                 510

Pro Cys Glu Glu Glu Ala Pro Ala Ser Pro Ala Glu Asp Glu His Asn
            515                 520                 525

Gln Asn Gly Asn Leu Asp
530

(2) INFORMATION FOR SEQ ID NO:28:

(i) SEQUENCE CHARACTERISTICS:
        (A) LENGTH: 14 amino acids
        (B) TYPE: amino acid
        (D) TOPOLOGY: linear
```

(ii) MOLECULE TYPE: peptide (xi) SEQUENCE DESCRIPTION: SEQ ID NO:28:

Gln Leu Glu Asn Gly Glu Val Asn Ile Glu Glu Leu Lys Lys
1               5                   10

(2) INFORMATION FOR SEQ ID NO:29:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:29:

Gln Leu Ile Pro Gly Arg Val Asn Ile Ile Ser Leu Lys Lys
1               5                   10

(2) INFORMATION FOR SEQ ID NO:30:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:30:

Lys Ser Glu Cys Ala Ile Leu Tyr Asn Asp Arg Ser Val Leu Glu Asn
1               5                   10                  15

(2) INFORMATION FOR SEQ ID NO:31:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:31:

Lys Asp Glu Thr Ala Ile Leu Tyr Asn Asp Arg Thr Val Leu Glu Asn
1               5                   10                  15

(2) INFORMATION FOR SEQ ID NO:32:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

GGATCCGGAT CCCGCAGACG GAGGCTGAGC ATGG                              34

(2) INFORMATION FOR SEQ ID NO:33:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

```
GGATCCGGAT CCAGGACCTG GCCAGGCCCG GC                              32

(2) INFORMATION FOR SEQ ID NO:34:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:34:

Glu Met Met Met Tyr His Met Lys
1               5

(2) INFORMATION FOR SEQ ID NO:35:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (xi) SEQUENCE DESCRIPTION: SEQ ID NO:35:

Tyr His Asn Trp Met His Ala Phe
1               5

(2) INFORMATION FOR SEQ ID NO:36:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:36:

TTCATRTGRT ACATCATCAT YTC                                        23

(2) INFORMATION FOR SEQ ID NO:37:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:37:

AANGCRTGCA TCCARTTRTG RTA                                        23

(2) INFORMATION FOR SEQ ID NO:38:

(i) SEQUENCE CHARACTERISTICS:
          (A) LENGTH: 4131 base pairs
          (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 148..2910

(xi) SEQUENCE DESCRIPTION: SEQ ID NO:38:

AGGCGCAGCG GCCGGGCCGG CGGGCGGGCG GGCGGCTGCG AGCATGGTCC TGGTGCTGCA    60
```

```
CCACATCCTC ATCGCTGTTG TCCAATTCTT CAGGCGGGGC CAGCAGGTCT TCCTCAAGCC         120

GGACGAGCCG CCGCCGCCGC CGCAGCC ATG CGC CGA CAG CCT GCA GCC AGC            171
                             Met Arg Arg Gln Pro Ala Ala Ser
                              1               5

CGG GAC CTC TTT GCA CAG GAG CCA GTG CCC CCA GGG AGT GGA GAC GGC           219
Arg Asp Leu Phe Ala Gln Glu Pro Val Pro Pro Gly Ser Gly Asp Gly
     10              15                  20

GCA TTG CAG GAT GCT TTG CTG AGC CTG GGC TCC GTC ATC GAC GTT GCA           267
Ala Leu Gln Asp Ala Leu Leu Ser Leu Gly Ser Val Ile Asp Val Ala
 25              30                  35                  40

GGC TTG CAA CAG GCT GTC AAG GAG GCC CTG TCG GCT GTG CTT CCC AAA           315
Gly Leu Gln Gln Ala Val Lys Glu Ala Leu Ser Ala Val Leu Pro Lys
             45                  50                  55

GTG GAG ACG GTC TAC ACC TAC CTG CTG GAT GGG GAA TCC CGG CTG GTG           363
Val Glu Thr Val Tyr Thr Tyr Leu Leu Asp Gly Glu Ser Arg Leu Val
         60                  65                  70

TGT GAG GAG CCC CCC CAC GAG CTG CCC CAG GAG GGG AAA GTG CGA GAG           411
Cys Glu Glu Pro Pro His Glu Leu Pro Gln Glu Gly Lys Val Arg Glu
     75                  80                  85

GCT GTG ATC TCC CGG AAG CGG CTG GGC TGC AAT GGA CTG GGC CCC TCA           459
Ala Val Ile Ser Arg Lys Arg Leu Gly Cys Asn Gly Leu Gly Pro Ser
 90                  95                 100

GAC CTG CCT GGG AAG CCC TTG GCA AGG CTG GTG GCT CCA CTG GCT CCT           507
Asp Leu Pro Gly Lys Pro Leu Ala Arg Leu Val Ala Pro Leu Ala Pro
105                 110                 115                 120

GAC ACC CAA GTG CTG GTC ATA CCG CTG GTG GAC AAG GAG GCC GGG GCT           555
Asp Thr Gln Val Leu Val Ile Pro Leu Val Asp Lys Glu Ala Gly Ala
                125                 130                 135

GTG GCA GCT GTC ATC TTG GTG CAC TGT GGT CAG CTG AGT GAC AAT GAG           603
Val Ala Ala Val Ile Leu Val His Cys Gly Gln Leu Ser Asp Asn Glu
            140                 145                 150

GAG TGG AGC CTG CAA GCT GTG GAG AAG CAT ACC CTG GTG GCC CTG AAA           651
Glu Trp Ser Leu Gln Ala Val Glu Lys His Thr Leu Val Ala Leu Lys
        155                 160                 165

AGG GTG CAG GCC TTG CAG CAG CGC GAG TCC AGC GTG GCC CCG GAA GCG           699
Arg Val Gln Ala Leu Gln Gln Arg Glu Ser Ser Val Ala Pro Glu Ala
170                 175                 180

ACC CAG AAT CCT CCG GAG GAG GCA GCG GGA GAC CAG AAG GGT GGG GTC           747
Thr Gln Asn Pro Pro Glu Glu Ala Ala Gly Asp Gln Lys Gly Gly Val
185                 190                 195                 200

GCA TAC ACA AAC CAA GAC CGA AAG ATC CTG CAG CTT TGC GGG GAG CTC           795
Ala Tyr Thr Asn Gln Asp Arg Lys Ile Leu Gln Leu Cys Gly Glu Leu
                205                 210                 215

TAC GAC CTG GAT GCA TCT TCC CTG CAG CTC AAA GTC CTC CAA TAT CTG           843
Tyr Asp Leu Asp Ala Ser Ser Leu Gln Leu Lys Val Leu Gln Tyr Leu
            220                 225                 230

CAA CAG GAG ACC CAG GCA TCC CGC TGC TGC CTG CTG CTG GTA TCC GAG           891
Gln Gln Glu Thr Gln Ala Ser Arg Cys Cys Leu Leu Leu Val Ser Glu
        235                 240                 245

GAC AAT CTT CAG CTC TCC TGC AAG GTC ATT GGA GAT AAA GTA CTG GAG           939
Asp Asn Leu Gln Leu Ser Cys Lys Val Ile Gly Asp Lys Val Leu Glu
250                 255                 260

GAA GAG ATC AGC TTT CCG TTG ACC ACA GGA CGC CTG GGC CAA GTG GTG           987
Glu Glu Ile Ser Phe Pro Leu Thr Thr Gly Arg Leu Gly Gln Val Val
265                 270                 275                 280

GAA GAC AAG AAG TCT ATC CAG CTG AAA GAT CTC ACC TCC GAG GAT ATG          1035
Glu Asp Lys Lys Ser Ile Gln Leu Lys Asp Leu Thr Ser Glu Asp Met
                285                 290                 295

CAA CAG CTG CAA AGC ATG TTG GGC TGT GAG GTG CAG GCC ATG CTC TGT          1083
```

```
                Gln Gln Leu Gln Ser Met Leu Gly Cys Glu Val Gln Ala Met Leu Cys
                                300                 305                 310

GTC CCT GTC ATC AGC CGG GCC ACT GAC CAG GTC GTG GCC CTG GCC TGT              1131
Val Pro Val Ile Ser Arg Ala Thr Asp Gln Val Val Ala Leu Ala Cys
            315                 320                 325

GCC TTC AAC AAG CTC GGA GGA GAC TTG TTC ACA GAC CAG GAC GAG CAC              1179
Ala Phe Asn Lys Leu Gly Gly Asp Leu Phe Thr Asp Gln Asp Glu His
        330                 335                 340

GTG ATC CAG CAC TGC TTC CAC TAC ACC AGC ACA GTG CTC ACC AGC ACC              1227
Val Ile Gln His Cys Phe His Tyr Thr Ser Thr Val Leu Thr Ser Thr
345                 350                 355                 360

CTG GCC TTC CAG AAG GAG CAG AAG CTC AAG TGT GAG TGC CAG GCT CTT              1275
Leu Ala Phe Gln Lys Glu Gln Lys Leu Lys Cys Glu Cys Gln Ala Leu
                365                 370                 375

CTC CAA GTG GCG AAG AAC CTC TTC ACT CAT CTG GAT GAC GTC TCC GTG              1323
Leu Gln Val Ala Lys Asn Leu Phe Thr His Leu Asp Asp Val Ser Val
            380                 385                 390

CTG CTC CAG GAG ATC ATC ACA GAG GCC AGG AAC CTC AGC AAT GCT GAG              1371
Leu Leu Gln Glu Ile Ile Thr Glu Ala Arg Asn Leu Ser Asn Ala Glu
        395                 400                 405

ATC TGC TCT GTG TTC CTG CTG GAT CAG AAC GAG CTG GTG GCC AAG GTG              1419
Ile Cys Ser Val Phe Leu Leu Asp Gln Asn Glu Leu Val Ala Lys Val
410                 415                 420

TTC GAT GGG GGT GTG GTG GAA GAT GAG AGC TAT GAG ATC CGC ATT CCC              1467
Phe Asp Gly Gly Val Val Glu Asp Glu Ser Tyr Glu Ile Arg Ile Pro
425                 430                 435                 440

GCT GAC CAG GGC ATC GCG GGT CAT GTG GCG ACC ACC GGC CAG ATC CTA              1515
Ala Asp Gln Gly Ile Ala Gly His Val Ala Thr Thr Gly Gln Ile Leu
                445                 450                 455

AAC ATC CCA GAT GCT TAC GCA CAT CCG CTT TTC TAC CGA GGC GTG GAC              1563
Asn Ile Pro Asp Ala Tyr Ala His Pro Leu Phe Tyr Arg Gly Val Asp
            460                 465                 470

GAC AGC ACC GGC TTC CGG ACG CGC AAC ATC CTC TGC TTC CCC ATC AAG              1611
Asp Ser Thr Gly Phe Arg Thr Arg Asn Ile Leu Cys Phe Pro Ile Lys
        475                 480                 485

AAC GAG AAC CAG GAG GTC ATC GGT GTG GCC GAG CTG GTG AAC AAG ATC              1659
Asn Glu Asn Gln Glu Val Ile Gly Val Ala Glu Leu Val Asn Lys Ile
    490                 495                 500

AAT GGA CCA TGG TTC AGC AAG TTT GAT GAA GAC CTG GCT ACA GCC TTC              1707
Asn Gly Pro Trp Phe Ser Lys Phe Asp Glu Asp Leu Ala Thr Ala Phe
505                 510                 515                 520

TCC ATC TAC TGT GGC ATC AGC ATT GCC CAT TCC CTC CTA TAC AAG AAA              1755
Ser Ile Tyr Cys Gly Ile Ser Ile Ala His Ser Leu Leu Tyr Lys Lys
                525                 530                 535

GTG AAT GAG GCG CAG TAT CGC AGC CAC CTT GCC AAT GAG ATG ATG ATG              1803
Val Asn Glu Ala Gln Tyr Arg Ser His Leu Ala Asn Glu Met Met Met
            540                 545                 550

TAC CAC ATG AAG GTC TCT GAT GAC GAG TAC ACC AAA CTT CTC CAT GAC              1851
Tyr His Met Lys Val Ser Asp Asp Glu Tyr Thr Lys Leu Leu His Asp
        555                 560                 565

GGG ATC CAG CCT GTG GCT GCC ATC GAC TCC AAC TTT GCC AGT TTC ACA              1899
Gly Ile Gln Pro Val Ala Ala Ile Asp Ser Asn Phe Ala Ser Phe Thr
    570                 575                 580

TAC ACT CCT CGC TCT CTG CCC GAG GAT GAC ACT TCC ATG GCC ATC CTG              1947
Tyr Thr Pro Arg Ser Leu Pro Glu Asp Asp Thr Ser Met Ala Ile Leu
585                 590                 595                 600

AGC ATG CTG CAG GAC ATG AAT TTC ATC AAT AAC TAC AAA ATT GAC TGC              1995
Ser Met Leu Gln Asp Met Asn Phe Ile Asn Asn Tyr Lys Ile Asp Cys
                605                 610                 615

CCG ACA CTG GCC CGG TTC TGT TTG ATG GTG AAG AAG GGC TAC CGG GAT              2043
```

| | | |
|---|---|---|
| Pro Thr Leu Ala Arg Phe Cys Leu Met Val Lys Lys Gly Tyr Arg Asp<br>620 625 630 | | |
| CCC CCC TAC CAC AAC TGG ATG CAC GCC TTT TCT GTC TCC CAC TTC TGC<br>Pro Pro Tyr His Asn Trp Met His Ala Phe Ser Val Ser His Phe Cys<br>635 640 645 | | 2091 |
| TAC CTG CTC TAC AAG AAC CTG GAG CTC ACC AAC TAC CTC GAG GAC ATG<br>Tyr Leu Leu Tyr Lys Asn Leu Glu Leu Thr Asn Tyr Leu Glu Asp Met<br>650 655 660 | | 2139 |
| GAG ATC TTT GCC TTG TTT ATT TCC TGC ATG TGT CAC GAC CTG GAC CAC<br>Glu Ile Phe Ala Leu Phe Ile Ser Cys Met Cys His Asp Leu Asp His<br>665 670 675 680 | | 2187 |
| AGA GGC ACA AAC AAC TCC TTC CAG GTG GCC TCG AAA TCT GTG CTG GCC<br>Arg Gly Thr Asn Asn Ser Phe Gln Val Ala Ser Lys Ser Val Leu Ala<br>685 690 695 | | 2235 |
| GCG CTC TAC AGC TCG GAA GGC TCT GTC ATG GAG AGG CAC CAC TTC GCT<br>Ala Leu Tyr Ser Ser Glu Gly Ser Val Met Glu Arg His His Phe Ala<br>700 705 710 | | 2283 |
| CAG GCC ATT GCC ATC CTC AAC ACC CAC GGC TGC AAC ATC TTT GAC CAC<br>Gln Ala Ile Ala Ile Leu Asn Thr His Gly Cys Asn Ile Phe Asp His<br>715 720 725 | | 2331 |
| TTC TCC CGG AAG GAT TAT CAG CGC ATG TTG GAC CTG ATG CGG GAC ATC<br>Phe Ser Arg Lys Asp Tyr Gln Arg Met Leu Asp Leu Met Arg Asp Ile<br>730 735 740 | | 2379 |
| ATC TTG GCC ACA GAT CTG GCC CAC CAC CTC CGC ATC TTC AAG GAC CTC<br>Ile Leu Ala Thr Asp Leu Ala His His Leu Arg Ile Phe Lys Asp Leu<br>745 750 755 760 | | 2427 |
| CAA AAG ATG GCC GAA GTG GGC TAT GAT CGA ACC AAC AAG CAG CAC CAC<br>Gln Lys Met Ala Glu Val Gly Tyr Asp Arg Thr Asn Lys Gln His His<br>765 770 775 | | 2475 |
| AGC CTC CTT CTC TGC CTC CTT ATG ACC TCC TGT GAC CTC TCT GAC CAG<br>Ser Leu Leu Leu Cys Leu Leu Met Thr Ser Cys Asp Leu Ser Asp Gln<br>780 785 790 | | 2523 |
| ACC AAG GGC TGG AAG ACC ACG AGG AAG ATC GCG GAG CTG ATC TAC AAA<br>Thr Lys Gly Trp Lys Thr Thr Arg Lys Ile Ala Glu Leu Ile Tyr Lys<br>795 800 805 | | 2571 |
| GAG TTC TTC TCC CAG GGA GAC TTG GAG AAG GCC ATG GGC AAC AGG CCG<br>Glu Phe Phe Ser Gln Gly Asp Leu Glu Lys Ala Met Gly Asn Arg Pro<br>810 815 820 | | 2619 |
| ATG GAG ATG ATG GAC CGT GAG AAG GCC TAC ATC CCC GAG CTG CAG ATC<br>Met Glu Met Met Asp Arg Glu Lys Ala Tyr Ile Pro Glu Leu Gln Ile<br>825 830 835 840 | | 2667 |
| AGC TTC ATG GAG CAC ATC GCA ATG CCC ATC TAC AAG CTG CTG CAA GAC<br>Ser Phe Met Glu His Ile Ala Met Pro Ile Tyr Lys Leu Leu Gln Asp<br>845 850 855 | | 2715 |
| CTG TTC CCC AAG GCG GCC GAG TTG TAC GAA CGC GTG GCC TCT AAT CGT<br>Leu Phe Pro Lys Ala Ala Glu Leu Tyr Glu Arg Val Ala Ser Asn Arg<br>860 865 870 | | 2763 |
| GAG CAC TGG ACC AAG GTG TCA CAC AAG TTC ACC ATC CGA GGC CTC CCG<br>Glu His Trp Thr Lys Val Ser His Lys Phe Thr Ile Arg Gly Leu Pro<br>875 880 885 | | 2811 |
| AGC AAC AAC TCG TTG GAC TTC CTG GAC GAG GAG TAT GAG GTG CCT GAC<br>Ser Asn Asn Ser Leu Asp Phe Leu Asp Glu Glu Tyr Glu Val Pro Asp<br>890 895 900 | | 2859 |
| CTG GAT GGC GCT AGG GCT CCC ATC AAT GGC TGT TGC AGC CTT GAT GCT<br>Leu Asp Gly Ala Arg Ala Pro Ile Asn Gly Cys Cys Ser Leu Asp Ala<br>905 910 915 920 | | 2907 |
| GAG TGAGTCCCTC CTGGGACCCC TCCCTGTCCA GGCCTCCTCC CACAAGCCTC<br>Glu | | 2960 |
| CACGGGCCTG GCCGCACGCC CTGGGACCAG AGCCAAGGGT CCTGGATTCT AGGCCAGGAC | | 3020 |

```
TTCCCATGTG ACCCGGGCGA GGTCTGACCT TCCCGGGCCT CAGCTTTCTT GTCTGTATAA      3080

TGGAAGACTT CAGCCTCACT GAGACTTTGT CACTTGTCCT CTGAGAGCAC AGGGGTAACC      3140

AATGAGCAGT GGACCCTGCT CTGCACCTCT GACCGCATCT TGGCAAGTCC CCACCCTCCA      3200

GGCCACTCCT TCTCTGAGGC AGCCGGATGG TTTCTTCTGG GCCCCATTCC TGCCCTACCA      3260

GACCTGTGCC CTTTCCTGTG GGGGCACCCT CACTGGCTCC CAGGATCCTC AGGCAAGAAC      3320

ATGAGACATC TGAGTGGGCA AAGGGTGGGT CTTAGAGACA GTTATCAGCC TGGCTGGAGG      3380

ACTAGAAGTA GCCATGGGAC CACCTGTGGC CCAGAGGACT GCCTTTGTAC TTATGGTGGG      3440

GACTGGGACC TGGGGATATA AGGGTCCCAG GAGGACACTG CCAGGGGGCC AGTGCAGTGC      3500

TCTGGGGAGA GGGGGCTCAG GAAGAGAGGA GGATAAGAAC AGTGAGAAGG AAGGATCCCT      3560

GGGTTGGGAG GCAGGCCCAG CATGGGTCAG CCATGCTTCC TCCTGGCTGT GTGACCCTGG      3620

GCAAGTCCCT TCCCCTCTCT GCGAAACAGT AGGGTGAGAC AATCCATTCT CTAAGACCCC      3680

TTTTAGATCC AAGTCCCCAT AGTTCTGTGG AGTCCCAGTA GAGGCCACCG AGGGTCCCTG      3740

GCCCCCTTGG GCACAGAGCT GACACTGAGT CCCTCAGTGG CCCCCTGAGT ATACCCCCTT      3800

AGCCGGAGCC CCTTCCCCAT TCCTACAGCC AGAGGGGGAC CTGGCCTCAG CCTGGCAGGG      3860

CCTCTCTCCT CTTCAAGGCC ATATCCACCT GTGCCCCGGG GCTTGGGAGA CCCCCTAGGG      3920

CCGGAGCTCT GGGGTCATCC TGGCCACTGG CTTCTCCTTT CTCTGTTTTG TTCTGTATGT      3980

GTTGTGGGGT GGGGGGAGGG GGGCCACCTG CCTTACCTAT TCTGAGTTGC CTTTAGAGAG      4040

ATGCGTTTTT TCTAGGACTC TGTGCAACTG TTGTATATGG TTCCGTGGGC TGACCGCTTT      4100

GTACATGAGA ATAAATCTAT TTCTTTCTAC C                                    4131

(2) INFORMATION FOR SEQ ID NO:39:

(i) SEQUENCE CHARACTERISTICS:
        (A) LENGTH: 921 amino acids
        (B) TYPE: amino acid
        (D) TOPOLOGY: linear (ii) MOLECULE TYPE: protein (xi) SEQUENCE DESCRIPTION: SEQ ID NO:39:

Met Arg Arg Gln Pro Ala Ala Ser Arg Asp Leu Phe Ala Gln Glu Pro
1               5                   10                  15

Val Pro Pro Gly Ser Gly Asp Gly Ala Leu Gln Asp Ala Leu Leu Ser
                20                  25                  30

Leu Gly Ser Val Ile Asp Val Ala Gly Leu Gln Gln Ala Val Lys Glu
            35                  40                  45

Ala Leu Ser Ala Val Leu Pro Lys Val Glu Thr Val Tyr Thr Tyr Leu
        50                  55                  60

Leu Asp Gly Glu Ser Arg Leu Val Cys Glu Glu Pro Pro His Glu Leu
65                  70                  75                  80

Pro Gln Glu Gly Lys Val Arg Glu Ala Val Ile Ser Arg Lys Arg Leu
                85                  90                  95

Gly Cys Asn Gly Leu Gly Pro Ser Asp Leu Pro Gly Lys Pro Leu Ala
                100                 105                 110

Arg Leu Val Ala Pro Leu Ala Pro Asp Thr Gln Val Leu Val Ile Pro
            115                 120                 125

Leu Val Asp Lys Glu Ala Gly Ala Val Ala Ala Val Ile Leu Val His
        130                 135                 140

Cys Gly Gln Leu Ser Asp Asn Glu Glu Trp Ser Leu Gln Ala Val Glu
145                 150                 155                 160
```

-continued

```
Lys His Thr Leu Val Ala Leu Lys Arg Val Gln Ala Leu Gln Gln Arg
            165                 170                 175

Glu Ser Ser Val Ala Pro Glu Ala Thr Gln Asn Pro Pro Glu Glu Ala
            180                 185                 190

Ala Gly Asp Gln Lys Gly Gly Val Ala Tyr Thr Asn Gln Asp Arg Lys
            195                 200                 205

Ile Leu Gln Leu Cys Gly Glu Leu Tyr Asp Leu Asp Ala Ser Ser Leu
            210                 215                 220

Gln Leu Lys Val Leu Gln Tyr Leu Gln Gln Glu Thr Gln Ala Ser Arg
225                 230                 235                 240

Cys Cys Leu Leu Val Ser Glu Asp Asn Leu Gln Leu Ser Cys Lys
                245                 250                 255

Val Ile Gly Asp Lys Val Leu Glu Glu Glu Ile Ser Phe Pro Leu Thr
            260                 265                 270

Thr Gly Arg Leu Gly Gln Val Val Glu Asp Lys Lys Ser Ile Gln Leu
            275                 280                 285

Lys Asp Leu Thr Ser Glu Asp Met Gln Gln Leu Gln Ser Met Leu Gly
290                 295                 300

Cys Glu Val Gln Ala Met Leu Cys Val Pro Val Ile Ser Arg Ala Thr
305                 310                 315                 320

Asp Gln Val Val Ala Leu Ala Cys Ala Phe Asn Lys Leu Gly Gly Asp
            325                 330                 335

Leu Phe Thr Asp Gln Asp Glu His Val Ile Gln His Cys Phe His Tyr
            340                 345                 350

Thr Ser Thr Val Leu Thr Ser Thr Leu Ala Phe Gln Lys Glu Gln Lys
            355                 360                 365

Leu Lys Cys Glu Cys Gln Ala Leu Leu Gln Val Ala Lys Asn Leu Phe
            370                 375                 380

Thr His Leu Asp Asp Val Ser Val Leu Leu Gln Glu Ile Ile Thr Glu
385                 390                 395                 400

Ala Arg Asn Leu Ser Asn Ala Glu Ile Cys Ser Val Phe Leu Leu Asp
            405                 410                 415

Gln Asn Glu Leu Val Ala Lys Val Phe Asp Gly Gly Val Val Glu Asp
            420                 425                 430

Glu Ser Tyr Glu Ile Arg Ile Pro Ala Asp Gln Gly Ile Ala Gly His
            435                 440                 445

Val Ala Thr Thr Gly Gln Ile Leu Asn Ile Pro Asp Ala Tyr Ala His
            450                 455                 460

Pro Leu Phe Tyr Arg Gly Val Asp Asp Ser Thr Gly Phe Arg Thr Arg
465                 470                 475                 480

Asn Ile Leu Cys Phe Pro Ile Lys Asn Glu Asn Gln Glu Val Ile Gly
            485                 490                 495

Val Ala Glu Leu Val Asn Lys Ile Asn Gly Pro Trp Phe Ser Lys Phe
            500                 505                 510

Asp Glu Asp Leu Ala Thr Ala Phe Ser Ile Tyr Cys Gly Ile Ser Ile
            515                 520                 525

Ala His Ser Leu Leu Tyr Lys Lys Val Asn Glu Ala Gln Tyr Arg Ser
            530                 535                 540

His Leu Ala Asn Glu Met Met Met Tyr His Met Lys Val Ser Asp Asp
545                 550                 555                 560

Glu Tyr Thr Lys Leu Leu His Asp Gly Ile Gln Pro Val Ala Ala Ile
            565                 570                 575

Asp Ser Asn Phe Ala Ser Phe Thr Tyr Thr Pro Arg Ser Leu Pro Glu
            580                 585                 590
```

Asp Asp Thr Ser Met Ala Ile Leu Ser Met Leu Gln Asp Met Asn Phe
            595                 600                 605

Ile Asn Asn Tyr Lys Ile Asp Cys Pro Thr Leu Ala Arg Phe Cys Leu
    610                 615                 620

Met Val Lys Lys Gly Tyr Arg Asp Pro Pro Tyr His Asn Trp Met His
625                 630                 635                 640

Ala Phe Ser Val Ser His Phe Cys Tyr Leu Leu Tyr Lys Asn Leu Glu
                645                 650                 655

Leu Thr Asn Tyr Leu Glu Asp Met Glu Ile Phe Ala Leu Phe Ile Ser
            660                 665                 670

Cys Met Cys His Asp Leu Asp His Arg Gly Thr Asn Asn Ser Phe Gln
            675                 680                 685

Val Ala Ser Lys Ser Val Leu Ala Ala Leu Tyr Ser Ser Glu Gly Ser
690                 695                 700

Val Met Glu Arg His His Phe Ala Gln Ala Ile Ala Ile Leu Asn Thr
705                 710                 715                 720

His Gly Cys Asn Ile Phe Asp His Phe Ser Arg Lys Asp Tyr Gln Arg
                725                 730                 735

Met Leu Asp Leu Met Arg Asp Ile Ile Leu Ala Thr Asp Leu Ala His
            740                 745                 750

His Leu Arg Ile Phe Lys Asp Leu Gln Lys Met Ala Glu Val Gly Tyr
            755                 760                 765

Asp Arg Thr Asn Lys Gln His His Ser Leu Leu Leu Cys Leu Leu Met
770                 775                 780

Thr Ser Cys Asp Leu Ser Asp Gln Thr Lys Gly Trp Lys Thr Thr Arg
785                 790                 795                 800

Lys Ile Ala Glu Leu Ile Tyr Lys Glu Phe Phe Ser Gln Gly Asp Leu
                805                 810                 815

Glu Lys Ala Met Gly Asn Arg Pro Met Glu Met Met Asp Arg Glu Lys
            820                 825                 830

Ala Tyr Ile Pro Glu Leu Gln Ile Ser Phe Met Glu His Ile Ala Met
            835                 840                 845

Pro Ile Tyr Lys Leu Leu Gln Asp Leu Phe Pro Lys Ala Ala Glu Leu
850                 855                 860

Tyr Glu Arg Val Ala Ser Asn Arg Glu His Trp Thr Lys Val Ser His
865                 870                 875                 880

Lys Phe Thr Ile Arg Gly Leu Pro Ser Asn Asn Ser Leu Asp Phe Leu
                885                 890                 895

Asp Glu Glu Tyr Glu Val Pro Asp Leu Asp Gly Ala Arg Ala Pro Ile
            900                 905                 910

Asn Gly Cys Cys Ser Leu Asp Ala Glu
            915                 920

(2) INFORMATION FOR SEQ ID NO:40:

(i) SEQUENCE CHARACTERISTICS:
        (A) LENGTH: 249 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

ATATCGAATT CGGTTTAGTC TGGTTGGGGA GGCAGACGAT GAGGAGCGAT GGGGCAGGCA    60

TGCGGCCACT CCATCCTCTG CAGGAGCCAG CAGTACCCGG CTGCGCGACC GGCTGAGCCG   120

```
CGGGGCCAGC AGGTCTTCCT CAAGCCGGAC GAGCCGCCGC CGCCGCCGCA GCCATGCGCC        180

GACAGCCTGC AGGATGCTTT GCTGAGCCTG GGCTCCGTCA TTGAGCTTGC AGGCTTGCGA        240

CAGGCTGTC                                                                249
```

(2) INFORMATION FOR SEQ ID NO:41:

(i) SEQUENCE CHARACTERISTICS:
        (A) LENGTH: 250 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:41:

```
GAATTCGGGT AGAGCAGGTA GCAGAAGTGG GAGACAGAAA AGGCGTGCAT CCAGTTGTGG         60

TAGGGGGGAT CCCGGTAGCC CTTCTTCACC ATCAAACAGA ACCGGGCCAG TGTCGGGCAG        120

TCAATTTTGT AGTTATTGAT GAAATTCATG TTCTGCAGCA TGCTCAGGAT GGCCATGGAG        180

TGTCATCCTT GGGCAGAGAG CGAGGAGTGT ATGTGAACTG GCAAGTTGGA GTCGATGGCA        240

GCCACAGGCT                                                               250
```

(2) INFORMATION FOR SEQ ID NO:42:

(i) SEQUENCE CHARACTERISTICS:
        (A) LENGTH: 3789 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 181..3006

(xi) SEQUENCE DESCRIPTION: SEQ ID NO:42:

```
GCGGGAACTG CCAGGGCAGC AGGGCTGGAT TGGGGTGTTG AGTCCAGGCT GAGTCGGGGA         60

CAGGCCACTG TTCTTGGTCC CCGTGCCTGC TGGGCCAGGG GCCCTGCCTG GAGCCCCGGG        120

CAGGGTGGAC AGGGTGAGGT GCCACTTTAG TCTGGTTGGG GAGGCAGACG ATGAGGAGCG        180

ATG GGG CAG GCA TGC GGC CAC TCC ATC CTC TGC AGG AGC CAG CAG TAC         228
Met Gly Gln Ala Cys Gly His Ser Ile Leu Cys Arg Ser Gln Gln Tyr
  1               5                  10                  15

CCG GCT GCG CGA CCG GCT GAG CCG CGG GGC CAG CAG GTC TTC CTC AAG         276
Pro Ala Ala Arg Pro Ala Glu Pro Arg Gly Gln Gln Val Phe Leu Lys
             20                  25                  30

CCG GAC GAG CCG CCG CCG CCG CCG CAG CCA TGC GCC GAC AGC CTG CAG         324
Pro Asp Glu Pro Pro Pro Pro Pro Gln Pro Cys Ala Asp Ser Leu Gln
         35                  40                  45

GAT GCT TTG CTG AGC CTG GGC TCC GTC ATT GAC GTT GCA GGC TTG CAA         372
Asp Ala Leu Leu Ser Leu Gly Ser Val Ile Asp Val Ala Gly Leu Gln
     50                  55                  60

CAG GCT GTC AAG GAG GCC CTG TCG GCT GTG CTT CCC AAA GTG GAG ACG         420
Gln Ala Val Lys Glu Ala Leu Ser Ala Val Leu Pro Lys Val Glu Thr
 65                  70                  75                  80

GTC TAC ACC TAC CTG CTG GAT GGG GAA TCC CGG CTG GTG TGT GAG GAG         468
Val Tyr Thr Tyr Leu Leu Asp Gly Glu Ser Arg Leu Val Cys Glu Glu
                 85                  90                  95

CCC CCC CAC GAG CTG CCC CAG GAG GGG AAA GTG CGA GAG GCT GTG ATC         516
```

```
                                                             -continued

Pro Pro His Glu Leu Pro Gln Glu Gly Lys Val Arg Glu Ala Val Ile
                100                 105                 110

TCC CGG AAG CGG CTG GGC TGC AAT GGA CTG GGC CCC TCA GAC CTG CCT         564
Ser Arg Lys Arg Leu Gly Cys Asn Gly Leu Gly Pro Ser Asp Leu Pro
            115                 120                 125

GGG AAG CCC TTG GCA AGG CTG GTG GCT CCA CTG GCT CCT GAC ACC CAA         612
Gly Lys Pro Leu Ala Arg Leu Val Ala Pro Leu Ala Pro Asp Thr Gln
        130                 135                 140

GTG CTG GTC ATA CCG CTG GTG GAC AAG GAG GCC GGG GCT GTG GCA GCT         660
Val Leu Val Ile Pro Leu Val Asp Lys Glu Ala Gly Ala Val Ala Ala
145                 150                 155                 160

GTC ATC TTG GTG CAC TGT GGT CAG CTG AGT GAC AAT GAG GAG TGG AGC         708
Val Ile Leu Val His Cys Gly Gln Leu Ser Asp Asn Glu Glu Trp Ser
                165                 170                 175

CTG CAA GCT GTG GAG AAG CAT ACC CTG GTG GCC CTG AAA AGG GTG CAG         756
Leu Gln Ala Val Glu Lys His Thr Leu Val Ala Leu Lys Arg Val Gln
            180                 185                 190

GCC TTG CAG CAG CGC GAG TCC AGC GTG GCC CCG GAA GCG ACC CAG AAT         804
Ala Leu Gln Gln Arg Glu Ser Ser Val Ala Pro Glu Ala Thr Gln Asn
        195                 200                 205

CCT CCG GAG GAG GCA GCG GGA GAC CAG AAG GGT GGG GTC GCA TAC ACA         852
Pro Pro Glu Glu Ala Ala Gly Asp Gln Lys Gly Gly Val Ala Tyr Thr
    210                 215                 220

GAC CAA GAC CGA AAG ATC CTG CAG CTT TGC GGG GAG CTC TAC GAC CTG         900
Asp Gln Asp Arg Lys Ile Leu Gln Leu Cys Gly Glu Leu Tyr Asp Leu
225                 230                 235                 240

GAT GCA TCT TCC CTG CAG CTC AAA GTC CTC CAA TAT CTG CAA CAG GAG         948
Asp Ala Ser Ser Leu Gln Leu Lys Val Leu Gln Tyr Leu Gln Gln Glu
                245                 250                 255

ACC CAG GCA TCC CGC TGC TGC CTG CTG CTG GTA TCC GAG GAC AAT CTT         996
Thr Gln Ala Ser Arg Cys Cys Leu Leu Leu Val Ser Glu Asp Asn Leu
            260                 265                 270

CAG CTC TCC TGC AAG GTC ATT GGA GAT AAA GTA CTG GAG GAA GAG ATC        1044
Gln Leu Ser Cys Lys Val Ile Gly Asp Lys Val Leu Glu Glu Glu Ile
        275                 280                 285

AGC TTT CCG TTG ACC ACA GGA CGC CTG GGC CAA GTG GTG GAA GAC AAG        1092
Ser Phe Pro Leu Thr Thr Gly Arg Leu Gly Gln Val Val Glu Asp Lys
    290                 295                 300

AAG TCT ATC CAG CTG AAA GAT CTC ACC TCC GAG GAT ATG CAA CAG CTG        1140
Lys Ser Ile Gln Leu Lys Asp Leu Thr Ser Glu Asp Met Gln Gln Leu
305                 310                 315                 320

CAA AGC ATG TTG GGC TGT GAG GTG CAG GCC ATG CTC TGT GTC CCT GTC        1188
Gln Ser Met Leu Gly Cys Glu Val Gln Ala Met Leu Cys Val Pro Val
                325                 330                 335

ATC AGC CGG GCC ACT GAC CAG GTC GTG GCC CTG GCC TGT GCC TTC AAC        1236
Ile Ser Arg Ala Thr Asp Gln Val Val Ala Leu Ala Cys Ala Phe Asn
            340                 345                 350

AAG CTC GGA GGA GAC TTG TTC ACA GAC CAG GAC GAG CAC GTG ATC CAG        1284
Lys Leu Gly Gly Asp Leu Phe Thr Asp Gln Asp Glu His Val Ile Gln
        355                 360                 365

CAC TGC TTC CAC TAC ACC AGC ACA GTG CTC ACC AGC ACC CTG GCC TTC        1332
His Cys Phe His Tyr Thr Ser Thr Val Leu Thr Ser Thr Leu Ala Phe
    370                 375                 380

CAG AAG GAG CAG AAG CTC AAG TGT GAG TGC CAG GCT CTT CTC CAA GTG        1380
Gln Lys Glu Gln Lys Leu Lys Cys Glu Cys Gln Ala Leu Leu Gln Val
385                 390                 395                 400

GCG AAG AAC CTC TTC ACT CAT CTG GAT GAC GTC TCC GTG CTG CTC CAG        1428
Ala Lys Asn Leu Phe Thr His Leu Asp Asp Val Ser Val Leu Leu Gln
                405                 410                 415

GAG ATC ATC ACA GAG GCC AGG AAC CTC AGC AAT GCT GAG ATC TGC TCT        1476
```

-continued

```

Glu Ile Ile Thr Glu Ala Arg Asn Leu Ser Asn Ala Glu Ile Cys Ser
            420                 425                 430

GTG TTC CTG CTG GAT CAG AAC GAG CTG GTG GCC AAG GTG TTC GAT GGG    1524
Val Phe Leu Leu Asp Gln Asn Glu Leu Val Ala Lys Val Phe Asp Gly
            435                 440                 445

GGT GTG GTG GAA GAT GAG AGC TAT GAG ATC CGC ATT CCC GCT GAC CAG    1572
Gly Val Val Glu Asp Glu Ser Tyr Glu Ile Arg Ile Pro Ala Asp Gln
450                 455                 460

GGC ATC GCG GGT CAT GTG GCG ACC ACC GGC CAG ATC CTA AAC ATC CCA    1620
Gly Ile Ala Gly His Val Ala Thr Thr Gly Gln Ile Leu Asn Ile Pro
465                 470                 475                 480

GAT GCT TAC GCA CAT CCG CTT TTC TAC CGA GGC GTG GAC GAC AGC ACC    1668
Asp Ala Tyr Ala His Pro Leu Phe Tyr Arg Gly Val Asp Asp Ser Thr
            485                 490                 495

GGC TTC CGG ACG CGC AAC ATC CTC TGC TTC CCC ATC AAG AAC GAG AAC    1716
Gly Phe Arg Thr Arg Asn Ile Leu Cys Phe Pro Ile Lys Asn Glu Asn
            500                 505                 510

CAG GAG GTC ATC GGT GTG GCC GAG CTG GTG AAC AAG ATC AAT GGA CCA    1764
Gln Glu Val Ile Gly Val Ala Glu Leu Val Asn Lys Ile Asn Gly Pro
            515                 520                 525

TGG TTC AGC AAG TTT GAT GAA GAC CTG GCT ACA GCC TTC TCC ATC TAC    1812
Trp Phe Ser Lys Phe Asp Glu Asp Leu Ala Thr Ala Phe Ser Ile Tyr
            530                 535                 540

TGT GGC ATC AGC ATT GCC CAT TCC CTC CTA TAC AAG AAA GTG AAT GAG    1860
Cys Gly Ile Ser Ile Ala His Ser Leu Leu Tyr Lys Lys Val Asn Glu
545                 550                 555                 560

GCG CAG TAT CGC AGC CAC CTT GCC AAT GAG ATG ATG ATG TAC CAC ATG    1908
Ala Gln Tyr Arg Ser His Leu Ala Asn Glu Met Met Met Tyr His Met
            565                 570                 575

AAG GTC TCT GAT GAC GAG TAC ACC AAA CTT CTC CAT GAC GGG ATC CAG    1956
Lys Val Ser Asp Asp Glu Tyr Thr Lys Leu Leu His Asp Gly Ile Gln
            580                 585                 590

CCT GTG GCT GCC ATC GAC TCC AAC TTT GCC AGT TTC ACA TAC ACT CCT    2004
Pro Val Ala Ala Ile Asp Ser Asn Phe Ala Ser Phe Thr Tyr Thr Pro
            595                 600                 605

CGC TCT CTG CCC GAG GAT GAC ACT TCC ATG GCC ATC CTG AGC ATG CTG    2052
Arg Ser Leu Pro Glu Asp Asp Thr Ser Met Ala Ile Leu Ser Met Leu
            610                 615                 620

CAG GAC ATG AAT TTC ATC AAT AAC TAC AAA ATT GAC TGC CCG ACA CTG    2100
Gln Asp Met Asn Phe Ile Asn Asn Tyr Lys Ile Asp Cys Pro Thr Leu
625                 630                 635                 640

GCC CGG TTC TGT TTG ATG GTG AAG AAG GGC TAC CGG GAT CCC CCC TAC    2148
Ala Arg Phe Cys Leu Met Val Lys Lys Gly Tyr Arg Asp Pro Pro Tyr
            645                 650                 655

CAC AAC TGG ATG CAC GCC TTT TCT GTC TCC CAC TTC TGC TAC CTG CTC    2196
His Asn Trp Met His Ala Phe Ser Val Ser His Phe Cys Tyr Leu Leu
            660                 665                 670

TAC AAG AAC CTG GAG CTC ACC AAC TAC CTC GAG GAC ATG GAG ATC TTT    2244
Tyr Lys Asn Leu Glu Leu Thr Asn Tyr Leu Glu Asp Met Glu Ile Phe
            675                 680                 685

GCC TTG TTT ATT TCC TGC ATG TGT CAC GAC CTG GAC CAC AGA GGC ACA    2292
Ala Leu Phe Ile Ser Cys Met Cys His Asp Leu Asp His Arg Gly Thr
            690                 695                 700

AAC AAC TCC TTC CAG GTG GCC TCG AAA TCT GTG CTG GCC GCG CTC TAC    2340
Asn Asn Ser Phe Gln Val Ala Ser Lys Ser Val Leu Ala Ala Leu Tyr
705                 710                 715                 720

AGC TCG GAA GGC TCT GTC ATG GAG AGG CAC CAC TTC GCT CAG GCC ATT    2388
Ser Ser Glu Gly Ser Val Met Glu Arg His His Phe Ala Gln Ala Ile
            725                 730                 735

GCC ATC CTC AAC ACC CAC GGC TGC AAC ATC TTT GAC CAC TTC TCC CGG    2436
```

-continued

| | | | | | | | | | | | | | | |
|---|---|---|---|---|---|---|---|---|---|---|---|---|---|---|
| Ala | Ile | Leu | Asn | Thr | His | Gly | Cys | Asn | Ile | Phe | Asp | His | Phe | Ser | Arg |
| | | | 740 | | | | | 745 | | | | | 750 | | |

```
AAG GAT TAT CAG CGC ATG TTG GAC CTG ATG CGG GAC ATC ATC TTG GCC      2484
Lys Asp Tyr Gln Arg Met Leu Asp Leu Met Arg Asp Ile Ile Leu Ala
            755                 760                 765

ACA GAT CTG GCC CAC CAC CTC CGC ATC TTC AAG GAC CTC CAA AAG ATG      2532
Thr Asp Leu Ala His His Leu Arg Ile Phe Lys Asp Leu Gln Lys Met
770                 775                 780

GCC GAA GTG GGC TAT GAT CGA ACC AAC AAG CAG CAC CAC AGC CTC CTT      2580
Ala Glu Val Gly Tyr Asp Arg Thr Asn Lys Gln His His Ser Leu Leu
785                 790                 795                 800

CTC TGC CTC CTT ATG ACC TCC TGT GAC CTC TCT GAC CAG ACC AAG GGC      2628
Leu Cys Leu Leu Met Thr Ser Cys Asp Leu Ser Asp Gln Thr Lys Gly
                805                 810                 815

TGG AAG ACC ACG AGG AAG ATC GCG GAG CTG ATC TAC AAA GAG TTC TTC      2676
Trp Lys Thr Thr Arg Lys Ile Ala Glu Leu Ile Tyr Lys Glu Phe Phe
            820                 825                 830

TCC CAG GGA GAC TTG GAG AAG GCC ATG GGC AAC AGG CCG ATG GAG ATG      2724
Ser Gln Gly Asp Leu Glu Lys Ala Met Gly Asn Arg Pro Met Glu Met
                835                 840                 845

ATG GAC CGT GAG AAG GCC TAC ATC CCC GAG CTG CAG ATC AGC TTC ATG      2772
Met Asp Arg Glu Lys Ala Tyr Ile Pro Glu Leu Gln Ile Ser Phe Met
850                 855                 860

GAG CAC ATC GCA ATG CCC ATC TAC AAG CTG CTG CAA GAC CTG TTC CCC      2820
Glu His Ile Ala Met Pro Ile Tyr Lys Leu Leu Gln Asp Leu Phe Pro
865                 870                 875                 880

AAG GCG GCC GAG TTG TAC GAA CGC GTG GCC TCT AAT CGT GAG CAC TGG      2868
Lys Ala Ala Glu Leu Tyr Glu Arg Val Ala Ser Asn Arg Glu His Trp
                885                 890                 895

ACC AAG GTG TCA CAC AAG TTC ACC ATC CGA GGC CTC CCG AGC AAC AAC      2916
Thr Lys Val Ser His Lys Phe Thr Ile Arg Gly Leu Pro Ser Asn Asn
            900                 905                 910

TCG TTG GAC TTC CTG GAC GAG GAG TAT GAG GTG CCT GAC CTG GAT GGC      2964
Ser Leu Asp Phe Leu Asp Glu Glu Tyr Glu Val Pro Asp Leu Asp Gly
            915                 920                 925

GCT AGG GCT CCC ATC AAT GGC TGT TGC AGC CTT GAT GCT GAG              3006
Ala Arg Ala Pro Ile Asn Gly Cys Cys Ser Leu Asp Ala Glu
930                 935                 940

TGAGTCCCTC CTGGGACCCC TCCCTGTCCA GGCCTCCTCC CACAAGCCTC CACGGGCCTG    3066

GCCGCACGCC CTGGGACCAG AGCCAAGGGT CCTGGATTCT AGGCCAGGAC TTCCCATGTG    3126

ACCCGGGCGA GGTCTGACCT TCCCGGGCCT CAGCTTTCTT GTCTGTATAA TGGAAGACTT    3186

CAGCCTCACT GAGACTTTGT CACTTGTCCT CTGAGAGCAC AGGGGTAACC AATGAGCAGT    3246

GGACCCTGCT CTGCACCTCT GACCGCATCT TGGCAAGTCC CCACCCTCCA GGCCACTCCT    3306

TCTCTGAGGC AGCCGGATGG TTTCTTCTGG GCCCCATTCC TGCCCTACCA GACCTGTGCC    3366

CTTTCCTGTG GGGCACCCT CACTGGCTCC CAGGATCCTC AGGCAAGAAC ATGAGACATC     3426

TGAGTGGGCA AAGGGTGGGT CTTAGAGACA GTTATCAGCC TGGCTGGAGG ACTAGAAGTA    3486

GCCATGGGAC CACCTGTGGC CCAGAGGACT GCCTTTGTAC TTATGGTGGG GACTGGGACC    3546

TGGGGATATA AGGGTCCCAG GAGGACACTG CCAGGGGGCC AGTGCAGTGC TCTGGGGAGA    3606

GGGGGCTCAG GAAGAGAGGA GGATAAGAAC AGTGAGAAGG AAGGATCCCT GGGTTGGGAG    3666

GCAGGCCCAG CATGGGTCAG CCATGCTTCC TCCTGGCTGT GTGACCCTGG GCAAGTCCCT    3726

TCCCCTCTCT GCGAAACAGT AGGGTGAGAC AATCCATTCT CTAAGACCCC TTTTAGATCC    3786

AAG                                                                  3789
```

(2) INFORMATION FOR SEQ ID NO:43:

(i) SEQUENCE CHARACTERISTICS:
        (A) LENGTH: 942 amino acids
        (B) TYPE: amino acid
        (D) TOPOLOGY: linear (ii) MOLECULE TYPE: protein (xi) SEQUENCE DESCRIPTION: SEQ ID NO:43:

```
Met Gly Gln Ala Cys Gly His Ser Ile Leu Cys Arg Ser Gln Gln Tyr
 1               5                  10                  15

Pro Ala Ala Arg Pro Ala Glu Pro Arg Gly Gln Gln Val Phe Leu Lys
                20                  25                  30

Pro Asp Glu Pro Pro Pro Pro Gln Pro Cys Ala Asp Ser Leu Gln
            35                  40                  45

Asp Ala Leu Leu Ser Leu Gly Ser Val Ile Asp Val Ala Gly Leu Gln
        50                  55                  60

Gln Ala Val Lys Glu Ala Leu Ser Ala Val Leu Pro Lys Val Glu Thr
 65                  70                  75                  80

Val Tyr Thr Tyr Leu Leu Asp Gly Glu Ser Arg Leu Val Cys Glu Glu
                85                  90                  95

Pro Pro His Glu Leu Pro Gln Glu Gly Lys Val Arg Glu Ala Val Ile
            100                 105                 110

Ser Arg Lys Arg Leu Gly Cys Asn Gly Leu Gly Pro Ser Asp Leu Pro
        115                 120                 125

Gly Lys Pro Leu Ala Arg Leu Val Ala Pro Leu Ala Pro Asp Thr Gln
    130                 135                 140

Val Leu Val Ile Pro Leu Val Asp Lys Glu Ala Gly Ala Val Ala Ala
145                 150                 155                 160

Val Ile Leu Val His Cys Gly Gln Leu Ser Asp Asn Glu Glu Trp Ser
                165                 170                 175

Leu Gln Ala Val Glu Lys His Thr Leu Val Ala Leu Lys Arg Val Gln
            180                 185                 190

Ala Leu Gln Gln Arg Glu Ser Ser Val Ala Pro Glu Ala Thr Gln Asn
        195                 200                 205

Pro Pro Glu Glu Ala Ala Gly Asp Gln Lys Gly Gly Val Ala Tyr Thr
    210                 215                 220

Asp Gln Asp Arg Lys Ile Leu Gln Leu Cys Gly Glu Leu Tyr Asp Leu
225                 230                 235                 240

Asp Ala Ser Ser Leu Gln Leu Lys Val Leu Gln Tyr Leu Gln Gln Glu
                245                 250                 255

Thr Gln Ala Ser Arg Cys Cys Leu Leu Leu Val Ser Glu Asp Asn Leu
            260                 265                 270

Gln Leu Ser Cys Lys Val Ile Gly Asp Lys Val Leu Glu Glu Glu Ile
        275                 280                 285

Ser Phe Pro Leu Thr Thr Gly Arg Leu Gly Gln Val Val Glu Asp Lys
    290                 295                 300

Lys Ser Ile Gln Leu Lys Asp Leu Thr Ser Glu Asp Met Gln Gln Leu
305                 310                 315                 320

Gln Ser Met Leu Gly Cys Glu Val Gln Ala Met Leu Cys Val Pro Val
                325                 330                 335

Ile Ser Arg Ala Thr Asp Gln Val Val Ala Leu Ala Cys Ala Phe Asn
            340                 345                 350

Lys Leu Gly Gly Asp Leu Phe Thr Asp Gln Asp Glu His Val Ile Gln
        355                 360                 365
```

-continued

His Cys Phe His Tyr Thr Ser Thr Val Leu Thr Ser Thr Leu Ala Phe
370             375                 380

Gln Lys Glu Gln Lys Leu Lys Cys Glu Cys Gln Ala Leu Leu Gln Val
385                 390                 395                 400

Ala Lys Asn Leu Phe Thr His Leu Asp Asp Val Ser Val Leu Leu Gln
            405                 410                 415

Glu Ile Ile Thr Glu Ala Arg Asn Leu Ser Asn Ala Glu Ile Cys Ser
        420                 425                 430

Val Phe Leu Leu Asp Gln Asn Glu Leu Val Ala Lys Val Phe Asp Gly
        435                 440                 445

Gly Val Val Glu Asp Glu Ser Tyr Glu Ile Arg Ile Pro Ala Asp Gln
450                 455                 460

Gly Ile Ala Gly His Val Ala Thr Thr Gly Gln Ile Leu Asn Ile Pro
465                 470                 475                 480

Asp Ala Tyr Ala His Pro Leu Phe Tyr Arg Gly Val Asp Asp Ser Thr
            485                 490                 495

Gly Phe Arg Thr Arg Asn Ile Leu Cys Phe Pro Ile Lys Asn Glu Asn
        500                 505                 510

Gln Glu Val Ile Gly Val Ala Glu Leu Val Asn Lys Ile Asn Gly Pro
        515                 520                 525

Trp Phe Ser Lys Phe Asp Glu Asp Leu Ala Thr Ala Phe Ser Ile Tyr
530                 535                 540

Cys Gly Ile Ser Ile Ala His Ser Leu Leu Tyr Lys Lys Val Asn Glu
545                 550                 555                 560

Ala Gln Tyr Arg Ser His Leu Ala Asn Glu Met Met Met Tyr His Met
            565                 570                 575

Lys Val Ser Asp Asp Glu Tyr Thr Lys Leu Leu His Asp Gly Ile Gln
        580                 585                 590

Pro Val Ala Ala Ile Asp Ser Asn Phe Ala Ser Phe Thr Tyr Thr Pro
        595                 600                 605

Arg Ser Leu Pro Glu Asp Asp Thr Ser Met Ala Ile Leu Ser Met Leu
610                 615                 620

Gln Asp Met Asn Phe Ile Asn Asn Tyr Lys Ile Asp Cys Pro Thr Leu
625                 630                 635                 640

Ala Arg Phe Cys Leu Met Val Lys Lys Gly Tyr Arg Asp Pro Pro Tyr
            645                 650                 655

His Asn Trp Met His Ala Phe Ser Val Ser His Phe Cys Tyr Leu Leu
        660                 665                 670

Tyr Lys Asn Leu Glu Leu Thr Asn Tyr Leu Glu Asp Met Glu Ile Phe
        675                 680                 685

Ala Leu Phe Ile Ser Cys Met Cys His Asp Leu Asp His Arg Gly Thr
690                 695                 700

Asn Asn Ser Phe Gln Val Ala Ser Lys Ser Val Leu Ala Ala Leu Tyr
705                 710                 715                 720

Ser Ser Glu Gly Ser Val Met Glu Arg His His Phe Ala Gln Ala Ile
            725                 730                 735

Ala Ile Leu Asn Thr His Gly Cys Asn Ile Phe Asp His Phe Ser Arg
        740                 745                 750

Lys Asp Tyr Gln Arg Met Leu Asp Leu Met Arg Asp Ile Ile Leu Ala
        755                 760                 765

Thr Asp Leu Ala His His Leu Arg Ile Phe Lys Asp Leu Gln Lys Met
770                 775                 780

Ala Glu Val Gly Tyr Asp Arg Thr Asn Lys Gln His His Ser Leu Leu
785                 790                 795                 800

```
Leu Cys Leu Leu Met Thr Ser Cys Asp Leu Ser Asp Gln Thr Lys Gly
                805                 810                 815

Trp Lys Thr Thr Arg Lys Ile Ala Glu Leu Ile Tyr Lys Glu Phe Phe
        820                 825                 830

Ser Gln Gly Asp Leu Glu Lys Ala Met Gly Asn Arg Pro Met Glu Met
        835                 840                 845

Met Asp Arg Glu Lys Ala Tyr Ile Pro Glu Leu Gln Ile Ser Phe Met
    850                 855                 860

Glu His Ile Ala Met Pro Ile Tyr Lys Leu Leu Gln Asp Leu Phe Pro
865                 870                 875                 880

Lys Ala Ala Glu Leu Tyr Glu Arg Val Ala Ser Asn Arg Glu His Trp
                885                 890                 895

Thr Lys Val Ser His Lys Phe Thr Ile Arg Gly Leu Pro Ser Asn Asn
                900                 905                 910

Ser Leu Asp Phe Leu Asp Glu Glu Tyr Glu Val Pro Asp Leu Asp Gly
                915                 920                 925

Ala Arg Ala Pro Ile Asn Gly Cys Cys Ser Leu Asp Ala Glu
                930                 935                 940

(2) INFORMATION FOR SEQ ID NO:44:

(i) SEQUENCE CHARACTERISTICS:
        (A) LENGTH: 3044 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 12..2834

(xi) SEQUENCE DESCRIPTION: SEQ ID NO:44:

GAATTCTGAT A ATG GGG CAG GCA TGC GGC CAC TCC ATC CTC TGC AGG AGC        50
           Met Gly Gln Ala Cys Gly His Ser Ile Leu Cys Arg Ser
             1               5                  10

CAG CAG TAC CCG GCA GCG CGA CCG GCT GAG CCG CGG GGC CAG CAG GTC         98
Gln Gln Tyr Pro Ala Ala Arg Pro Ala Glu Pro Arg Gly Gln Gln Val
 15                  20                  25

TTC CTC AAG CCG GAC GAG CCG CCG CCG CCG CAG CCA TGC GCC GAC            146
Phe Leu Lys Pro Asp Glu Pro Pro Pro Pro Gln Pro Cys Ala Asp
 30                  35                  40                  45

AGC CTG CAG GAC GCC TTG CTG AGT CTG GGC TCT GTC ATC GAC ATT TCA        194
Ser Leu Gln Asp Ala Leu Leu Ser Leu Gly Ser Val Ile Asp Ile Ser
                 50                  55                  60

GGC CTG CAA CGT GCT GTC AAG GAG GCC CTG TCA GCT GTG CTC CCC CGA        242
Gly Leu Gln Arg Ala Val Lys Glu Ala Leu Ser Ala Val Leu Pro Arg
                 65                  70                  75

GTG GAA ACT GTC TAC ACC TAC CTA CTG GAT GGT GAG TCC CAG CTG GTG        290
Val Glu Thr Val Tyr Thr Tyr Leu Leu Asp Gly Glu Ser Gln Leu Val
         80                  85                  90

TGT GAG GAC CCC CCA CAT GAG CTG CCC CAG GAG GGG AAA GTC CGG GAG        338
Cys Glu Asp Pro Pro His Glu Leu Pro Gln Glu Gly Lys Val Arg Glu
     95                 100                 105

GCT ATC ATC TCC CAG AAG CGG CTG GGC TGC AAT GGG CTG GGC TTC TCA        386
Ala Ile Ile Ser Gln Lys Arg Leu Gly Cys Asn Gly Leu Gly Phe Ser
110                 115                 120                 125

GAC CTG CCA GGG AAG CCC TTG GCC AGG CTG GTG GCT CCA CTG GCT CCT        434
Asp Leu Pro Gly Lys Pro Leu Ala Arg Leu Val Ala Pro Leu Ala Pro
                130                 135                 140
```

```
GAT ACC CAA GTG CTG GTC ATG CCG CTA GCG GAC AAG GAG GCT GGG GCC         482
Asp Thr Gln Val Leu Val Met Pro Leu Ala Asp Lys Glu Ala Gly Ala
            145                 150                 155

GTG GCA GCT GTC ATC TTG GTG CAC TGT GGC CAG CTG AGT GAT AAT GAG         530
Val Ala Ala Val Ile Leu Val His Cys Gly Gln Leu Ser Asp Asn Glu
            160                 165                 170

GAA TGG AGC CTG CAG GCG GTG GAG AAG CAT ACC CTG GTC GCC CTG CGG         578
Glu Trp Ser Leu Gln Ala Val Glu Lys His Thr Leu Val Ala Leu Arg
        175                 180                 185

AGG GTG CAG GTC CTG CAG CAG CGC GGG CCC AGG GAG GCT CCC CGA GCC         626
Arg Val Gln Val Leu Gln Gln Arg Gly Pro Arg Glu Ala Pro Arg Ala
190                 195                 200                 205

GTC CAG AAC CCC CCG GAG GGG ACG GCG GAA GAC CAG AAG GGC GGG GCG         674
Val Gln Asn Pro Pro Glu Gly Thr Ala Glu Asp Gln Lys Gly Gly Ala
            210                 215                 220

GCG TAC ACC GAC CGC GAC CGC AAG ATC CTC CAA CTG TGC GGG GAA CTC         722
Ala Tyr Thr Asp Arg Asp Arg Lys Ile Leu Gln Leu Cys Gly Glu Leu
            225                 230                 235

TAC GAC CTG GAT GCC TCT TCC CTG CAG CTC AAA GTG CTC CAA TAC CTG         770
Tyr Asp Leu Asp Ala Ser Ser Leu Gln Leu Lys Val Leu Gln Tyr Leu
            240                 245                 250

CAG CAG GAG ACC CGG GCA TCC CGC TGC TGC CTC CTG CTG GTG TCG GAG         818
Gln Gln Glu Thr Arg Ala Ser Arg Cys Cys Leu Leu Leu Val Ser Glu
        255                 260                 265

GAC AAT CTC CAG CTT TCT TGC AAG GTC ATC GGA GAC AAA GTG CTC GGG         866
Asp Asn Leu Gln Leu Ser Cys Lys Val Ile Gly Asp Lys Val Leu Gly
270                 275                 280                 285

GAA GAG GTC AGC TTT CCC TTG ACA GGA TGC CTG GGC CAG GTG GTG GAA         914
Glu Glu Val Ser Phe Pro Leu Thr Gly Cys Leu Gly Gln Val Val Glu
                290                 295                 300

GAC AAG AAG TCC ATC CAG CTG AAG GAC CTC ACC TCC GAG GAT GTA CAA         962
Asp Lys Lys Ser Ile Gln Leu Lys Asp Leu Thr Ser Glu Asp Val Gln
            305                 310                 315

CAG CTG CAG AGC ATG TTG GGC TGT GAG CTG CAG GCC ATG CTC TGT GTC        1010
Gln Leu Gln Ser Met Leu Gly Cys Glu Leu Gln Ala Met Leu Cys Val
        320                 325                 330

CCT GTC ATC AGC CGG GCC ACT GAC CAG GTG GTG GCC TTG GCC TGC GCC        1058
Pro Val Ile Ser Arg Ala Thr Asp Gln Val Val Ala Leu Ala Cys Ala
        335                 340                 345

TTC AAC AAG CTA GAA GGA GAC TTG TTC ACC GAC GAG GAC GAG CAT GTG        1106
Phe Asn Lys Leu Glu Gly Asp Leu Phe Thr Asp Glu Asp Glu His Val
350                 355                 360                 365

ATC CAG CAC TGC TTC CAC TAC ACC AGC ACC GTG CTC ACC AGC ACC CTG        1154
Ile Gln His Cys Phe His Tyr Thr Ser Thr Val Leu Thr Ser Thr Leu
            370                 375                 380

GCC TTC CAG AAG GAA CAG AAA CTC AAG TGT GAG TGC CAG GCT CTT CTC        1202
Ala Phe Gln Lys Glu Gln Lys Leu Lys Cys Glu Cys Gln Ala Leu Leu
        385                 390                 395

CAA GTG GCA AAG AAC CTC TTC ACC CAC CTG GAT GAC GTC TCT GTC CTG        1250
Gln Val Ala Lys Asn Leu Phe Thr His Leu Asp Asp Val Ser Val Leu
            400                 405                 410

CTC CAG GAG ATC ATC ACG GAG GCC AGA AAC CTC AGC AAC GCA GAG ATC        1298
Leu Gln Glu Ile Ile Thr Glu Ala Arg Asn Leu Ser Asn Ala Glu Ile
        415                 420                 425

TGC TCT GTG TTC CTG CTG GAT CAG AAT GAG CTG GTG GCC AAG GTG TTC        1346
Cys Ser Val Phe Leu Leu Asp Gln Asn Glu Leu Val Ala Lys Val Phe
430                 435                 440                 445

GAC GGG GGC GTG GTG GAT GAT GAG AGC TAT GAG ATC CGC ATC CCG GCC        1394
Asp Gly Gly Val Val Asp Asp Glu Ser Tyr Glu Ile Arg Ile Pro Ala
            450                 455                 460
```

-continued

| | | |
|---|---|---|
| GAT CAG GGC ATC GCG GGA CAC GTG GCG ACC ACG GGC CAG ATC CTG AAC<br>Asp Gln Gly Ile Ala Gly His Val Ala Thr Thr Gly Gln Ile Leu Asn<br>                  465                            470                      475 | 1442 |
| ATC CCT GAC GCA TAT GCC CAT CCG CTT TTC TAC CGC GGC GTG GAC GAC<br>Ile Pro Asp Ala Tyr Ala His Pro Leu Phe Tyr Arg Gly Val Asp Asp<br>                      480                            485                      490 | 1490 |
| AGC ACC GGC TTC CGC ACG CGC AAC ATC CTC TGC TTC CCC ATC AAG AAC<br>Ser Thr Gly Phe Arg Thr Arg Asn Ile Leu Cys Phe Pro Ile Lys Asn<br>495                            500                            505 | 1538 |
| GAG AAC CAG GAG GTC ATC GGT GTG GCC GAG CTG GTG AAC AAG ATC AAT<br>Glu Asn Gln Glu Val Ile Gly Val Ala Glu Leu Val Asn Lys Ile Asn<br>510                            515                      520                      525 | 1586 |
| GGG CCA TGG TTC AGC AAG TTC GAC GAG GAC CTG GCG ACG GCC TTC TCC<br>Gly Pro Trp Phe Ser Lys Phe Asp Glu Asp Leu Ala Thr Ala Phe Ser<br>                        530                            535                      540 | 1634 |
| ATC TAC TGC GGC ATC AGC ATC GCC CAT TCT CTC CTA TAC AAA AAA GTG<br>Ile Tyr Cys Gly Ile Ser Ile Ala His Ser Leu Leu Tyr Lys Lys Val<br>                      545                            550                      555 | 1682 |
| AAT GAG GCT CAG TAT CGC AGC CAC CTG GCC AAT GAG ATG ATG ATG TAC<br>Asn Glu Ala Gln Tyr Arg Ser His Leu Ala Asn Glu Met Met Met Tyr<br>                560                            565                      570 | 1730 |
| CAC ATG AAG GTC TCC GAC GAT GAG TAT ACC AAA CTT CTC CAT GAT GGG<br>His Met Lys Val Ser Asp Asp Glu Tyr Thr Lys Leu Leu His Asp Gly<br>575                            580                            585 | 1778 |
| ATC CAG CCT GTG GCT GCC ATT GAC TCC AAT TTT GCA AGT TTC ACC TAT<br>Ile Gln Pro Val Ala Ala Ile Asp Ser Asn Phe Ala Ser Phe Thr Tyr<br>590                            595                      600                      605 | 1826 |
| ACC CCT CGT TCC CTG CCC GAG GAT GAC ACG TCC ATG GCC ATC CTG AGC<br>Thr Pro Arg Ser Leu Pro Glu Asp Asp Thr Ser Met Ala Ile Leu Ser<br>                        610                            615                      620 | 1874 |
| ATG CTG CAG GAC ATG AAT TTC ATC AAC AAC TAC AAA ATT GAC TGC CCG<br>Met Leu Gln Asp Met Asn Phe Ile Asn Asn Tyr Lys Ile Asp Cys Pro<br>                625                            630                      635 | 1922 |
| ACC CTG GCC CGG TTC TGT TTG ATG GTG AAG AAG GGC TAC CGG GAT CCC<br>Thr Leu Ala Arg Phe Cys Leu Met Val Lys Lys Gly Tyr Arg Asp Pro<br>                640                            645                      650 | 1970 |
| CCC TAC CAC AAC TGG ATG CAC GCC TTT TCT GTC TCC CAC TTC TGC TAC<br>Pro Tyr His Asn Trp Met His Ala Phe Ser Val Ser His Phe Cys Tyr<br>655                            660                            665 | 2018 |
| CTG CTC TAC AAG AAC CTG GAG CTC ACC AAC TAC CTC GAG GAC ATC GAG<br>Leu Leu Tyr Lys Asn Leu Glu Leu Thr Asn Tyr Leu Glu Asp Ile Glu<br>670                            675                      680                      685 | 2066 |
| ATC TTT GCC TTG TTT ATT TCC TGC ATG TGT CAT GAC CTG GAC CAC AGA<br>Ile Phe Ala Leu Phe Ile Ser Cys Met Cys His Asp Leu Asp His Arg<br>                        690                            695                      700 | 2114 |
| GGC ACA AAC AAC TCT TTC CAG GTG GCC TCG AAA TCT GTG CTG GCT GCG<br>Gly Thr Asn Asn Ser Phe Gln Val Ala Ser Lys Ser Val Leu Ala Ala<br>                      705                            710                      715 | 2162 |
| CTC TAC AGC TCT GAG GGC TCC GTC ATG GAG AGG CAC CAC TTT GCT CAG<br>Leu Tyr Ser Ser Glu Gly Ser Val Met Glu Arg His His Phe Ala Gln<br>                720                            725                      730 | 2210 |
| GCC ATC GCC ATC CTC AAC ACC CAC GGC TGC AAC ATC TTT GAT CAT TTC<br>Ala Ile Ala Ile Leu Asn Thr His Gly Cys Asn Ile Phe Asp His Phe<br>735                            740                            745 | 2258 |
| TCC CGG AAG GAC TAT CAG CGC ATG CTG GAT CTG ATG CGG GAC ATC ATC<br>Ser Arg Lys Asp Tyr Gln Arg Met Leu Asp Leu Met Arg Asp Ile Ile<br>750                            755                      760                      765 | 2306 |
| TTG GCC ACA GAC CTG GCC CAC CAT CTC CGC ATC TTC AAG GAC CTC CAG<br>Leu Ala Thr Asp Leu Ala His His Leu Arg Ile Phe Lys Asp Leu Gln<br>                      770                            775                      780 | 2354 |

```
AAG ATG GCT GAG GTG GGC TAC GAC CGA AAC AAC AAG CAG CAC CAC AGA        2402
Lys Met Ala Glu Val Gly Tyr Asp Arg Asn Asn Lys Gln His His Arg
            785                 790                 795

CTT CTC CTC TGC CTC CTC ATG ACC TCC TGT GAC CTC TCT GAC CAG ACC        2450
Leu Leu Leu Cys Leu Leu Met Thr Ser Cys Asp Leu Ser Asp Gln Thr
            800                 805                 810

AAG GGC TGG AAG ACT ACG AGA AAG ATC GCG GAG CTG ATC TAC AAA GAA        2498
Lys Gly Trp Lys Thr Thr Arg Lys Ile Ala Glu Leu Ile Tyr Lys Glu
            815                 820                 825

TTC TTC TCC CAG GGA GAC CTG GAG AAG GCC ATG GGC AAC AGG CCG ATG        2546
Phe Phe Ser Gln Gly Asp Leu Glu Lys Ala Met Gly Asn Arg Pro Met
830                 835                 840                 845

GAG ATG ATG GAC CGG GAG AAG GCC TAT ATC CCT GAG CTG CAA ATC AGC        2594
Glu Met Met Asp Arg Glu Lys Ala Tyr Ile Pro Glu Leu Gln Ile Ser
            850                 855                 860

TTC ATG GAG CAC ATT GCA ATG CCC ATC TAC AAG CTG TTG CAG GAC CTG        2642
Phe Met Glu His Ile Ala Met Pro Ile Tyr Lys Leu Leu Gln Asp Leu
            865                 870                 875

TTC CCC AAA GCG GCA GAG CTG TAC GAG CGC GTG GCC TCC AAC CGT GAG        2690
Phe Pro Lys Ala Ala Glu Leu Tyr Glu Arg Val Ala Ser Asn Arg Glu
            880                 885                 890

CAC TGG ACC AAG GTG TCC CAC AAG TTC ACC ATC CGC GGC CTC CCA AGT        2738
His Trp Thr Lys Val Ser His Lys Phe Thr Ile Arg Gly Leu Pro Ser
            895                 900                 905

AAC AAC TCG CTG GAC TTC CTG GAT GAG GAG TAC GAG GTG CCT GAT CTG        2786
Asn Asn Ser Leu Asp Phe Leu Asp Glu Glu Tyr Glu Val Pro Asp Leu
910                 915                 920                 925

GAT GGC ACT AGG GCC CCC ATC AAT GGC TGC TGC AGC CTT GAT GCT GAG        2834
Asp Gly Thr Arg Ala Pro Ile Asn Gly Cys Cys Ser Leu Asp Ala Glu
            930                 935                 940

TGACTCGAGC GTCATATTAA TGGACGCAAA GCAAGGAAAT TGCGAGCGGG AAATAAGAAA     2894

CGATAGAAGT AGGAATCGAT ACCCGGTGCG TGCACATAAC AGTCTTTTAC CAATTAACAG     2954

GAGAGATTGA AGTGTCGAGA TACGAAATGA AATTTACTAC GACTACCGTA AAGAAATGCA     3014

TAAGCTCTGT TAGAGAAAAA TTGGTAGCCA                                      3044

(2) INFORMATION FOR SEQ ID NO:45:

(i) SEQUENCE CHARACTERISTICS:
        (A) LENGTH: 941 amino acids
        (B) TYPE: amino acid
        (D) TOPOLOGY: linear (ii) MOLECULE TYPE: protein (xi) SEQUENCE DESCRIPTION: SEQ ID NO:45:

Met Gly Gln Ala Cys Gly His Ser Ile Leu Cys Arg Ser Gln Gln Tyr
1               5                   10                  15

Pro Ala Ala Arg Pro Ala Glu Pro Arg Gly Gln Val Phe Leu Lys
                20                  25                  30

Pro Asp Glu Pro Pro Pro Gln Pro Cys Ala Asp Ser Leu Gln
            35                  40                  45

Asp Ala Leu Leu Ser Leu Gly Ser Val Ile Asp Ile Ser Gly Leu Gln
            50                  55                  60

Arg Ala Val Lys Glu Ala Leu Ser Ala Val Leu Pro Arg Val Glu Thr
65                  70                  75                  80

Val Tyr Thr Tyr Leu Leu Asp Gly Glu Ser Gln Leu Val Cys Glu Asp
                85                  90                  95

Pro Pro His Glu Leu Pro Gln Glu Gly Lys Val Arg Glu Ala Ile Ile
```

```
              100                 105                 110
Ser Gln Lys Arg Leu Gly Cys Asn Gly Leu Gly Phe Ser Asp Leu Pro
            115                 120                 125

Gly Lys Pro Leu Ala Arg Leu Val Ala Pro Leu Ala Pro Asp Thr Gln
130                 135                 140

Val Leu Val Met Pro Leu Ala Asp Lys Glu Ala Gly Ala Val Ala Ala
145                 150                 155                 160

Val Ile Leu Val His Cys Gly Gln Leu Ser Asp Asn Glu Glu Trp Ser
                165                 170                 175

Leu Gln Ala Val Glu Lys His Thr Leu Val Ala Leu Arg Arg Val Gln
            180                 185                 190

Val Leu Gln Gln Arg Gly Pro Arg Glu Ala Pro Arg Ala Val Gln Asn
            195                 200                 205

Pro Pro Glu Gly Thr Ala Glu Asp Gln Lys Gly Gly Ala Ala Tyr Thr
210                 215                 220

Asp Arg Asp Arg Lys Ile Leu Gln Leu Cys Gly Glu Leu Tyr Asp Leu
225                 230                 235                 240

Asp Ala Ser Ser Leu Gln Leu Lys Val Leu Gln Tyr Leu Gln Gln Glu
                245                 250                 255

Thr Arg Ala Ser Arg Cys Cys Leu Leu Leu Val Ser Glu Asp Asn Leu
            260                 265                 270

Gln Leu Ser Cys Lys Val Ile Gly Asp Lys Val Leu Gly Glu Glu Val
            275                 280                 285

Ser Phe Pro Leu Thr Gly Cys Leu Gly Gln Val Val Glu Asp Lys Lys
            290                 295                 300

Ser Ile Gln Leu Lys Asp Leu Thr Ser Glu Asp Val Gln Gln Leu Gln
305                 310                 315                 320

Ser Met Leu Gly Cys Glu Leu Gln Ala Met Leu Cys Val Pro Val Ile
                325                 330                 335

Ser Arg Ala Thr Asp Gln Val Val Ala Leu Ala Cys Ala Phe Asn Lys
            340                 345                 350

Leu Glu Gly Asp Leu Phe Thr Asp Glu Asp Glu His Val Ile Gln His
            355                 360                 365

Cys Phe His Tyr Thr Ser Thr Val Leu Thr Ser Thr Leu Ala Phe Gln
            370                 375                 380

Lys Glu Gln Lys Leu Lys Cys Glu Cys Gln Ala Leu Leu Gln Val Ala
385                 390                 395                 400

Lys Asn Leu Phe Thr His Leu Asp Asp Val Ser Val Leu Leu Gln Glu
                405                 410                 415

Ile Ile Thr Glu Ala Arg Asn Leu Ser Asn Ala Glu Ile Cys Ser Val
            420                 425                 430

Phe Leu Leu Asp Gln Asn Glu Leu Val Ala Lys Val Phe Asp Gly Gly
            435                 440                 445

Val Val Asp Asp Glu Ser Tyr Glu Ile Arg Ile Pro Ala Asp Gln Gly
450                 455                 460

Ile Ala Gly His Val Ala Thr Thr Gly Gln Ile Leu Asn Ile Pro Asp
465                 470                 475                 480

Ala Tyr Ala His Pro Leu Phe Tyr Arg Gly Val Asp Asp Ser Thr Gly
                485                 490                 495

Phe Arg Thr Arg Asn Ile Leu Cys Phe Pro Ile Lys Asn Glu Asn Gln
            500                 505                 510

Glu Val Ile Gly Val Ala Glu Leu Val Asn Lys Ile Asn Gly Pro Trp
            515                 520                 525
```

```
Phe Ser Lys Phe Asp Glu Asp Leu Ala Thr Ala Phe Ser Ile Tyr Cys
    530                 535                 540
Gly Ile Ser Ile Ala His Ser Leu Leu Tyr Lys Lys Val Asn Glu Ala
545                 550                 555                 560
Gln Tyr Arg Ser His Leu Ala Asn Glu Met Met Tyr His Met Lys
                565                 570                 575
Val Ser Asp Asp Glu Tyr Thr Lys Leu Leu His Asp Gly Ile Gln Pro
            580                 585                 590
Val Ala Ala Ile Asp Ser Asn Phe Ala Ser Phe Thr Tyr Thr Pro Arg
        595                 600                 605
Ser Leu Pro Glu Asp Asp Thr Ser Met Ala Ile Leu Ser Met Leu Gln
    610                 615                 620
Asp Met Asn Phe Ile Asn Asn Tyr Lys Ile Asp Cys Pro Thr Leu Ala
625                 630                 635                 640
Arg Phe Cys Leu Met Val Lys Lys Gly Tyr Arg Asp Pro Pro Tyr His
                645                 650                 655
Asn Trp Met His Ala Phe Ser Val Ser His Phe Cys Tyr Leu Leu Tyr
            660                 665                 670
Lys Asn Leu Glu Leu Thr Asn Tyr Leu Glu Asp Ile Glu Ile Phe Ala
        675                 680                 685
Leu Phe Ile Ser Cys Met Cys His Asp Leu Asp His Arg Gly Thr Asn
    690                 695                 700
Asn Ser Phe Gln Val Ala Ser Lys Ser Val Leu Ala Ala Leu Tyr Ser
705                 710                 715                 720
Ser Glu Gly Ser Val Met Glu Arg His His Phe Ala Gln Ala Ile Ala
                725                 730                 735
Ile Leu Asn Thr His Gly Cys Asn Ile Phe Asp His Phe Ser Arg Lys
            740                 745                 750
Asp Tyr Gln Arg Met Leu Asp Leu Met Arg Asp Ile Ile Leu Ala Thr
        755                 760                 765
Asp Leu Ala His His Leu Arg Ile Phe Lys Asp Leu Gln Lys Met Ala
    770                 775                 780
Glu Val Gly Tyr Asp Arg Asn Asn Lys Gln His His Arg Leu Leu Leu
785                 790                 795                 800
Cys Leu Leu Met Thr Ser Cys Asp Leu Ser Asp Gln Thr Lys Gly Trp
                805                 810                 815
Lys Thr Thr Arg Lys Ile Ala Glu Leu Ile Tyr Lys Glu Phe Phe Ser
            820                 825                 830
Gln Gly Asp Leu Glu Lys Ala Met Gly Asn Arg Pro Met Glu Met Met
        835                 840                 845
Asp Arg Glu Lys Ala Tyr Ile Pro Glu Leu Gln Ile Ser Phe Met Glu
    850                 855                 860
His Ile Ala Met Pro Ile Tyr Lys Leu Leu Gln Asp Leu Phe Pro Lys
865                 870                 875                 880
Ala Ala Glu Leu Tyr Glu Arg Val Ala Ser Asn Arg Glu His Trp Thr
                885                 890                 895
Lys Val Ser His Lys Phe Thr Ile Arg Gly Leu Pro Ser Asn Asn Ser
            900                 905                 910
Leu Asp Phe Leu Asp Glu Glu Tyr Glu Val Pro Asp Leu Asp Gly Thr
        915                 920                 925
Arg Ala Pro Ile Asn Gly Cys Cys Ser Leu Asp Ala Glu
    930                 935                 940

(2) INFORMATION FOR SEQ ID NO:46:
```

(i) SEQUENCE CHARACTERISTICS:
    (A) LENGTH: 23 base pairs
    (B) TYPE: nucleic acid
    (C) STRANDEDNESS: single
    (D) TOPOLOGY: linear (ii) MOLECULE TYPE: DNA (iv) ANTI-SENSE: YES (xi) SEQUENCE DESCRIPTION: SEQ ID NO:46:

TCRTTNGTNG TNCCYTTCAT RTT                                        23

(2) INFORMATION FOR SEQ ID NO:47:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:47:

Asn Met Lys Gly Thr Thr Asn Asp
1               5

(2) INFORMATION FOR SEQ ID NO:48:

(i) SEQUENCE CHARACTERISTICS:
        (A) LENGTH: 1625 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 12..1616

(xi) SEQUENCE DESCRIPTION: SEQ ID NO:48:

```
GAATTCTGAT C ATG GGG TCT AGT GCC ACA GAG ATT GAA GAA TTG GAA AAC        50
            Met Gly Ser Ser Ala Thr Glu Ile Glu Glu Leu Glu Asn
             1               5                  10

ACC ACT TTT AAG TAT CTT ACA GGA GAA CAG ACT GAA AAA ATG TGG CAG         98
Thr Thr Phe Lys Tyr Leu Thr Gly Glu Gln Thr Glu Lys Met Trp Gln
 15                  20                  25

CGC CTG AAA GGA ATA CTA AGA TGC TTG GTG AAG CAG CTG GAA AGA GGT        146
Arg Leu Lys Gly Ile Leu Arg Cys Leu Val Lys Gln Leu Glu Arg Gly
 30                  35                  40                  45

GAT GTT AAC GTC GTC GAC TTA AAG AAG AAT ATT GAA TAT GCG GCA TCT        194
Asp Val Asn Val Val Asp Leu Lys Lys Asn Ile Glu Tyr Ala Ala Ser
                 50                  55                  60

GTG CTG GAA GCA GTT TAT ATC GAT GAA ACA AGA AGA CTT CTG GAT ACT        242
Val Leu Glu Ala Val Tyr Ile Asp Glu Thr Arg Arg Leu Leu Asp Thr
                 65                  70                  75

GAA GAT GAG CTC AGT GAC ATT CAG ACT GAC TCA GTC CCA TCT GAA GTC        290
Glu Asp Glu Leu Ser Asp Ile Gln Thr Asp Ser Val Pro Ser Glu Val
             80                  85                  90

CGG GAC TGG TTG GCT TCT ACC TTT ACA CGG AAA ATG GGG ATG ACA AAA        338
Arg Asp Trp Leu Ala Ser Thr Phe Thr Arg Lys Met Gly Met Thr Lys
         95                  100                 105

AAG AAA CCT GAG GAA AAA CCA AAA TTT CGG AGC ATT GTG CAT GCT GTT        386
Lys Lys Pro Glu Glu Lys Pro Lys Phe Arg Ser Ile Val His Ala Val
110                 115                 120                 125

CAA GCT GGA ATT TTT GTG GAA AGA ATG TAC CGA AAA ACA TAT CAT ATG        434
```

-continued

```
                Gln Ala Gly Ile Phe Val Glu Arg Met Tyr Arg Lys Thr Tyr His Met
                                    130                 135                 140

GTT GGT TTG GCA TAT CCA GCA GCT GTC ATC GTA ACA TTA AAG GAT GTT                482
Val Gly Leu Ala Tyr Pro Ala Ala Val Ile Val Thr Leu Lys Asp Val
            145                 150                 155

GAT AAA TGG TCT TTC GAT GTA TTT GCC CTA AAT GAA GCA AGT GGA GAG                530
Asp Lys Trp Ser Phe Asp Val Phe Ala Leu Asn Glu Ala Ser Gly Glu
        160                 165                 170

CAT AGT CTG AAG TTT ATG ATT TAT GAA CTG TTT ACC AGA TAT GAT CTT                578
His Ser Leu Lys Phe Met Ile Tyr Glu Leu Phe Thr Arg Tyr Asp Leu
    175                 180                 185

ATC AAC CGT TTC AAG ATT CCT GTT TCT TGC CTA ATC ACC TTT GCA GAA                626
Ile Asn Arg Phe Lys Ile Pro Val Ser Cys Leu Ile Thr Phe Ala Glu
190                 195                 200                 205

GCT TTA GAA GTT GGT TAC AGC AAG TAC AAA AAT CCA TAT CAC AAT TTG                674
Ala Leu Glu Val Gly Tyr Ser Lys Tyr Lys Asn Pro Tyr His Asn Leu
                210                 215                 220

ATT CAT GCA GCT GAT GTC ACT CAA ACT GTG CAT TAC ATA ATG CTT CAT                722
Ile His Ala Ala Asp Val Thr Gln Thr Val His Tyr Ile Met Leu His
            225                 230                 235

ACA GGT ATC ATG CAC TGG CTC ACT GAA CTG GAA ATT TTA GCA ATG GTC                770
Thr Gly Ile Met His Trp Leu Thr Glu Leu Glu Ile Leu Ala Met Val
        240                 245                 250

TTT GCT GCT GCC ATT CAT GAT TAT GAG CAT ACA GGG ACA ACA AAC AAC                818
Phe Ala Ala Ala Ile His Asp Tyr Glu His Thr Gly Thr Thr Asn Asn
    255                 260                 265

TTT CAC ATT CAG ACA AGG TCA GAT GTT GCC ATT TTG TAT AAT GAT CGC                866
Phe His Ile Gln Thr Arg Ser Asp Val Ala Ile Leu Tyr Asn Asp Arg
270                 275                 280                 285

TCT GTC CTT GAG AAT CAC CAC GTG AGT GCA GCT TAT CGA CTT ATG CAA                914
Ser Val Leu Glu Asn His His Val Ser Ala Ala Tyr Arg Leu Met Gln
                290                 295                 300

GAA GAA GAA ATG AAT ATC TTG ATA AAT TTA TCC AAA GAT GAC TGG AGG                962
Glu Glu Glu Met Asn Ile Leu Ile Asn Leu Ser Lys Asp Asp Trp Arg
            305                 310                 315

GAT CTT CGG AAC CTA GTG ATT GAA ATG GTT TTA TCT ACA GAC ATG TCA               1010
Asp Leu Arg Asn Leu Val Ile Glu Met Val Leu Ser Thr Asp Met Ser
        320                 325                 330

GGT CAC TTC CAG CAA ATT AAA AAT ATA AGA AAC AGT TTG CAG CAG CCT               1058
Gly His Phe Gln Gln Ile Lys Asn Ile Arg Asn Ser Leu Gln Gln Pro
    335                 340                 345

GAA GGG ATT GAC AGA GCC AAA ACC ATG TCC CTG ATT CTC CAC GCA GCA               1106
Glu Gly Ile Asp Arg Ala Lys Thr Met Ser Leu Ile Leu His Ala Ala
350                 355                 360                 365

GAC ATC AGC CAC CCA GCC AAA TCC TGG AAG CTG CAT TAT CGG TGG ACC               1154
Asp Ile Ser His Pro Ala Lys Ser Trp Lys Leu His Tyr Arg Trp Thr
                370                 375                 380

ATG GCC CTA ATG GAG GAG TTT TTC CTG CAG GGA GAT AAA GAA GCT GAA               1202
Met Ala Leu Met Glu Glu Phe Phe Leu Gln Gly Asp Lys Glu Ala Glu
            385                 390                 395

TTA GGG CTT CCA TTT TCC CCA CTT TGT GAT CGG AAG TCA ACC ATG GTG               1250
Leu Gly Leu Pro Phe Ser Pro Leu Cys Asp Arg Lys Ser Thr Met Val
        400                 405                 410

GCC CAG TCA CAA ATA GGT TTC ATC GAT TTC ATA GTA GAG CCA ACA TTT               1298
Ala Gln Ser Gln Ile Gly Phe Ile Asp Phe Ile Val Glu Pro Thr Phe
    415                 420                 425

TCT CTT CTG ACA GAC TCA ACA GAG AAA ATT GTT ATT CCT CTT ATA GAG               1346
Ser Leu Leu Thr Asp Ser Thr Glu Lys Ile Val Ile Pro Leu Ile Glu
430                 435                 440                 445

GAA GCC TCA AAA GCC GAA ACT TCT TCC TAT GTG GCA AGC AGC TCA ACC               1394
Glu Ala Ser Lys Ala Glu Thr Ser Ser Tyr Val Ala Ser Ser Ser Thr
```

```
Glu Ala Ser Lys Ala Glu Thr Ser Ser Tyr Val Ala Ser Ser Ser Thr
                450                 455                 460

ACC ATT GTG GGG TTA CAC ATT GCT GAT GCA CTA AGA CGA TCA AAT ACA       1442
Thr Ile Val Gly Leu His Ile Ala Asp Ala Leu Arg Arg Ser Asn Thr
            465                 470                 475

AAA GGC TCC ATG AGT GAT GGG TCC TAT TCC CCA GAC TAC TCC CTT GCA       1490
Lys Gly Ser Met Ser Asp Gly Ser Tyr Ser Pro Asp Tyr Ser Leu Ala
                480                 485                 490

GCA GTG GAC CTG AAG AGT TTC AAG AAC AAC CTG GTG GAC ATC ATT CAG       1538
Ala Val Asp Leu Lys Ser Phe Lys Asn Asn Leu Val Asp Ile Ile Gln
        495                 500                 505

CAG AAC AAA GAG AGG TGG AAA GAG TTA GCT GCA CAA GAA GCA AGA ACC       1586
Gln Asn Lys Glu Arg Trp Lys Glu Leu Ala Ala Gln Glu Ala Arg Thr
510                 515                 520                 525

AGT TCA CAG AAG TGT GAG TTT ATT CAT CAG TAACTCGAG                     1625
Ser Ser Gln Lys Cys Glu Phe Ile His Gln
                530                 535

(2) INFORMATION FOR SEQ ID NO:49:

(i) SEQUENCE CHARACTERISTICS:
        (A) LENGTH: 535 amino acids
        (B) TYPE: amino acid
        (D) TOPOLOGY: linear (ii) MOLECULE TYPE: protein (xi) SEQUENCE DESCRIPTION: SEQ ID NO:49:

Met Gly Ser Ser Ala Thr Glu Ile Glu Glu Leu Glu Asn Thr Thr Phe
  1               5                  10                  15

Lys Tyr Leu Thr Gly Glu Gln Thr Glu Lys Met Trp Gln Arg Leu Lys
             20                  25                  30

Gly Ile Leu Arg Cys Leu Val Lys Gln Leu Glu Arg Gly Asp Val Asn
         35                  40                  45

Val Val Asp Leu Lys Lys Asn Ile Glu Tyr Ala Ala Ser Val Leu Glu
     50                  55                  60

Ala Val Tyr Ile Asp Glu Thr Arg Arg Leu Leu Asp Thr Glu Asp Glu
 65                  70                  75                  80

Leu Ser Asp Ile Gln Thr Asp Ser Val Pro Ser Glu Val Arg Asp Trp
             85                  90                  95

Leu Ala Ser Thr Phe Thr Arg Lys Met Gly Met Thr Lys Lys Lys Pro
            100                 105                 110

Glu Glu Lys Pro Lys Phe Arg Ser Ile Val His Ala Val Gln Ala Gly
        115                 120                 125

Ile Phe Val Glu Arg Met Tyr Arg Lys Thr Tyr His Met Val Gly Leu
    130                 135                 140

Ala Tyr Pro Ala Ala Val Ile Val Thr Leu Lys Asp Val Asp Lys Trp
145                 150                 155                 160

Ser Phe Asp Val Phe Ala Leu Asn Glu Ala Ser Gly Glu His Ser Leu
                165                 170                 175

Lys Phe Met Ile Tyr Glu Leu Phe Thr Arg Tyr Asp Leu Ile Asn Arg
            180                 185                 190

Phe Lys Ile Pro Val Ser Cys Leu Ile Thr Phe Ala Glu Ala Leu Glu
        195                 200                 205

Val Gly Tyr Ser Lys Tyr Lys Asn Pro Tyr His Asn Leu Ile His Ala
    210                 215                 220

Ala Asp Val Thr Gln Thr Val His Tyr Ile Met Leu His Thr Gly Ile
225                 230                 235                 240
```

-continued

```
Met His Trp Leu Thr Glu Leu Glu Ile Leu Ala Met Val Phe Ala Ala
            245                 250                 255

Ala Ile His Asp Tyr Glu His Thr Gly Thr Thr Asn Asn Phe His Ile
            260                 265                 270

Gln Thr Arg Ser Asp Val Ala Ile Leu Tyr Asn Asp Arg Ser Val Leu
            275                 280                 285

Glu Asn His His Val Ser Ala Ala Tyr Arg Leu Met Gln Glu Glu Glu
            290                 295                 300

Met Asn Ile Leu Ile Asn Leu Ser Lys Asp Asp Trp Arg Asp Leu Arg
305                 310                 315                 320

Asn Leu Val Ile Glu Met Val Leu Ser Thr Asp Met Ser Gly His Phe
            325                 330                 335

Gln Gln Ile Lys Asn Ile Arg Asn Ser Leu Gln Gln Pro Glu Gly Ile
            340                 345                 350

Asp Arg Ala Lys Thr Met Ser Leu Ile Leu His Ala Ala Asp Ile Ser
            355                 360                 365

His Pro Ala Lys Ser Trp Lys Leu His Tyr Arg Trp Thr Met Ala Leu
            370                 375                 380

Met Glu Glu Phe Phe Leu Gln Gly Asp Lys Glu Ala Glu Leu Gly Leu
385                 390                 395                 400

Pro Phe Ser Pro Leu Cys Asp Arg Lys Ser Thr Met Val Ala Gln Ser
            405                 410                 415

Gln Ile Gly Phe Ile Asp Phe Ile Val Glu Pro Thr Phe Ser Leu Leu
            420                 425                 430

Thr Asp Ser Thr Glu Lys Ile Val Ile Pro Leu Ile Glu Glu Ala Ser
            435                 440                 445

Lys Ala Glu Thr Ser Ser Tyr Val Ala Ser Ser Thr Thr Ile Val
450                 455                 460

Gly Leu His Ile Ala Asp Ala Leu Arg Arg Ser Asn Thr Lys Gly Ser
465                 470                 475                 480

Met Ser Asp Gly Ser Tyr Ser Pro Asp Tyr Ser Leu Ala Ala Val Asp
            485                 490                 495

Leu Lys Ser Phe Lys Asn Asn Leu Val Asp Ile Ile Gln Gln Asn Lys
            500                 505                 510

Glu Arg Trp Lys Glu Leu Ala Ala Gln Glu Ala Arg Thr Ser Ser Gln
            515                 520                 525

Lys Cys Glu Phe Ile His Gln
            530                 535
```

(2) INFORMATION FOR SEQ ID NO:50:

(i) SEQUENCE CHARACTERISTICS:
        (A) LENGTH: 2693 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 176..2077

(xi) SEQUENCE DESCRIPTION: SEQ ID NO:50:

```
GTCGCTTCAA TATTTCAAAA TGGATCCGGT TCTGTGGCGG GTGCGAGAGT GAGGCTGTGG      60

GGGACCTCCA GGCCGAACCT CCGCGAAGCC TCGGCCTTCT GCGTGCCCTG GCCCCGGGAG    120

GATAAGGATT TCCCTTCCCT CCTACTTGCG CGCGGAGCCG AGCTCTTGTT GAGCT ATG     178
                                                              Met
```

```
                                                    1
GAG TCG CCA ACC AAG GAG ATT GAA GAA TTT GAG AGC AAC TCT CTG AAA       226
Glu Ser Pro Thr Lys Glu Ile Glu Glu Phe Glu Ser Asn Ser Leu Lys
            5                  10                  15

TAC CTG CAA CCG GAA CAG ATC GAG AAA ATC TGG CTT CGG CTC CGC GGG       274
Tyr Leu Gln Pro Glu Gln Ile Glu Lys Ile Trp Leu Arg Leu Arg Gly
         20                  25                  30

CTG AGG AAA TAT AAG AAA ACG TCC CAG AGA TTA CGG TCT TTG GTC AAA       322
Leu Arg Lys Tyr Lys Lys Thr Ser Gln Arg Leu Arg Ser Leu Val Lys
     35                  40                  45

CAA TTA GAG AGA GGG GAA GCT TCA GTG GTA GAT CTT AAG AAG AAT TTG       370
Gln Leu Glu Arg Gly Glu Ala Ser Val Val Asp Leu Lys Lys Asn Leu
 50              55                  60                  65

GAA TAT GCA GCC ACA GTG CTT GAA TCT GTG TAT ATT GAT GAA ACA AGG       418
Glu Tyr Ala Ala Thr Val Leu Glu Ser Val Tyr Ile Asp Glu Thr Arg
                 70                  75                  80

AGA CTC CTG GAT ACA GAG GAT GAG CTC AGT GAC ATT CAG TCA GAT GCT       466
Arg Leu Leu Asp Thr Glu Asp Glu Leu Ser Asp Ile Gln Ser Asp Ala
             85                  90                  95

GTG CCT TCT GAG GTC CGA GAC TGG CTG GCC TCC ACC TTC ACG CGG CAG       514
Val Pro Ser Glu Val Arg Asp Trp Leu Ala Ser Thr Phe Thr Arg Gln
         100                 105                 110

ATG GGG ATG ATG CTC AGG AGG AGC GAC GAG AAG CCC CGG TTC AAG AGC       562
Met Gly Met Met Leu Arg Arg Ser Asp Glu Lys Pro Arg Phe Lys Ser
     115                 120                 125

ATC GTT CAC GCA GTG CAG GCT GGG ATA TTT GTG GAG AGA ATG TAT AGA       610
Ile Val His Ala Val Gln Ala Gly Ile Phe Val Glu Arg Met Tyr Arg
130                 135                 140                 145

CGG ACA TCA AAC ATG GTT GGA CTG AGC TAT CCA CCA GCT GTT ATT GAG       658
Arg Thr Ser Asn Met Val Gly Leu Ser Tyr Pro Pro Ala Val Ile Glu
                150                 155                 160

GCA TTA AAG GAT GTG GAC AAG TGG TCC TTT GAC GTC TTT TCC CTC AAT       706
Ala Leu Lys Asp Val Asp Lys Trp Ser Phe Asp Val Phe Ser Leu Asn
            165                 170                 175

GAG GCC AGT GGG GAT CAT GCA CTG AAA TTT ATT TTC TAT GAA CTA CTC       754
Glu Ala Ser Gly Asp His Ala Leu Lys Phe Ile Phe Tyr Glu Leu Leu
        180                 185                 190

ACA CGT TAT GAT CTG ATC AGC CGT TTC AAG ATC CCC ATT TCT GCA CTT       802
Thr Arg Tyr Asp Leu Ile Ser Arg Phe Lys Ile Pro Ile Ser Ala Leu
    195                 200                 205

GTC TCA TTT GTG GAG GCC CTG GAA GTG GGA TAC AGC AAG CAC AAA AAT       850
Val Ser Phe Val Glu Ala Leu Glu Val Gly Tyr Ser Lys His Lys Asn
210                 215                 220                 225

CCT TAC CAT AAC TTA ATG CAC GCT GCC GAT GTT ACA CAG ACA GTG CAT       898
Pro Tyr His Asn Leu Met His Ala Ala Asp Val Thr Gln Thr Val His
                230                 235                 240

TAC CTC CTC TAT AAG ACA GGA GTG GCG AAC TGG CTG ACG GAG CTG GAG       946
Tyr Leu Leu Tyr Lys Thr Gly Val Ala Asn Trp Leu Thr Glu Leu Glu
            245                 250                 255

ATC TTT GCT ATA ATC TTC TCA GCT GCC ATC CAT GAC TAC GAG CAT ACC       994
Ile Phe Ala Ile Ile Phe Ser Ala Ala Ile His Asp Tyr Glu His Thr
        260                 265                 270

GGA ACC ACC AAC AAT TTC CAC ATT CAG ACT CGG TCT GAT CCA GCT ATT       1042
Gly Thr Thr Asn Asn Phe His Ile Gln Thr Arg Ser Asp Pro Ala Ile
    275                 280                 285

CTG TAT AAT GAC AGA TCT GTA CTG GAG AAT CAC CAT TTA AGT GCA GCT       1090
Leu Tyr Asn Asp Arg Ser Val Leu Glu Asn His His Leu Ser Ala Ala
290                 295                 300                 305

TAT CGC CTT CTG CAA GAT GAC GAG GAA ATG AAT ATT TTG ATT AAC CTC       1138
Tyr Arg Leu Leu Gln Asp Asp Glu Glu Met Asn Ile Leu Ile Asn Leu
```

-continued

|  |  |  | 310 |  |  |  | 315 |  |  |  | 320 |  |  |  |
|---|---|---|---|---|---|---|---|---|---|---|---|---|---|---|
| TCA | AAG | GAT | GAC | TGG | AGG | GAG | TTT | CGA | ACC | TTG | GTA | ATT | GAA | ATG GTG | 1186 |
| Ser | Lys | Asp | Asp | Trp | Arg | Glu | Phe | Arg | Thr | Leu | Val | Ile | Glu | Met Val |
|  |  |  | 325 |  |  |  | 330 |  |  |  | 335 |  |  |  |

```
          310                        315                         320
TCA AAG GAT GAC TGG AGG GAG TTT CGA ACC TTG GTA ATT GAA ATG GTG        1186
Ser Lys Asp Asp Trp Arg Glu Phe Arg Thr Leu Val Ile Glu Met Val
            325                330                 335

ATG GCC ACA GAT ATG TCT TGT CAC TTC CAA CAA ATC AAA GCA ATG AAG        1234
Met Ala Thr Asp Met Ser Cys His Phe Gln Gln Ile Lys Ala Met Lys
            340                345                 350

ACT GCT CTG CAG CAG CCA GAA GCC ATT GAA AAG CCA AAA GCC TTA TCC        1282
Thr Ala Leu Gln Gln Pro Glu Ala Ile Glu Lys Pro Lys Ala Leu Ser
            355                360                 365

CTT ATG CTG CAT ACA GCA GAT ATT AGC CAT CCA GCA AAA GCA TGG GAC        1330
Leu Met Leu His Thr Ala Asp Ile Ser His Pro Ala Lys Ala Trp Asp
370             375                380                      385

CTC CAT CAT CGC TGG ACA ATG TCA CTC CTG GAG GAG TTC TTC AGA CAG        1378
Leu His His Arg Trp Thr Met Ser Leu Leu Glu Glu Phe Phe Arg Gln
                390                395                      400

GGT GAC AGA GAA GCA GAG CTG GGG CTG CCT TTT TCT CCT CTG TGT GAC        1426
Gly Asp Arg Glu Ala Glu Leu Gly Leu Pro Phe Ser Pro Leu Cys Asp
                405                410                      415

CGA AAG TCC ACT ATG GTT GCT CAG TCA CAA GTA GGT TTC ATT GAT TTC        1474
Arg Lys Ser Thr Met Val Ala Gln Ser Gln Val Gly Phe Ile Asp Phe
                420                425                      430

ATC GTG GAA CCC ACC TTC ACT GTG CTT ACG GAC ATG ACC GAG AAG ATT        1522
Ile Val Glu Pro Thr Phe Thr Val Leu Thr Asp Met Thr Glu Lys Ile
435                 440                445

GTG AGT CCA TTA ATC GAT GAA ACC TCT CAA ACT GGT GGG ACA GGA CAG        1570
Val Ser Pro Leu Ile Asp Glu Thr Ser Gln Thr Gly Gly Thr Gly Gln
450                 455                460                      465

AGG CGT TCG AGT TTG AAT AGC ATC AGC TCG TCA GAT GCC AAG CGA TCA        1618
Arg Arg Ser Ser Leu Asn Ser Ile Ser Ser Ser Asp Ala Lys Arg Ser
                470                475                      480

GGT GTC AAG ACC TCT GGT TCA GAG GGA AGT GCC CCG ATC AAC AAT TCT        1666
Gly Val Lys Thr Ser Gly Ser Glu Gly Ser Ala Pro Ile Asn Asn Ser
                485                490                      495

GTC ATC TCC GTT GAC TAT AAG AGC TTT AAA GCT ACT TGG ACG GAA GTG        1714
Val Ile Ser Val Asp Tyr Lys Ser Phe Lys Ala Thr Trp Thr Glu Val
                500                505                      510

GTG CAC ATC AAT CGG GAG AGA TGG AGG GCC AAG GTA CCC AAA GAG GAG        1762
Val His Ile Asn Arg Glu Arg Trp Arg Ala Lys Val Pro Lys Glu Glu
515                 520                525

AAG GCC AAG AAG GAA GCA GAG GAA AAG GCT CGC CTG GCC GCA GAG GAG        1810
Lys Ala Lys Lys Glu Ala Glu Glu Lys Ala Arg Leu Ala Ala Glu Glu
530                 535                540                      545

CAG CAA AAG GAA ATG GAA GCC AAA AGC CAG GCT GAA GAA GGC GCA TCT        1858
Gln Gln Lys Glu Met Glu Ala Lys Ser Gln Ala Glu Glu Gly Ala Ser
                550                555                      560

GGC AAA GCT GAG AAA AAG ACG TCT GGA GAA ACT AAG AAT CAA GTC AAT        1906
Gly Lys Ala Glu Lys Lys Thr Ser Gly Glu Thr Lys Asn Gln Val Asn
                565                570                      575

GGA ACA CGG GCA AAC AAA AGT GAC AAC CCT CGT GGG AAA AAT TCC AAA        1954
Gly Thr Arg Ala Asn Lys Ser Asp Asn Pro Arg Gly Lys Asn Ser Lys
                580                585                      590

GCC GAG AAG TCA TCA GGA GAA CAG CAA CAG AAT GGT GAC TTC AAA GAT        2002
Ala Glu Lys Ser Ser Gly Glu Gln Gln Gln Asn Gly Asp Phe Lys Asp
                595                600                      605

GGT AAA AAT AAG ACA GAC AAG AAG GAT CAC TCT AAC ATC GGA AAT GAT        2050
Gly Lys Asn Lys Thr Asp Lys Lys Asp His Ser Asn Ile Gly Asn Asp
610                 615                620                      625

TCA AAG AAA ACA GAT GAT TCA CAA GAG TAAAAAAGAC CTCATAGACA             2097
Ser Lys Lys Thr Asp Asp Ser Gln Glu
```

-continued

```
               630
ATAAAAGAGG CTGCCAGTGT CTTGCATCAT TCTAGCTGAG CTTCTTCATT CTCCTTCTTC      2157

TCCTTCTTCC ACAAAGACCC ATATCTGGAG AAGGTGTACA ACTTTCAAAC ACAAGCCCCC      2217

CACCCCCTGA CCCTTGGCCT TCCCTCACAC CATCTCCTTC CAGGGGATGA ATCTTTGGGG      2277

GTTGGTTTGA GGTCTTAGAA CTCTGGGGGA TATTCCCCTG AGCAAAACAA ACAACGTGAG      2337

ATTTTTACTC AAACAGAAAC AAAACATGAA GGGGCATCCT CAAAATCCTT TGCTAATGAC      2397

CTGGCTTTCA AGGCATCTGT CTGGCCTGAT GAGAATGGAC ATCCTGGATA TGCTGGGAGA      2457

GGCCTGAAAA AAGCCACACA CACAGTAATT GCCATTTTAT GACTGTCAAT GCCGTTACTT      2517

TAAATGTTGT CATTTTTGCA CTGGCTACTG ATGATACAGC CATGCTGACA TTCATCACCG      2577

CAAAGATGAT GATTCCAGTC TCTGGTTCCT TTCCTGAGTC AGGAACATTT GTTTTCTCCA      2637

ATTTCCTTTC AGACTTAAAA TTGTTCTTAT GCTTTTTTTC CCACTTCTGT AATACA         2693
```

(2) INFORMATION FOR SEQ ID NO:51:

(i) SEQUENCE CHARACTERISTICS:
        (A) LENGTH: 634 amino acids
        (B) TYPE: amino acid
        (D) TOPOLOGY: linear (ii) MOLECULE TYPE: protein (xi) SEQUENCE DESCRIPTION: SEQ ID NO:51:

```
Met Glu Ser Pro Thr Lys Glu Ile Glu Phe Glu Ser Asn Ser Leu
 1               5                  10                  15

Lys Tyr Leu Gln Pro Glu Gln Ile Glu Lys Ile Trp Leu Arg Leu Arg
                20                  25                  30

Gly Leu Arg Lys Tyr Lys Lys Thr Ser Gln Arg Leu Arg Ser Leu Val
                35                  40                  45

Lys Gln Leu Glu Arg Gly Glu Ala Ser Val Val Asp Leu Lys Lys Asn
     50                  55                  60

Leu Glu Tyr Ala Ala Thr Val Leu Glu Ser Val Tyr Ile Asp Glu Thr
 65                  70                  75                  80

Arg Arg Leu Leu Asp Thr Glu Asp Glu Leu Ser Asp Ile Gln Ser Asp
                85                  90                  95

Ala Val Pro Ser Glu Val Arg Asp Trp Leu Ala Ser Thr Phe Thr Arg
                100                 105                 110

Gln Met Gly Met Met Leu Arg Arg Ser Asp Glu Lys Pro Arg Phe Lys
            115                 120                 125

Ser Ile Val His Ala Val Gln Ala Gly Ile Phe Val Glu Arg Met Tyr
        130                 135                 140

Arg Arg Thr Ser Asn Met Val Gly Leu Ser Tyr Pro Pro Ala Val Ile
145                 150                 155                 160

Glu Ala Leu Lys Asp Val Asp Lys Trp Ser Phe Asp Val Phe Ser Leu
                165                 170                 175

Asn Glu Ala Ser Gly Asp His Ala Leu Lys Phe Ile Phe Tyr Glu Leu
            180                 185                 190

Leu Thr Arg Tyr Asp Leu Ile Ser Arg Phe Lys Ile Pro Ile Ser Ala
        195                 200                 205

Leu Val Ser Phe Val Glu Ala Leu Glu Val Gly Tyr Ser Lys His Lys
    210                 215                 220

Asn Pro Tyr His Asn Leu Met His Ala Ala Asp Val Thr Gln Thr Val
225                 230                 235                 240

His Tyr Leu Leu Tyr Lys Thr Gly Val Ala Asn Trp Leu Thr Glu Leu
```

```
                      245                 250                 255
Glu Ile Phe Ala Ile Ile Phe Ser Ala Ala Ile His Asp Tyr Glu His
                260                 265                 270

Thr Gly Thr Thr Asn Asn Phe His Ile Gln Thr Arg Ser Asp Pro Ala
            275                 280                 285

Ile Leu Tyr Asn Asp Arg Ser Val Leu Glu Asn His His Leu Ser Ala
        290                 295                 300

Ala Tyr Arg Leu Leu Gln Asp Asp Glu Glu Met Asn Ile Leu Ile Asn
305                 310                 315                 320

Leu Ser Lys Asp Asp Trp Arg Glu Phe Arg Thr Leu Val Ile Glu Met
                325                 330                 335

Val Met Ala Thr Asp Met Ser Cys His Phe Gln Gln Ile Lys Ala Met
            340                 345                 350

Lys Thr Ala Leu Gln Gln Pro Glu Ala Ile Glu Lys Pro Lys Ala Leu
        355                 360                 365

Ser Leu Met Leu His Thr Ala Asp Ile Ser His Pro Ala Lys Ala Trp
    370                 375                 380

Asp Leu His His Arg Trp Thr Met Ser Leu Leu Glu Glu Phe Phe Arg
385                 390                 395                 400

Gln Gly Asp Arg Glu Ala Glu Leu Gly Leu Pro Phe Ser Pro Leu Cys
                405                 410                 415

Asp Arg Lys Ser Thr Met Val Ala Gln Ser Gln Val Gly Phe Ile Asp
            420                 425                 430

Phe Ile Val Glu Pro Thr Phe Thr Val Leu Thr Asp Met Thr Glu Lys
        435                 440                 445

Ile Val Ser Pro Leu Ile Asp Glu Thr Ser Gln Thr Gly Gly Thr Gly
    450                 455                 460

Gln Arg Arg Ser Ser Leu Asn Ser Ile Ser Ser Asp Ala Lys Arg
465                 470                 475                 480

Ser Gly Val Lys Thr Ser Gly Ser Glu Gly Ser Ala Pro Ile Asn Asn
                485                 490                 495

Ser Val Ile Ser Val Asp Tyr Lys Ser Phe Lys Ala Thr Trp Thr Glu
            500                 505                 510

Val Val His Ile Asn Arg Glu Arg Trp Arg Ala Lys Val Pro Lys Glu
        515                 520                 525

Glu Lys Ala Lys Lys Glu Ala Glu Lys Ala Arg Leu Ala Ala Glu
530                 535                 540

Glu Gln Gln Lys Glu Met Glu Ala Lys Ser Gln Ala Glu Glu Gly Ala
545                 550                 555                 560

Ser Gly Lys Ala Glu Lys Lys Thr Ser Gly Glu Thr Lys Asn Gln Val
                565                 570                 575

Asn Gly Thr Arg Ala Asn Lys Ser Asp Asn Pro Arg Gly Lys Asn Ser
            580                 585                 590

Lys Ala Glu Lys Ser Ser Gly Glu Gln Gln Gln Asn Gly Asp Phe Lys
        595                 600                 605

Asp Gly Lys Asn Lys Thr Asp Lys Lys Asp His Ser Asn Ile Gly Asn
    610                 615                 620

Asp Ser Lys Lys Thr Asp Asp Ser Gln Glu
625                 630

(2) INFORMATION FOR SEQ ID NO:52:

(i) SEQUENCE CHARACTERISTICS:
        (A) LENGTH: 2077 base pairs
        (B) TYPE: nucleic acid
```

(C) STRANDEDNESS: single
        (D) TOPOLOGY: linear (ii) MOLECULE TYPE: cDNA (ix) FEATURE:
        (A) NAME/KEY: CDS
        (B) LOCATION: 2..1693

(xi) SEQUENCE DESCRIPTION: SEQ ID NO:52:

| A | CGG | ACA | TCA | AAC | ATG | GTT | GGA | CTG | AGC | TAT | CCA | CCA | GCT | GTT | ATT | 46 |
|---|-----|-----|-----|-----|-----|-----|-----|-----|-----|-----|-----|-----|-----|-----|-----|----|
|   | Arg | Thr | Ser | Asn | Met | Val | Gly | Leu | Ser | Tyr | Pro | Pro | Ala | Val | Ile |    |
|   | 1   |     |     |     | 5   |     |     |     |     | 10  |     |     |     |     | 15  |    |

| GAG | GCA | TTA | AAG | GAT | GTG | GAC | AAG | TGG | TCC | TTT | GAC | GTC | TTT | TCC | CTC | 94 |
|-----|-----|-----|-----|-----|-----|-----|-----|-----|-----|-----|-----|-----|-----|-----|-----|----|
| Glu | Ala | Leu | Lys | Asp | Val | Asp | Lys | Trp | Ser | Phe | Asp | Val | Phe | Ser | Leu |    |
|     |     |     | 20  |     |     |     |     | 25  |     |     |     |     | 30  |     |     |    |

| AAT | GAG | GCC | AGT | GGG | GAT | CAT | GCA | CTG | AAA | TTT | ATT | TTC | TAT | GAA | CTA | 142 |
|-----|-----|-----|-----|-----|-----|-----|-----|-----|-----|-----|-----|-----|-----|-----|-----|-----|
| Asn | Glu | Ala | Ser | Gly | Asp | His | Ala | Leu | Lys | Phe | Ile | Phe | Tyr | Glu | Leu |     |
|     |     |     |     | 35  |     |     |     |     | 40  |     |     |     |     | 45  |     |     |

| CTC | ACA | CGT | TAT | GAT | CTG | ATC | AGC | CGT | TTC | AAG | ATC | CCC | ATT | TCT | GCA | 190 |
|-----|-----|-----|-----|-----|-----|-----|-----|-----|-----|-----|-----|-----|-----|-----|-----|-----|
| Leu | Thr | Arg | Tyr | Asp | Leu | Ile | Ser | Arg | Phe | Lys | Ile | Pro | Ile | Ser | Ala |     |
|     |     |     |     | 50  |     |     |     |     | 55  |     |     |     |     | 60  |     |     |

| CTT | GTC | TCA | TTT | GTG | GAG | GCC | CTG | GAA | GTG | GGA | TAC | AGC | AAG | CAC | AAA | 238 |
|-----|-----|-----|-----|-----|-----|-----|-----|-----|-----|-----|-----|-----|-----|-----|-----|-----|
| Leu | Val | Ser | Phe | Val | Glu | Ala | Leu | Glu | Val | Gly | Tyr | Ser | Lys | His | Lys |     |
|     |     | 65  |     |     |     |     | 70  |     |     |     |     | 75  |     |     |     |     |

| AAT | CCT | TAC | CAT | AAC | TTA | ATG | CAC | GCT | GCC | GAT | GTT | ACA | CAG | ACA | GTG | 286 |
|-----|-----|-----|-----|-----|-----|-----|-----|-----|-----|-----|-----|-----|-----|-----|-----|-----|
| Asn | Pro | Tyr | His | Asn | Leu | Met | His | Ala | Ala | Asp | Val | Thr | Gln | Thr | Val |     |
| 80  |     |     |     |     | 85  |     |     |     |     | 90  |     |     |     |     | 95  |     |

| CAT | TAC | CTC | CTC | TAT | AAG | ACA | GGA | GTG | GCG | AAC | TGG | CTG | ACG | GAG | CTG | 334 |
|-----|-----|-----|-----|-----|-----|-----|-----|-----|-----|-----|-----|-----|-----|-----|-----|-----|
| His | Tyr | Leu | Leu | Tyr | Lys | Thr | Gly | Val | Ala | Asn | Trp | Leu | Thr | Glu | Leu |     |
|     |     |     |     | 100 |     |     |     |     | 105 |     |     |     |     | 110 |     |     |

| GAG | ATC | TTT | GCT | ATA | ATC | TTC | TCA | GCT | GCC | ATC | CAT | GAC | TAC | GAG | CAT | 382 |
|-----|-----|-----|-----|-----|-----|-----|-----|-----|-----|-----|-----|-----|-----|-----|-----|-----|
| Glu | Ile | Phe | Ala | Ile | Ile | Phe | Ser | Ala | Ala | Ile | His | Asp | Tyr | Glu | His |     |
|     |     |     |     | 115 |     |     |     |     | 120 |     |     |     |     | 125 |     |     |

| ACC | GGA | ACC | ACC | AAC | AAT | TTC | CAC | ATT | CAG | ACT | CGG | TCT | GAT | CCA | GCT | 430 |
|-----|-----|-----|-----|-----|-----|-----|-----|-----|-----|-----|-----|-----|-----|-----|-----|-----|
| Thr | Gly | Thr | Thr | Asn | Asn | Phe | His | Ile | Gln | Thr | Arg | Ser | Asp | Pro | Ala |     |
|     |     | 130 |     |     |     |     | 135 |     |     |     |     | 140 |     |     |     |     |

| ATT | CTG | TAT | AAT | GAC | AGA | TCT | GTA | CTG | GAG | AAT | CAC | CAT | TTA | AGT | GCA | 478 |
|-----|-----|-----|-----|-----|-----|-----|-----|-----|-----|-----|-----|-----|-----|-----|-----|-----|
| Ile | Leu | Tyr | Asn | Asp | Arg | Ser | Val | Leu | Glu | Asn | His | His | Leu | Ser | Ala |     |
| 145 |     |     |     |     | 150 |     |     |     |     | 155 |     |     |     |     |     |     |

| GCT | TAT | CGC | CTT | CTG | CAA | GAT | GAC | GAG | GAA | ATG | AAT | ATT | TTG | ATT | AAC | 526 |
|-----|-----|-----|-----|-----|-----|-----|-----|-----|-----|-----|-----|-----|-----|-----|-----|-----|
| Ala | Tyr | Arg | Leu | Leu | Gln | Asp | Asp | Glu | Glu | Met | Asn | Ile | Leu | Ile | Asn |     |
| 160 |     |     |     |     | 165 |     |     |     |     | 170 |     |     |     |     | 175 |     |

| CTC | TCA | AAG | GAT | GAC | TGG | AGG | GAG | TTT | CGA | ACC | TTG | GTA | ATT | GAA | ATG | 574 |
|-----|-----|-----|-----|-----|-----|-----|-----|-----|-----|-----|-----|-----|-----|-----|-----|-----|
| Leu | Ser | Lys | Asp | Asp | Trp | Arg | Glu | Phe | Arg | Thr | Leu | Val | Ile | Glu | Met |     |
|     |     |     |     | 180 |     |     |     |     | 185 |     |     |     |     | 190 |     |     |

| GTG | ATG | GCC | ACA | GAT | ATG | TCT | TGT | CAC | TTC | CAA | CAA | ATC | AAA | GCA | ATG | 622 |
|-----|-----|-----|-----|-----|-----|-----|-----|-----|-----|-----|-----|-----|-----|-----|-----|-----|
| Val | Met | Ala | Thr | Asp | Met | Ser | Cys | His | Phe | Gln | Gln | Ile | Lys | Ala | Met |     |
|     |     |     | 195 |     |     |     |     | 200 |     |     |     |     | 205 |     |     |     |

| AAG | ACT | GCT | CTG | CAG | CAG | CCA | GAA | GCC | ATT | GAA | AAG | CCA | AAA | GCC | TTA | 670 |
|-----|-----|-----|-----|-----|-----|-----|-----|-----|-----|-----|-----|-----|-----|-----|-----|-----|
| Lys | Thr | Ala | Leu | Gln | Gln | Pro | Glu | Ala | Ile | Glu | Lys | Pro | Lys | Ala | Leu |     |
|     |     |     | 210 |     |     |     |     | 215 |     |     |     |     | 220 |     |     |     |

| TCC | CTT | ATG | CTG | CAT | ACA | GCA | GAT | ATT | AGC | CAT | CCA | GCA | AAA | GCA | TGG | 718 |
|-----|-----|-----|-----|-----|-----|-----|-----|-----|-----|-----|-----|-----|-----|-----|-----|-----|
| Ser | Leu | Met | Leu | His | Thr | Ala | Asp | Ile | Ser | His | Pro | Ala | Lys | Ala | Trp |     |
| 225 |     |     |     |     | 230 |     |     |     |     | 235 |     |     |     |     |     |     |

| GAC | CTC | CAT | CAT | CGC | TGG | ACA | ATG | TCA | CTC | CTG | GAG | GAG | TTC | TTC | AGA | 766 |
|-----|-----|-----|-----|-----|-----|-----|-----|-----|-----|-----|-----|-----|-----|-----|-----|-----|
| Asp | Leu | His | His | Arg | Trp | Thr | Met | Ser | Leu | Leu | Glu | Glu | Phe | Phe | Arg |     |
| 240 |     |     |     |     | 245 |     |     |     |     | 250 |     |     |     |     | 255 |     |

| CAG | GGT | GAC | AGA | GAA | GCA | GAG | CTG | GGG | CTG | CCT | TTT | TCT | CCT | CTG | TGT | 814 |
|-----|-----|-----|-----|-----|-----|-----|-----|-----|-----|-----|-----|-----|-----|-----|-----|-----|
| Gln | Gly | Asp | Arg | Glu | Ala | Glu | Leu | Gly | Leu | Pro | Phe | Ser | Pro | Leu | Cys |     |
|     |     |     | 260 |     |     |     |     | 265 |     |     |     |     | 270 |     |     |     |

| GAC | CGA | AAG | TCC | ACT | ATG | GTT | GCT | CAG | TCA | CAA | GTA | GGT | TTC | ATT | GAT | 862 |

```
         Asp Arg Lys Ser Thr Met Val Ala Gln Ser Gln Val Gly Phe Ile Asp
                     275                 280                 285

TTC ATC GTG GAA CCC ACC TTC ACT GTG CTT ACG GAC ATG ACC GAG AAG            910
Phe Ile Val Glu Pro Thr Phe Thr Val Leu Thr Asp Met Thr Glu Lys
        290                 295                 300

ATT GTG AGT CCA TTA ATC GAT GAA ACC TCT CAA ACT GGT GGG ACA GGA            958
Ile Val Ser Pro Leu Ile Asp Glu Thr Ser Gln Thr Gly Gly Thr Gly
        305                 310                 315

CAG AGG CGT TCG AGT TTG AAT AGC ATC AGC TCG TCA GAT GCC AAG CGA            1006
Gln Arg Arg Ser Ser Leu Asn Ser Ile Ser Ser Ser Asp Ala Lys Arg
320                 325                 330                 335

TCA GGT GTC AAG ACC TCT GGT TCA GAG GGA AGT GCC CCG ATC AAC AAT            1054
Ser Gly Val Lys Thr Ser Gly Ser Glu Gly Ser Ala Pro Ile Asn Asn
                340                 345                 350

TCT GTC ATC TCC GTT GAC TAT AAG AGC TTT AAA GCT ACT TGG ACG GAA            1102
Ser Val Ile Ser Val Asp Tyr Lys Ser Phe Lys Ala Thr Trp Thr Glu
                355                 360                 365

GTG GTG CAC ATC AAT CGG GAG AGA TGG AGG GCC AAG GTA CCC AAA GAG            1150
Val Val His Ile Asn Arg Glu Arg Trp Arg Ala Lys Val Pro Lys Glu
            370                 375                 380

GAG AAG GCC AAG AAG GAA GCA GAG GAA AAG GCT CGC CTG GCC GCA GAG            1198
Glu Lys Ala Lys Lys Glu Ala Glu Glu Lys Ala Arg Leu Ala Ala Glu
        385                 390                 395

GAG CAG CAA AAG GAA ATG GAA GCC AAA AGC CAG GCT GAA GAA GGC GCA            1246
Glu Gln Gln Lys Glu Met Glu Ala Lys Ser Gln Ala Glu Glu Gly Ala
400                 405                 410                 415

TCT GGC AAA GCT GAG AAA AAG ACG TCT GGA GAA ACT AAG AAT CAA GTC            1294
Ser Gly Lys Ala Glu Lys Lys Thr Ser Gly Glu Thr Lys Asn Gln Val
                420                 425                 430

AAT GGA ACA CGG GCA AAC AAA AGT GAC AAC CCT CGT GGG AAA AAT TCC            1342
Asn Gly Thr Arg Ala Asn Lys Ser Asp Asn Pro Arg Gly Lys Asn Ser
                435                 440                 445

AAA GCT GAG AAG TCA TCA GGA GAA CAG CAA CAG AAT GGT GAC TTC AAA            1390
Lys Ala Glu Lys Ser Ser Gly Glu Gln Gln Gln Asn Gly Asp Phe Lys
        450                 455                 460

GAT GGT AAA AAT AAG ACA GAC AAG AAG GAT CAC TCT AAC ATC GGA AAT            1438
Asp Gly Lys Asn Lys Thr Asp Lys Lys Asp His Ser Asn Ile Gly Asn
465                 470                 475

GAT TCA AAG AAA ACA GAT GGC ACA AAA CAG CGT TCT CAC GGC TCA CCA            1486
Asp Ser Lys Lys Thr Asp Gly Thr Lys Gln Arg Ser His Gly Ser Pro
480                 485                 490                 495

GCC CCA AGC ACC AGC TCC ACG TGT CGC CTT ACG TTG CCA GTC ATC AAG            1534
Ala Pro Ser Thr Ser Ser Thr Cys Arg Leu Thr Leu Pro Val Ile Lys
                500                 505                 510

CCT CCT TTG CGT CAT TTT AAA CGC CCT GCT TAC GCA TCT AGC TCC TAT            1582
Pro Pro Leu Arg His Phe Lys Arg Pro Ala Tyr Ala Ser Ser Ser Tyr
            515                 520                 525

GCA CCT TCA GTC TCA AAG AAA ACT GAT GAG CAT CCT GCA AGG TAC AAG            1630
Ala Pro Ser Val Ser Lys Lys Thr Asp Glu His Pro Ala Arg Tyr Lys
        530                 535                 540

ATG CTA GAT CAG AGG ATC AAA ATG AAA AAG ATT CAG AAC ATC TCA CAT            1678
Met Leu Asp Gln Arg Ile Lys Met Lys Lys Ile Gln Asn Ile Ser His
    545                 550                 555

AAC TGG AAC AGA AAA TAGGCCGAGG GGAAGAAGAG AGGGAGTGAA GGAGGGTCTA            1733
Asn Trp Asn Arg Lys
560

CCTATCTGCT TCTCAGCACC CACTGGCCAC AGCAGGACAC ACCTCCAAGA CCCTTGGAGG         1793

CTGTTGGAGC AGGTACTATC CTGGTTGACT CCACCAAGGT GAAATGAAAG TTGTATGTGA         1853

TTTTCCTCTT TGTTGTTCTT GTATAGACTT TTCAATTGCT GTATGTGGGA TCAGCCCAGA         1913
```

```
CGCCAGCAAC AAACTAGCAA GAGGGGTGTT TTTATGGTAT AAGTCTCTAA AAGTCTAAAT      1973

TGGACCAAAA TTAAAATGAC ACAAACTTAA AAAAAAATAA AATTCCTCTC ATTGCCACTT      2033

TTTTCAATCT CTAAAAGTTA CTTGCCCCCA AAGAATATT GGTC                       2077
```

(2) INFORMATION FOR SEQ ID NO:53:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:53:

```
Arg Thr Ser Asn Met Val Gly Leu Ser Tyr Pro Pro Ala Val Ile Glu
 1               5                  10                  15

Ala Leu Lys Asp Val Asp Lys Trp Ser Phe Asp Val Phe Ser Leu Asn
            20                  25                  30

Glu Ala Ser Gly Asp His Ala Leu Lys Phe Ile Phe Tyr Glu Leu Leu
        35                  40                  45

Thr Arg Tyr Asp Leu Ile Ser Arg Phe Lys Ile Pro Ile Ser Ala Leu
    50                  55                  60

Val Ser Phe Val Glu Ala Leu Glu Val Gly Tyr Ser Lys His Lys Asn
65                  70                  75                  80

Pro Tyr His Asn Leu Met His Ala Ala Asp Val Thr Gln Thr Val His
                85                  90                  95

Tyr Leu Leu Tyr Lys Thr Gly Val Ala Asn Trp Leu Thr Glu Leu Glu
            100                 105                 110

Ile Phe Ala Ile Ile Phe Ser Ala Ala Ile His Asp Tyr Glu His Thr
        115                 120                 125

Gly Thr Thr Asn Asn Phe His Ile Gln Thr Arg Ser Asp Pro Ala Ile
    130                 135                 140

Leu Tyr Asn Asp Arg Ser Val Leu Glu Asn His His Leu Ser Ala Ala
145                 150                 155                 160

Tyr Arg Leu Leu Gln Asp Asp Glu Glu Met Asn Ile Leu Ile Asn Leu
                165                 170                 175

Ser Lys Asp Asp Trp Arg Glu Phe Arg Thr Leu Val Ile Glu Met Val
            180                 185                 190

Met Ala Thr Asp Met Ser Cys His Phe Gln Gln Ile Lys Ala Met Lys
        195                 200                 205

Thr Ala Leu Gln Gln Pro Glu Ala Ile Glu Lys Pro Lys Ala Leu Ser
    210                 215                 220

Leu Met Leu His Thr Ala Asp Ile Ser His Pro Ala Lys Ala Trp Asp
225                 230                 235                 240

Leu His His Arg Trp Thr Met Ser Leu Leu Glu Glu Phe Phe Arg Gln
                245                 250                 255

Gly Asp Arg Glu Ala Glu Leu Gly Leu Pro Phe Ser Pro Leu Cys Asp
            260                 265                 270

Arg Lys Ser Thr Met Val Ala Gln Ser Gln Val Gly Phe Ile Asp Phe
        275                 280                 285

Ile Val Glu Pro Thr Phe Thr Val Leu Thr Asp Met Thr Glu Lys Ile
    290                 295                 300

Val Ser Pro Leu Ile Asp Glu Ser Gln Thr Gly Gly Thr Gly Gln
305                 310                 315                 320

Arg Arg Ser Ser Leu Asn Ser Ile Ser Ser Ser Asp Ala Lys Arg Ser
```

```
                    325                 330                 335
Gly Val Lys Thr Ser Gly Ser Glu Gly Ser Ala Pro Ile Asn Asn Ser
                340                 345                 350
Val Ile Ser Val Asp Tyr Lys Ser Phe Lys Ala Thr Trp Thr Glu Val
                355                 360                 365
Val His Ile Asn Arg Glu Arg Trp Arg Ala Lys Val Pro Lys Glu Glu
                370                 375                 380
Lys Ala Lys Lys Glu Ala Glu Lys Ala Arg Leu Ala Ala Glu Glu
385                 390                 395                 400
Gln Gln Lys Glu Met Glu Ala Lys Ser Gln Ala Glu Glu Gly Ala Ser
                405                 410                 415
Gly Lys Ala Glu Lys Lys Thr Ser Gly Glu Thr Lys Asn Gln Val Asn
                420                 425                 430
Gly Thr Arg Ala Asn Lys Ser Asp Asn Pro Arg Gly Lys Asn Ser Lys
                435                 440                 445
Ala Glu Lys Ser Ser Gly Glu Gln Gln Gln Asn Gly Asp Phe Lys Asp
                450                 455                 460
Gly Lys Asn Lys Thr Asp Lys Lys Asp His Ser Asn Ile Gly Asn Asp
465                 470                 475                 480
Ser Lys Lys Thr Asp Gly Thr Lys Gln Arg Ser His Gly Ser Pro Ala
                485                 490                 495
Pro Ser Thr Ser Ser Thr Cys Arg Leu Thr Leu Pro Val Ile Lys Pro
                500                 505                 510
Pro Leu Arg His Phe Lys Arg Pro Ala Tyr Ala Ser Ser Ser Tyr Ala
                515                 520                 525
Pro Ser Val Ser Lys Lys Thr Asp Glu His Pro Ala Arg Tyr Lys Met
                530                 535                 540
Leu Asp Gln Arg Ile Lys Met Lys Lys Ile Gln Asn Ile Ser His Asn
545                 550                 555                 560
Trp Asn Arg Lys (2) INFORMATION FOR SEQ ID NO:54:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

TACGAAGCTT TGATGGGGTC TACTGCTAC                                 29

(2) INFORMATION FOR SEQ ID NO:55:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

TACGAAGCTT TGATGGTTGG CTTGGCATAT C                              31

(2) INFORMATION FOR SEQ ID NO:56:

(i) SEQUENCE CHARACTERISTICS:
```

```
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

ATTACCCCTC ATAAAG                                                   16

(2) INFORMATION FOR SEQ ID NO:57:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

TACGAAGCTT TGATGCGCCG ACAGCCTGC                                     29

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:58:

GGTCTCCTGT TGCAGATATT G                                             21
```

ASSAY METHODS USING DNA ENCODING MAMMALIAN PHOSPHODIESTERASES

This is a Divisional of U.S. application Ser. No.08/455,525, U.S. Pat. No. 5,800,987 filed May 31, 1995, which in turn is a Rule 60 Divisional of U.S. patent application Ser. No. 08/297,494, U.S. Pat. No. 5,580,771 filed Aug. 29, 1994, which in turn is a Rule 60 Divisional of U.S. patent application Ser. No. 07/872,644, U.S. Pat. No. 5,389,527 filed Apr. 20, 1992 which is a continuation-in-part of our U.S. patent application Ser. No. 07/688,356, filed Apr. 19, 1991, now abandoned.

BACKGROUND OF THE INVENTION

The present invention relates to novel purified and isolated nucleotide sequences encoding mammalian $Ca^{2+}$/calmodulin stimulated phosphodiesterases (CaM-PDEs) and cyclic-GMP-stimulated phosphodiesterases (cGS-PDEs). Also provided are the corresponding recombinant expression products of said nucleotide sequences, immunological reagents specifically reactive therewith, and procedures for identifying compounds which modulate the enzymatic activity of such expression products.

Cyclic nucleotides are known to mediate a wide variety of cellular responses to biological stimuli. The cyclic nucleotide phosphodiesterases (PDEs) catalyze the hydrolysis of 3', 5' cyclic nucleotides, such as cyclic adenosine monophosphate (cAMP) and cyclic guanosine monophosphate (cGMP), to their corresponding 5'-nucleotide monophosphates and are consequently important in the control of cellular concentration of cyclic nucleotides. The PDEs in turn are regulated by transmembrane signals or second messenger ligands such as calcium ion ($Ca^{2+}$) or cGMP. The PDEs thus have a central role in regulating the flow of information from extracellular hormones, neurotransmitters, or other signals that use the cyclic nucleotides as messengers.

PDEs are a large and complex group of enzymes. They are widely distributed throughout the cells and tissues of most eukaryotic organisms, but are usually present only in trace amounts. At least five different families of PDEs have been described based on characteristics such as substrate specificity, kinetic properties, cellular regulatory control, size, and in some instances, modulation by selective inhibitors. [Beavo, Adv. in Second Mess. and Prot. Phosph. Res. 22:1–38 (1988)]. The five families include:

I $Ca^{2+}$/calmodulin-stimulated
II cGMP-stimulated
III cGMP-inhibited
IV cAMP-specific
V cGMP-specific Within each family there are multiple forms of closely related PDEs. See Beavo, "Multiple Phosphodiesterase Isozymes Background, Nomenclature and Implications", pp. 3–15; Wang et al., "Calmodulin-Stimulated Cyclic Nucleotide Phosphodiesterases", pp. 19–59; and Manganiello et al., "Cyclic GMP-Stimulated Cyclic Nucleotide Phosphodiesterases" pp. 62–85; all in Cyclic Nucleotide Phosphodiesterases: Structure, Regulation and Drug Action, Beavo, J. and Houslay, M. D., Eds.; John Wiley & Sons, New York (1990).

The $Ca^{2+}$/calmodulin dependent PDEs (CaM-PDEs) are characterized by their responsiveness to intracellular calcium, which leads to a decreased intracellular concentration of cAMP and/or cGMP. A distinctive feature of cGMP-stimulated phosphodiesterases (cGS-PDEs) is their capacity to be stimulated by CGMP in effecting cAMP hydrolysis.

In vitro studies have shown increased PDE activity in response to $Ca^{2+}$/calmodulin in nearly every mammalian tissue studied, as well as in Drosophila, Dictyostelium, and trypanosomes. The level of CaM-PDE in tissues and cellular and subcellular compartments varies widely. Most cells contain at least a small amount of CaM-PDE activity, with the highest tissue levels being found in the brain, particularly in the synaptic areas. Greenberg et al. Neuropharmacol., 17:737–745 (1978) and Kincaid et al., PNAS (USA), 84:1118–1122 (1987). A decrease in cAMP in astrocytoma cells in response to muscarinic stimulation may be due to calcium dependent increases in CaM-PDE activity. Tanner et al., Mol. Pharmacol., 29:455–460 (1986). Also, CaM-PDE may be an important regulator of cAMP in thyroid tissue. Erneux et al., Mol. Cell. Endocrinol., 43:123–134 (1985).

Early studies suggested that there are distinct tissue-specific isozymes of CaM-PDEs. Several members of the CaM-PDE family have now been described, including a 59 kDa isozyme isolated from bovine heart, and 61 and 63 kDa isozymes isolated from bovine brain. LaPorte et al., Biochemistry, 18:2820–2825 (1979); Hansen et al., Proc. Natl. Acad. Sci. USA, 79:2788–2792 (1982); and Sharma et al., J. Biol. Chem., 261:14160–14166 (1986). Possible counterparts to the bovine 59 and 61 kDa isozymes have also been isolated from rat tissues, Hansen et al., J. Biol. Chem., 261:14636–14645 (1986), suggesting that these two isozymes may be expressed in other mammalian species.

In addition to molecular weight criteria, other evidence supports both similarities and differences among the CaM-PDE family of isozymes. For example, the 59 kDa heart isozyme and the 61 kDa brain isozyme CaM-PDEs differ in mobility on SDS-PAGE and elution position on DEAE chromatography, and the 59 kDa isozyme has at least a 10–20 fold higher affinity for calmodulin. Oncomodulin, a fetal/onco calcium binding protein present in very high concentrations in the placenta and transformed cells, also binds to the 59 kDa enzyme with a higher affinity than to the 61 kDa enzyme. However, both the 61 kDa brain and the 59 kDa heart isozymes are recognized by a single monoclonal antibody. This antibody binds to the $Ca^{2+}$/CaM-PDE complex with 100-fold higher affinity than to PDE alone. Hansen et al., 1986, supra. The 59 and 61 kDA isozymes have nearly identical substrate specificities and kinetic constants. Krinks et al., Adv. Cyc. Nucleotide Prot. Phosphorylation Res., 16:31–47 (1984) have suggested, based on peptide mapping experiments, that the heart 59 kDa protein could be a proteolytic form of the brain 61 kDa isozyme.

The 63 kDa bovine brain isozyme differs substantially from the 59 and 61 kDa isozymes. The 63 kDa enzyme is not recognized by the monoclonal antibody which binds to the 59 and 61 kDa enzymes. Hansen et al., 1986, supra. The 63 kDa protein is not phosphorylated in vitro by cAMP-dependent protein kinase, whereas the 61 kDa protein is phosphorylated. Further, only the 63 kDa protein is phosphorylated in vitro by CaM-kinase II. Sharma et al., Proc. Natl. Acad. Sci. (USA), 82:2603–2607 (1985); and Hashimoto et al., J. Biol. Chem., 264:10884–10887 (1989). The 61 and 63 kDa CaM-PDE isozymes from bovine brain do appear, however, to have similar CaM-binding affinities. Peptide maps generated by limited proteolysis with Staphylococcal V8 protease, Sharma et al., J. Biol.Chem., 259:9248 (1984), have suggested that the 61 and 63 kDa proteins have different amino acid sequences.

The cGMP-stimulated PDEs (cGS-PDEs) are proposed to have a noncatalytic, cGMP-specific site that may account for the stimulation of cAMP hydrolysis by cGMP. Stoop et al., *J.Biol.Chem.*, 264:13718 (1989). At physiological cyclic nucleotide concentrations, this enzyme responds to elevated cGMP concentrations with an enhanced hydrolysis of cAMP. Thus, cGS-PDE allows for increases in cGMP concentration to moderate or inhibit cAMP-mediated responses. The primary sequence presented recently in LeTrong et al., *Biochemistry*, 29:10280 (1990), co-authored by the inventors herein, provides the molecular framework for understanding the regulatory properties and domain substructure of this enzyme and for comparing it with other PDE isozymes that respond to different signals. This publication also notes the cloning of a 2.2 kb bovine adrenal cortex cDNA fragment encoding cGS-PDE. See also, Thompson et al., *FASEB J.*, 5(6):A1592 (Abstract No. 7092) reporting on the cloning of a "Type II PDE" from rat pheochromocytoma cells.

With the discovery of the large number of different PDEs and their critical role in intracellular signalling, efforts have focused on finding agents that selectively activate or inhibit specific PDE isozymes. Agents which affect cellular PDE activity, and thus alter cellular cAMP, can potentially be used to control a broad range of diseases and physiological conditions. Some drugs which raise cAMP levels by inhibiting PDEs are in use, but generally act as broad nonspecific inhibitors and have deleterious side effects on cAMP activity in nontargeted tissues and cell types. Accordingly, agents are needed which are specific for selected PDE isozymes. Selective inhibitors of specific PDE isozymes may be useful as cardiotonic agents, anti-depressants, anti-hypertensives, anti-thrombotics, and as other agents. Screening studies for agonists/antagonists have been complicated, however, because of difficulties in identifying the particular PDE isozyme present in a particular assay preparation. Moreover, all PDEs catalyze the same basic reaction; all have overlapping substrate specificities; and all occur only in trace amounts.

Differentiating among PDEs has been attempted by several different means. The classical enzymological approach of isolating and studying each new isozyme is hampered by current limits of purification techniques and by the inability to accurately assess whether complete resolution of an isozyme has been achieved. A second approach has been to identify isozyme-specific assay conditions which might favor the contribution of one isozyme and minimize that of others. Another approach has been the immunological identification and separation into family groups and/or individual isozymes. There are obvious problems with each of these approaches; for the unambiguous identification and study of a particular isozyme, a large number of distinguishing criteria need to be established, which is often time consuming and in some cases technically quite difficult. As a result, most studies have been done with only partially pure PDE preparations that probably contained more than one isozyme. Moreover, many of the PDEs in most tissues are very susceptible to limited proteolysis and easily form active proteolytic products that may have different kinetic, regulatory, and physiological properties from their parent form.

The development of new and specific PDE-modulatory agents would be greatly facilitated by the ability to isolate large quantities of tissue-specific PDEs by recombinant means. Relatively few PDE genes have been cloned to date and of those cloned, most belong to the cAMP-specific family of-phosphodiesterases (cAMP-PDEs). See Davis, "Molecular Genetics of the Cyclic Nucleotide Phosphodiesterases", pp. 227–241 in *Cyclic Nucleotide Phosphodiesterases: Structure, Regulation, and Drug Action*, Beavo, J. and Houslay, M. D., Eds.; John Wiley & Sons, New York; 1990. See also, e.g., Faure et al., *PNAS (USA)*, 85:8076 (1988) - *D. discoideum;* Sass et al., *PNAS (USA)*, 83:9303 (1986) - *S. cerevisiae,* PDE class IV, designated PDE2; Nikawa et al., *Mol. Cell. Biol.*, 7:3629 (1987) - *S. cerevisiae*, designated PDE1; Wilson et al., *Mol. Cell. Biol.*, 8:505 (1988) - *S. cerevisiae*, designated SRA5; Chen et al., *PNAS (USA)*, 83:9313 (1986) - *D. melanogaster,* designated dnc$^+$; Ovchinnikow et al., *FEBS*, 223:169 (1987) - *bovine retina,* designated GMP PDE; Davis et al., *PNAS (USA)*, 86:3604 (1989) - rat liver, designated rat dnc-1; Colicelli et al., *PNAS (USA)*, 86:3599 (1989) - rat brain, designated DPD; Swinnen et al., *PNAS (USA)*, 86:5325 (1989) - rat testis, rat PDE1, PDE2, PDE3 and PDE4; and Livi et al., *Mol. Cell. Biol.*, 10:2678 (1990) - human monocyte, designated hPDE1. See also, LeTrong et al., supra and Thompson et al., supra.

Complementation screening has been used to detect and isolate mammalian cDNA clones encoding certain types of PDEs. Colicelli et al., *PNAS (USA)*, 86:3599 (1989), reported the construction of a rat brain cDNA library in an *S. cerevisiae* expression vector and the isolation therefrom of genes having the capacity to function in yeast to suppress the phenotypic effects of RAS2$^{val19}$, a mutant form of the RAS2 gene analogous to an oncogenic mutant of the human HRAS gene. A cDNA so cloned and designated DPD (rat dunce-like phospho-diesterase) has the capacity to complement or "rescue" the loss of growth control associated with an activated RAS2$^{val19}$ gene harbored in yeast strain TK161-R2V (A.T.C.C. 74050), as well as the analogous defective growth control phenotype of the yeast mutant 10DAB (A.T.C.C. 74049) which is defective at both yeast PDE gene loci (pde-$^1$, pde.-$^2$). The gene encodes a high-affinity cAMP specific phosphodiesterase, the amino acid sequence of which is highly homologous to the cAMP-specific phosphodiesterase encoded by the dunce locus of *Drosophila melanogaster.*

Through the date of filing of parent application Ser. No. 07/688,356, there have been no reports of the cloning and expression of DNA sequences encoding any of the mammalian Ca$^{2+}$/calmodulin stimulated or cGMP-stimulated PDEs (PDE families I and II) and, accordingly, there continues to exist a need in the art for complete nucleotide sequence information for these PDEs.

BRIEF SUMMARY OF THE INVENTION

The present invention provides novel purified and isolated polynucleotide sequences (e.g. DNA and RNA including sense and antisense strands) which code for expression of mammalian species (e.g., human and bovine) Ca$^{2+}$/calmodulin stimulated cyclic nucleotide phosphodiesterase and cGMP stimulated cyclic nucleotide phosphodiesterase polypeptides. Genomic and cDNA sequences provided by the invention may be associated with homologous or heterologous species expression control DNA sequences such as promoters, operators, regulators, terminators and the like to allow for in vivo and in vitro transcription to messenger RNA and, in turn, translation of mRNAs to provide functional phosphodiesterases and related polypeptides in large quantities.

Specifically provided by the invention are mammalian DNA-sequences encoding phosphodiesterases and fragments thereof which are present as mammalian DNA inserts in bacterial plasmids and viral vectors which are the subject of deposits made with the American Type Culture Collection, 12301 Parklawn Drive, Rockville, Md. 20852 on Apr. 11 and 15, 1991 and on Apr. 14, 1992 in accordance with U.S. Patent and Trademark Office and Budapest Treaty requirements. DNAs deposited in connection with the present invention include:

1. Plasmid pCAM-40 in *E. coli* (A.T.C.C. accession No. 68576) containing a bovine brain cDNA insert encoding a 61 kDa CaM-PDE isozyme;

2. Plasmid p12.3A in *E. coli* (A.T.C.C. 68577) containing a bovine brain cDNA insert encoding a 63 kDa CaM-PDE isozyme;

3. Bacteriophage λ CaM H6a (A.T.C.C. accession No. 75000) containing a human hippocampus cDNA insert fractionally encoding a 61 kDa CaM-PDE isozyme;

4. Plasmid pHcam61-6N-7 in *E. coli* (A.T.C.C. accession No. 68963) containing a composite human cDNA insert encoding a 61 kDa CaM-PDE isozyme;

5. Plasmid pcamH3EF in *E. coli* (A.T.C.C. accession No. 68964) containing a human hippocampus cDNA insert encoding a novel PDE homologous to a 61 kDa CaM-PDE;

6. Plasmid pcamHella in *E. coli* (A.T.C.C. accession No. 68965) containing a human heart cDNA insert encoding a novel PDE homologous to a 61 kDa CaM-PDE;

7. Plasmid p3CGS-5 in *E. coli* (A.T.C.C. accession No. 68579) containing a bovine adrenal cDNA insert encoding a cGS-PDE isozyme;

8. Plasmid pBBCGSPDE-5 in *E. coli* (A.T.C.C. accession No. 68578) containing a bovine brain cDNA insert encoding a cGS-PDE isozyme fragment;

9. Plasmid pBBCGSPDE-7 in *E. coli* (A.T.C.C. accession No. 68580) containing a bovine brain cDNA encoding a cGS-PDE isozyme;

10. Plasmid pGSPDE6.1 in *E. coli* (A.T.C.C. accession No. 68583) containing a human heart cDNA encoding a cGS-PDE isozyme fragment;

11. Plasmid pGSPDE7.1 in *E. coli* (A.T.C.C. accession No. 68585) containing a human hippocampus cDNA insert encoding a cGS-PDE isozyme fragment; and 12. Plasmid pGSPDE9.2 (A.T.C.C. accession No. 68584) containing a human hippocampus cDNA insert encoding a cGS-PDE isozyme fragment. 13. Plasmid pHcgs6n in *E. coli* (A.T.C.C. accession No. 68962) containing a human cDNA insert encoding a cGS-PDE.

Also specifically provided by the present invention is a bovine CDNA sequence containing nucleotides encoding bovine 59 kDa CaM-PDE and characterized by the DNA and amino acid sequences of SEQ ID NO: 16 and SEQ ID NO: 17.

In related embodiments, the invention concerns DNA constructs which comprise a transcriptional promoter, a DNA sequence which encodes the PDE or a fragment thereof, and a transcriptional terminator, each operably linked for expression of the enzyme or enzyme fragment. The constructs are preferably used to transform or transfect host cells, preferably eukaryotic cells, and more preferably mammalian or yeast cells. For large scale production, the expressed PDE can be isolated from the cells by, for example, immunoaffinity purification.

Incorporation of DNA sequences into procaryotic and eucaryotic host cells by standard transformation and transfection processes, potentially involving suitable DNA and RNA viral vectors and circular DNA plasmid vectors, is also within the contemplation of the invention and is expected to provide useful proteins in quantities heretofore unavailable from natural sources. Systems provided by the invention include transformed *E. coli* cells, including those referred to above, as well as other transformed eukaryotic cells, including yeast and mammalian cells. Use of mammalian host cells is expected to provide for such post-translational modifications (e.g., truncation, lipidation, and tyrosine, serine or threonine phosphorylation) as may be needed to confer optimal biological activity on recombinant expression products of the invention.

Novel protein products of the invention include expression products of the aforementioned nucleic acid sequences and polypeptides having the primary structural conformation (i.e., amino acid sequence) of CaM-PDE and cGS-PDE proteins, as well as peptide fragments thereof and synthetic peptides assembled to be duplicative of amino acid sequences thereof. Proteins, protein fragments, and synthetic peptides of the invention are projected to have numerous uses including therapeutic, diagnostic, and prognostic uses and will provide the basis for preparation of monoclonal and polyclonal antibodies specifically immunoreactive with the proteins of the invention.

Also provided by the present invention are antibody substances (including polyclonal and monoclonal antibodies, chimeric antibodies, single chain antibodies and the like) characterized by their ability to bind with high immunospecificity to the proteins of the invention and to their fragments and peptides, recognizing unique epitopes which are not common to other proteins. The monoclonal antibodies of the invention can be used for affinity purification of CaM-PDEs and cGS-PDEs, e.g., Hansen et al., *Meth. Enzymol.*, 159:543 (1988).

Also provided by the present invention are novel procedures for the detection and/or quantification of normal, abnormal, or mutated forms of CaM-PDEs and cGS-PDEs, as well as nucleic acids (e.g., DNA and mRNA) associated therewith. Illustratively, antibodies of the invention may be employed in known immunological procedures for quantitative detection of these proteins in fluid and tissue samples, and of DNA sequences of the invention that may be suitably labelled and employed for quantitative detection of MRNA encoding these proteins.

Among the multiple aspects of the present invention, therefore, is the provision of (a) novel CaM-PDE and cGS-PDE encoding polynucleotide sequences, (b) polynucleotide sequences encoding polypeptides having the activity of a mammalian CaM-PDE or of a mammalian cGS-PDE which hybridize to the novel CaM-PDE and cGS-PDE encoding sequences under hybridization conditions of the stringency equal to or greater than the conditions described herein and employed in the initial isolation of cDNAs of the invention, and (c) polynucleotide sequences encoding the same (or allelic variant or analog polypeptides) through use of, at least in part, degenerate codons. Correspondingly provided are viral DNA and RNA vectors or circular plasmid DNA vectors incorporating polynucleotide sequences and procaryotic and eucaryotic host cells transformed or transfected with such polynucleotide sequences and vectors, as well as novel methods for the recombinant production of these proteins through cultured growth of such hosts and isolation of the expressed proteins from the hosts or their culture media.

In yet other embodiments, the invention provides compositions and methods for identifying compounds which can modulate PDE activity. Such methods comprise incubating a compound to be evaluated for PDE modulating activity with eukaryotic cells which express a recombinant PDE polypeptide and determining therefrom the effect of the compound on the phosphodiesterase activity provided by gene expression. The method is effective with either whole cells or cell lysate preparations. In a preferred embodiment, the eukaryotic cell is a yeast cell or mammalian cell which lacks endogenous phosphodiesterase activity. The effect of the compound on phosphodiesterase activity can be determined by means of biochemical assays which monitor the hydrolysis of cAMP and/or cGMP, or by following the effect of the compound on the alteration of a phenotypic trait of the eukaryotic cell associated with the presence or absence of the recombinant PDE polypeptide.

Other aspects and advantages of the present invention will be apparent upon consideration of the following detailed description thereof which includes numerous illustrative examples of the practice of the invention, reference being made to the drawing wherein:

FIGURE 1 provides the results of amino acid sequence determinations for isolated 59 kDa (bovine heart) and 63 kDa (bovine brain) CaM-PDE proteins in alignment with the complete sequence of the 61 kDa (bovine brain) isozyme. Identities of the 59 and 63 kDa proteins to the 61 kDa isozyme are underlined. Tentative identifications are in lower cases and hyphens denote unidentified residues. The N-terminus of the 59 kDa isozyme, as determined by the subtraction of a methionyl peptide (mDDHVTIRRK) from the composition of an amino-terminal blocked lysyl peptide, is in parenthesis. Solid boxes are placed above residues within the CaM-binding sites identified in the 61 and 59 kDa isozymes.

DETAILED DESCRIPTION OF THE INVENTION

Figure 1A:
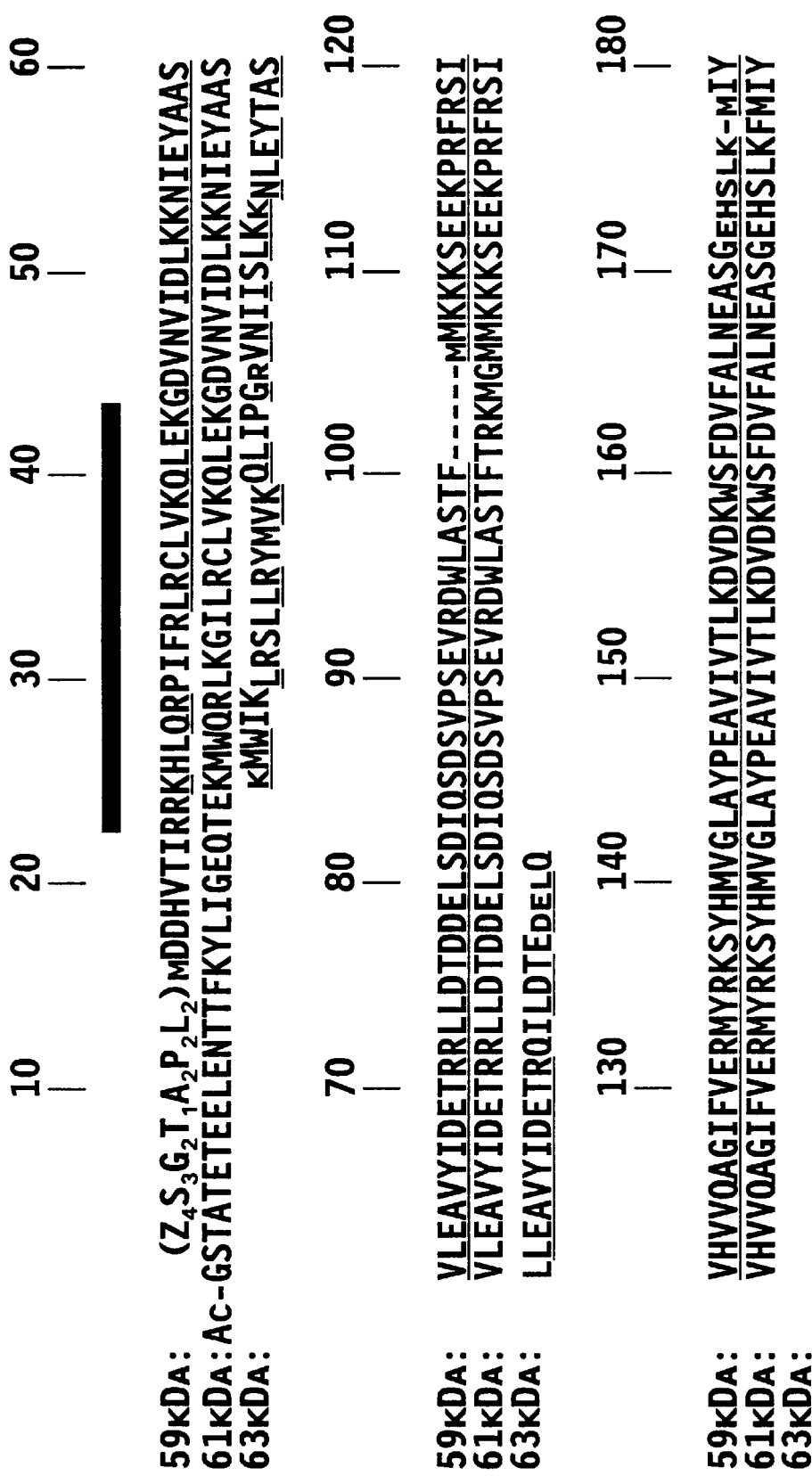

The following examples illustrate practice of the invention. Example I relates to the isolation, purification, and sequence determination of 61 kDa CaM-PDE cDNA from bovine brain and to the expression thereof in a mammalian host cell. Example II relates to the isolation, purification, and sequence determination of a 59 kDa CaM-PDE from bovine lung and to the expression thereof in a mammalian host cell. Example III relates to the isolation, purification, and sequence determination of 63 kDa CaM-PDE cDNA from bovine brain and to the expression thereof in a mammalian host cell. Example IV relates to the isolation, purification, and sequence determination of cGS-PDE cDNA from bovine adrenal cortex, as well as the expression of the DNA in mammalian host cells. Example V relates to the isolation, purification, and sequence determination of cGS-PDE cDNA from bovine brain and to the expression thereof in a mammalian host cell. Example VI relates to the use of cGS-PDE bovine adrenal cDNA to obtain human cGS-PDE cDNAs and to the development of a human cDNA encoding a cGS-PDE. Example VII relates to the use of CaM-PDE 61 kDa bovine brain cDNA to obtain a human CaM-PDE 61 kDa cDNA and a novel structurally related cDNA. Example VIII relates to the expression of bovine and human PDE cDNAs for complementation of yeast phenotypic defects and verification of phosphodiesterase activity for the expression product. Example IX relates to tissue expression studies involving Northern analysis and RNase protection studies employing polynucleotides (specifically cDNAs and antisense RNAS) of the invention.

In those portions of the text addressing the formation of redundant oligonucleotides, the following Table I single letter code recommendations for ambiguous nucleotide sequence, as reported in *J.Biol.Chem.*, 261:13–17 (1986), are employed:

TABLE I

| Symbol | Meaning | Origin of designation |
| --- | --- | --- |
| G | G | Guanine |
| A | A | Adenine |
| T | T | Thymine |
| C | C | Cytosine |
| R | G or A | puRine |
| Y | T or C | pYrimidine |
| M | A or C | aMino |
| | G or T | Keto |
| S | G or C | Strong interaction (3 H bonds) |
| W | A or T | Weak interaction (2 H bonds) |
| H | A, C, or T | not G, as H follows G in the alphabet |
| B | G, C, or T | not A |
| V | A, C, or G | not T, (not U) as V follows U |
| D | A, G, or T | not C |
| N | A, C, G, or T | any Nucleotide base |

EXAMPLE I

Isolation, Purification, and Sequence Determination of 61 kDa CaM-PDE cDNA From Bovine Brain In this Example, a cDNA sequence representing that portion of a gene for 61 kDa bovine brain CaM-PDE which encodes the amino terminus of the protein was isolated by PCR from a collection of first strand cDNAs developed from bovine brain mRNA. The PCR-generated fragment was then employed to isolate a full length bovine brain CaM-PDE sequence.

Total RNA was prepared from bovine heart using the method of Chomczynski et al., *Anal.Biochem.*, 162:156–159 (1987) and mRNA was selected using a Poly(A) QuikTm mRNA purification kit according to the manufacturer's protocol. First strand cDNA was synthesized by adding 80 units of AMV reverse transcriptase to a reaction mixture (40 μl, final volume) containing 50 mM Tris HCl (pH8.3 @ 42°), 10 mM MgCl$_2$, 10 mM dithiothreitol, 0.5 mM (each) deoxynucleotide triphosphates, 50 mM KCl, 2.5 mM sodium pyrophosphate, 5 μg deoxythymidylic acid oligomers (12–18 bases) and 5 μg bovine heart mRNA denatured for 15 min at 65°. Incorporation of 1 μl [$^{32}$P]-labeled dCTP (3000 Ci/mmol) was used to quantitate first strand cDNA synthesis. The reaction was incubated at 42° for 60 min. The reaction was phenol/CHCl$_3$ extracted and EtOH precipitated. The nucleic acid pellet was resuspended in 50 μl of 10 mM Tris-HCl (pH 7.5)/0.1 mM EDTA to a final concentration of 15 ng per μl.

Redundant sense and antisense oligomers corresponding to 61 kDa peptide sequences as in FIGURE 1 were designed to be minimally redundant, yet long enough to specifically hybridize to the target template.

A first 23 base oligomer, designated CaM PCR-2S, was synthesized on an Applied Biosystems, Inc. DNA synthesizer. The oligomer had the following sequence,
SEQ ID NO: 1
5'-AARATGGGNATGAARAARAA-3'
which specifies the following amino acid sequence,
SEQ ID NO: 2
KMGMMKKK.

A second 23 base oligomer, designated CaM PCR-3AS, was synthesized with the following sequence, SEQ ID NO: 3
5'-ACRTTCATYTCYTCYTCYTGCAT-3'
representing the following amino acid sequence,
SEQ ID NO: 4
MQEEEMNV.

A 612 bp CaM PDE cDNA fragment was synthesized using the PCR amplification technique by adding 15 ng of first strand cDNA to a reaction mixture containing 50 mM KCl, 10 mM Tris-HCl (pH 9.0), 1.5 mM MgCl$_2$, 0.01% gelatin, 0.1% Triton X-100, 0.2 mM (each) deoxynucleotide triphosphates, 1 μM (each) CaM PCR 2S and CaM PCR-3AS oligomers, and 2.5 units of *Thermus aquaticus* DNA polymerase. The reaction was incubated for 30 cycles as follows: 94° for 1 min; 50° for 2 min; and 72° for 2 min. The reaction products were purified on a 1% agarose gel using 0.04 M Tris-acetate/0.001 M EDTA buffer containing 0.5 μg/ml ethidium bromide. The DNA products were visualized with UV light, cleanly excised from the gel with a razor blade, purified using Geneclean II reagent kit and ligated into Eco RV-cut pBluescript vector DNA.

To determine if the PCR amplification products were CaM PDE cDNAs, the subcloned PCR DNA products were sequenced from the ends using T3 and T7 promoter primers and either Sequenase or Taq Polymerase sequencing kits. Approximately 250 bases from each end of this piece of DNA were sequenced and the deduced amino acid sequence from the CDNA corresponded with the FIGURE 1 amino acid sequences of the 59 and 61 kDa CaM-PDEs, confirming that the PCR DNA product was a partial CaM PDE cDNA.

A bovine brain cDNA library constructed with the lambda ZAP vector (kindly provided by Ronald E. Diehl, Merck, Sharp & Dohme) was screened with the radiolabeled 615 bp CaM-PDE CDNA obtained by PCR amplification. The probe was prepared using the method of Feinberg et al., *Anal.Biochem.*, 137:266–267 (1984), and the [$^{32}$P]-labeled DNA was purified using Elutip-D® columns. Plaques (700,000 plaques on 12–150 mm plates) bound to filter circles were hybridized at 42° C. overnight in a solution containing 50% formamide, 20 mM Tris-HCl (pH 7.5), 1X Denhardt's solution, 10% dextran sulfate, 0.1% SDS and 10$^6$ cpm/ml [$^{32}$P]-labeled probe (10$^9$ cpm/μg). The filters were washed three times for 15 min with 2X SSC/0.1% SDS at room temperature, followed by two 15-min washes with 0.1X SSC/0.1% SDS at 45° C. The filters were exposed to x-ray film overnight.

Of the fifty-six plaques that hybridized with the [$^{32}$P]-labeled probes eight randomly selected clones were purified by several rounds of re-plating and screening [Maniatis et al., *Molecular Cloning: A Laboratory Manual* 545 pp. Cold Spring Harbor Laboratory, Cold Spring Harbor, N.Y., (1982)] and the insert cDNA's were subcloned into pBluescript SK(-) by in vivo excision [Short et al., *Nuc. Acids Res.*, 16:7583–7599 (1988)] as recommended by the manufacturer.

Plasmid DNA prepared from cultures of each clone were subjected to restriction analysis using EcoRI. Two clones of a suitable length were selected for sequence analysis using Taq Tak® and Sequenase® sequencing kits. The two clones were pCAM-40 (2.3 kb) and pCAM-34 (2.7 kb). The sequencing information from this procedure confirmed that the insert of pCAM-40 encoded the full length bovine brain 61 kDa CaM-PDE. The sequence of this clone and the amino acid sequence deduced therefrom are set forth in SEQ ID NO: 5 and SEQ ID NO: 6.

Transient expression of the 61 kDa CaM-PDE cDNA in COS-7 cells (A.T.C.C. CRL 1651) was accomplished as follows. Vector pCDM8 [Seed, *Nature,* 329:840–843 (1987)] in *E. coli* host cells MC1061-p3 was generously provided by Dr. Brian Seed, Massachusetts General Hospital, Boston, Mass. This vector is also available from Invitrogen, Inc. (San Diego, Calif.). Plasmid pCAM-40 was digested with HindIII and NotI, yielding a 2.3 kb fragment which was ligated into CDM8 vector DNA which had been digested with HindIII and NotI. The resulting plasmid was propagated in MC1061-p3 cells. Plasmid DNA was prepared using the alkaline lysis method of Ausubel et al., eds., *Current Protocols in Molecular Biology,* 1:1.7.1 (John Wiley & Sons, New York, 1989) and purified using Qiagen-Tip 500 columns (Qiagen, Inc. Chatsworth, Calif.) according to the manufacturer protocol.

COS-7 cells were transfected with the p-CAM-40/CDM8 construct (or mock transfected with the CDM8 vector alone) using the DEAE-dextran method Ausubel et al., supra at 1:9.2 et seq. Specifically, 10 μg of ethanol precipitated DNA was resuspended in 80 Ml TBS buffer, and added to 160 μl of 10 mg per ml DEAE-dextran dropwise to a 100 mm plate of 50% confluent COS-7 cells in 4 ml of DMEM supplemented with 10% NuSerum, and mixed by swirling. The cells were incubated for 3–4 hours at 37° in a water-saturated 7% CO$_2$ atmosphere. The medium was removed and the cells were immediately treated with 10% DMSO in PBS for 1 minute. Following this treatment, the cells were washed with PBS, then DMEM, and finally cultured in DMEM supplemented with 10% fetal bovine serum and antibiotics (50 μg/ml streptomycin sulfate) in a 7%-CO$_2$ incubator for 36 hours.

COS cells were scraped from the plates and homogenized in a buffer containing 40 mM Tris-HCl (pH=7.5), 5 mM EDTA, 15 mM benzamidine, 15 mM beta-mercaptoethanol, 1 μg per ml pepstatin A and 1 μg per ml peupeptin using an ounce homogenizer (1 ml per 100 mm plate). Homogenates were assayed for PDE activity according to the procedures of Hanson et al., *Proc. Nat'l. Acad. Sci., U.S.A.,* 79:2788–2792 (1982), using [$^3$H]cGMP as the substrate. Reactions were carried out at 30° for 10 minutes in a buffer containing 20 mM Tris-HCl (pH=7.5), 20 mM imidazole (pH=7.5), 3 mM MgCl$_2$, 15 mM Mg acetate, 0.2 mg per ml BSA and 1 μM $^3$H-cAMP with either 2 mM EGTA or 0.2 mM CaCl$_2$ and 4 μg per ml CaM. Assays were stopped by incubating the tubes in a 90° water bath for 1 minute. After cooling, 10 μl of 2.5 mg per ml snake venom was added to each assay and incubated at 37° for 5 minutes. The samples were diluted with 250 μl of 20 mM Tris-HCl (pH=7.5) and immediately applied to 0.7 ml A-25 ion exchange columns. The columns were washed three times with 0.5 ml of 20 mM Tris-HCl (pH=7.5) and the eluate was collected in scintillation vials. Samples were counted for 1 minute using a Packard Model 1600TR scintillation counter. Specific cyclic nucleotide hydrolytic activity was expressed as picomoles cAMP or cGMP hydrolyzed per minute per mg protein. Protein concentration was estimated according to the method of Bradford, *Anal. Biochem.,* 72:248–254 (1976), using BSA as a standard. When compared to mock transfected cells, extracts of cells transfected with pCAM-40 cDNA contained significantly greater CAMP and cGMP hydrolytic activities in the presence of EGTA. Assays of the pCAM-40 cDNA-transfected cells in the presence of calcium and CaM resulted in stimulation of cAMP and cGMP hydrolysis.

EXAMPLE II

Isolation, Purification, and Sequence Determination of a 59 kDa CaM-PDE From Bovine Lung A fully degenerate sense oligonucleotide corresponding to the amino acid sequence SEQ ID NO: 7
  MDDHVTI
from the bovine heart 59 kDa CaM-pde was synthesized. The nucleotide sequence of this oligonucleotide is
SEQ ID NO: 8
  5'-ATGAGRAGRCAYGTHACNAT-3'.
An antisense oligonucleotide was designed from the FIGURE 1 sequence of bovine brain 61 kDa CaM-PDE, corresponding to the amino acid sequence
SEQ ID NO: 9
  LRCLVKQ
and having the sequence,
SEQ ID NO: 10
  5'-CTGCTTCACTAAGCATCTTAG-3'.
This primer pair was used to prime a PCR reaction using bovine heart first strand cDNA (as prepared in Example I) as a template. This predicted a PCR product of 75 bp, 54 bp of which were unique 59 kDa sequence and 21 bp of which were shared between the 59 kDa and 61 kDa isozymes. The PCR products were analyzed by sieving agarose gel electrophoresis, and a band migrating at 75 bp was excised from the gel. The DNA was subcloned into pBluescript KS+, and colonies positive by the blue/white selection scheme were screened by PCR using primers directed against vector sequences. Colonies with inserts of the appropriate size were selected, and one of these (pCaM59/75.14) was chosen for sequencing. Plasmid DNA was prepared using a Qiagen P20 push column and used as template for sequencing using the dideoxy method. The sequence of the PCR product is

SEQ ID NO: 11

5'-ATGAGAAGGCACGTAACGATCAGGAGGAAACATCTCCAA
AGACCCATCTTT-AGACTAAGATGCTTAGTGAAGCAG-3'.

Analysis of the sequence revealed differences in two codons between the sequence obtained and the predicted sequence. Re-examination of the sense oligonucleotide primer sequence revealed that an inadvertent transposition of two codons had led to a mistake in the design of the oligonucleotide. A second set of oligonucleotide PCR primers was prepared which predicted a 54 bp product with minimum overlap between the 59 and 61 kDa isozymes; in addition, the second sense primer incorporated a correction of the mistake in the design of the original sense primer. The sense oligonucleotide had the sequence
SEQ ID NO: 12
  5'-ATGGAYGAYCACGTAACGATC-3'
and the antisense oligonucleotide had the sequence
SEQ ID NO: 13
  5'-AAGTATCTCATTGGAGAACAG-3'
This primer pair was used to prime a PCR reaction using bovine heart first-strand CDNA as template and the PCR products subcloned and screened exactly as described above. Two clones (pCaM59/54.9 and pCaM59/54.10) were selected for sequencing based on insert size and sequenced as described above; both clones contained 54 bp inserts of the predicted sequence

SEQ ID NO: 14

5'-ATGGATGATCACGTAACGATCAGGAGGAAACATCTCCAAA
  GACCCATCT-TTAGA-3', predicting the amino acid sequence
SEQ ID NO: 15
  MDDHVTIRRKHLQRPIFR A cDNA library was constructed from bovine lung MRNA and screened using procedures as described in Example IV, infra, with respect to screening of a bovine adrenal cortex library. Approximately $1.2 \times 10^6$ plaque-forming units were probed with a $^{32}$P-labelled, 1.6 kb EcoRI restriction endonuclease-cleavage product of the pCAM-40 cDNA. This initial screening produced 4 putative 59 kDA CaM-PDE cDNA clones. Preliminary sequence analysis indicated that one clone, designated p59KCAMPDE-2, contained the complete coding sequence of the putative 59 kDa CaM-PDE. A series of nested deletions were constructed from the p59KCAMPDE-2 plasmid [See, Sonnenburg et al., J. Biol. Chem., 266 (26): 17655–17661 (1991)], and the resultant templates were sequenced by an adaptation of the method of Sanger using the Taq DyeDeoxy™ Terminator Cycle Sequencing Kit and an Applied Biosystems Model 373A DNA Sequencing System. The DNA and deduced amino acid sequences are set out in SEQ. ID NO: 16 and 17, respectively. A large open reading frame within the cDNA encodes a 515 residue polypeptide with an estimated molecular weight of ≈59 kilodaltons that is nearly identical to the 61 kDa CaM-PDE amino acid sequence except for the amino-terminal 18 residues. Moreover, the predicted amino acid sequence of the p59KCAMPDE-2 open reading frame is identical to the available sequence of the 59 kDa CaM-PDE purified from bovine heart, Novack et al., Biochemistry, 30: 7940–7947 (1991). These results indicate that the p59KCAMPDE-2 cDNA represents an mRNA species encoding the 59 kDa CaM-PDE.

Transient expression of the 59 kDa bovine lung PDE was accomplished as in Example I. Specifically, a 2.66 kb, EcoRI/blunt-ended fragment of p59KCAMPDE-2 cDNA was subcloned into pCDM8 which had been digested with XhoI and blunt-ended. The recombinant plasmid, designated p59KCAMPDE-2/CDM8, was used to transiently transfect COS-7 cells and extracts prepared from transfected COS-7 cells were assayed for CaM-PDE activity using 2 μM cAMP. COS-7 cells transfected with the p59KCAMPDE-2 cDNA yielded a cAMP hydrolytic activity that was stimulated 4–5 fold in the presence of calcium and calmodulin. Mock transfected COS-7 cells had no detectable calmodulin-stimulated cAMP hydrolytic activity.

EXAMPLE III

Isolation, Purification, and Sequence Determination of 63 kDa CaM-PDE cDNA From Bovine Brain Multiple fully and partially redundant oligonucleotides corresponding to the amino acid sequence reported in FIG. 1 were synthesized for use in attempting to obtain a cDNA clone for the 63 kDa CaM-PDE. Annealing temperatures used for the polymerase chain reactions were varied between 2 to 20° C. below the theoretical melting temperature for the lowest melting oligonucleotide of each sense-antisense pair. Except for probes 63–12s and 63–13a, which are discussed below, the PCR products of each of the oligonucleotide pairs under a wide range of conditions gave multiple ethidium bromide bands when agarose gel-electrophoresed. Use of 63–12s and 63–13a resulted in a PCR product that coded for 63 kDa CaM-PDE when sequenced.

A fully redundant sense 23-mer oligonucleotide, designated 63–12s, was assembled having the following sequence
SEQ ID NO: 18
  5'ATHCAYGAYTAYGARCAYACNGG-3'
based on an amino acid sequence,
SEQ ID NO: 19
  IHDYEHTG
which is conserved in the 61 kDa bovine CaM-PDEs (see FIG. 1). A partially redundant antisense 32-mer oligonucleotide, designated 63–13a, had the sequence

SEQ ID NO: 20

5'-TCYTTRTCNCCYTGNCGRAARAAYTCYTCCAT-3' and was based on the following conserved sequence in the 63 kDa CaM-PDE,

SEQ ID NO: 21

MEEFFRQGDKE

Messenger RNA was prepared from bovine brain cerebral cortex and poly A⁺ selected. First strand complementary DNA was produced using AMV or MMLV reverse transcriptase. De-tritylated oligonucleotides were phosphorylated using 1 mM [γ-$^{32}$P]ATP at 1×10$^6$ cpm/nmol and T4 polynucleotide kinase. After separation of 5'$^{32}$p_labelled oligonucleotides from free ATP using NENsorb 20 columns, each was suspended as a 20 μM (5' phosphate) stock and combined finally at 400 nM each in the PCR. The reaction was run using 50 ng total cDNA and 200 μM dNTP to obtain about 1 μg of PCR product. The reaction had an initial denaturation step at 94° C. for 5 min followed by 30 cycles of a 1 min 94° C. denaturation, an annealing step at 50° C. for 1 min, and a 2 min extension step at 72° C. Under the reaction conditions, a single ethidium bromide-staining band of 450 base pairs was obtained on agarose gel electrophoresis of 100 ng of the PCR product. Five μg of 5' phosphorylated PCR product was ligated to 15 ng EcoRV-cut Bluescript KS(+) plasmid using T4 DNA ligase in 5% PEG-6000 for 12 h at 21° C. Putative positives of XL 1-blue transformations were white colonies using isopropyl thiogalactoside (IPTG) and bromo- chloro- indolyl galactoside (Xgal) for chromogenic selection. Such picks were sequenced using T3 or T7 primers, dideoxynucleotide terminators, and Sequenase.

One resultant clone (p11.5B) had the nucleotide sequence and translated amino acid sequence provided in SEQ ID NO: 22 and SEQ ID NO: 23, respectively. The codons for the amino acids YEH found in oligonucleotide 63-12s were replaced by codons for the amino acid sequence NTR in p11.5B. This was probably due to a contaminant in 63-12s. Since the translated open reading frame (ORF) was similar to that reported in FIGURE 1 for the 63 kDa CaM PDE, p11.5B was used to screen a bovine brain cDNA library for a full length cDNA clone.

A bovine brain CDNA library was constructed in λ ZAP II. First strand cDNA was treated with RNase H, *E. coli* DNA polymerase, and *E. coli* DNA ligase to synthesize second strand cDNA. The cDNA was blunt-ended by T4-DNA polymerase; EcoRI sites in the CDNA were protected with EcoRI methylase and S-adenosyl methionine and EcoRI linkers were ligated on with T4 DNA ligase. After EcoRI restriction endonuclease treatment, free linkers were separated from the cDNA by gel filtration over Sepharose CL-4B. λ ZAP II arms were ligated onto the cDNA and packaged by an in vitro Gigapack Gold packaging kit obtained from Stratagene. 9.5×10$^5$ recombinants were obtained with 5.8% nonrecombinant plaques as assessed by plating with IPTG and X-gal. The library was amplified once by the plate lysate method to obtain 1.4×10$^7$ pfu/ml.

An initial screen of a total bovine brain cDNA library in λ ZAP II was performed. 700,000 pfu were screened using $^{32}$P-labelled oligonucleotide 63-1s at a hybridization and wash temperature of 40° C. Oligonucleotide 63-1s was a fully-redundant 23-mer having the sequence

SEQ ID NO: 24

5'-AARAARAAYYTNGARTAYACNGC-3' corresponding to the amino acid sequence

SEQ ID NO: 25

KKNLEYTA

A total of 21 putative positives were picked. Subsequent rescreens were impeded by the very high background found using this screening method. Therefore, aliquots of each primary pick were pooled and 50,000 pfu of the pool were replated and rescreened with p11.5B radiolabelled by random primers and [α-$^{32}$P]dCTP. One positive was obtained, plaque-purified, and rescued as a plasmid p12.3a. Its DNA sequence is provided in SEQ ID NO: 26. Subsequently, the bovine brain cerebral cortex library was screened further with p11.5B. Two further independent clones, p12.27.9 and p12.27.11, were obtained out of a primary screen of 1.4×10$^6$ pfu. They were plaque-purified and rescued for sequencing.

Clone p12.3a codes for a protein sequence with most of the aligned peptides isolated from bovine 63 kDa CaM-PDE as shown in FIG. 1. SEQ ID NO: 26 and SEQ ID NO: 27 set forth the coding region (i.e., the 1844 nucleotides of an approximately 2.5 kilobase insert) of p12.3a. Base numbers 248–290 code for amino acid sequence

SEQ ID NO: 28

QLENGEVNIEELKK, while the comparable (FIG. 1) peptide has the sequence

SEQ ID NO: 29

QLIPGRVNIISLKK

Base numbers 942–990 code for an amino acid sequence

SEQ ID NO: 30

KSECAILYNDRSVLEN while the isolated (FIG. 1) peptide sequence is

SEQ ID NO: 31

KDETAILYNDRTVLEN. None of the nonaligned 63 kDa peptide sequence is found in any reading frame of p12.3a; also, the molecular weight of the p12.3a open reading frame, as translated, is 60,951 not 63,000. Therefore, this cDNA may represent an isozyme variant of the 63 kDa protein. The other two independent clones (p12.27.9 and p12.27.11) seem to have ORF sequence identical to p12.3a. The open reading frame of one clone begins at nucleotide number 823 of p12.3a and is identical to p12.3a through its termination codon. The other clone starts at nucleotide 198 and is identical to p12.3a throughout its length. None of the three clones has the anomalous NTR peptide sequence found in p11.5B; all three have YEH as the 61 kDa CaM PDE.

Transient expression of the 63 kDa CaM-PDE cDNA in COS-7 cells was accomplished as follows. A fragment of the cDNA insert of plasmid p 12.3 including the protein coding region of SEQ.ID NO: 26 and flanked by BamHI restriction sites was prepared by PCR. More specifically, oligonucleotides corresponding to base Nos. 94–117 (with the putative initiation codon) and the antisense of base Nos. 1719–1735 (with sequence immediately 3' of the termination codon) of SEQ.ID NO. 26 were synthesized with two tandem BamHI sites on their 5' ends. The two primers had the following sequences:

SEQ.ID NO: 32

5'-GGATCCGGATCCCGCAGACGGAGGCTGAGCATGG-3'

SEQ.ID NO: 33

5'-GGATCCGGATCCAGGACCTGGCCAGGCCCGGC-3'

The two oligonucleotides were used in a PCR cycling 30 times from a 1 min incubation at 94° C. to a 2 min 72° C. incubation with a final 10 min extension reaction at 72° C. The 100 μl reaction used 20 μM of each oligonucleotide and 100 pg p12.3a as the template in order to produce 5 μg 1665 base pair product.

The product was extracted once with an equal volume of 1:1 phenol:chloroform, made 0.3 M with regard to sodium acetate, and precipitated with two volumes of ethanol overnight. The precipitate was dried, rehydrated into 50 μl, and the cDNA was digested with 5 units BamHI restriction endonuclease for one hour at 37° C. Afterwards, the solution was extracted once with an equal volume of 1:1 phenol:chloroform. The 1641 base pair cDNA with BamHI 5' and 3' ends was purified from the aqueous layer using Qiagen Q-20 columns (Qiagen, Inc., Chatsworth, Calif.) and the protocol given by the manufacturer.

The cut, purified PCR product was ligated into BamHI digested, alkaline phosphatase-treated Bluescript KS(+) plasmid. The ligation product was subcloned into XL1 cells; resulting transformants were screened by sequencing. One transformant (designated p11.6.c6) was isolated with the BamHI insert oriented such that the Bluescript KS(+) HindIII restriction site was 30 bases 5' to the sequence of the insert encoding the initiation codon. This plasmid was digested with HindIII and XbaI restriction endonucleases to release the 1689 base pair fragment. The fragment was ligated into HindIII- and XbAI-digested CDM8 vector DNA as in Example I.

COS-7 cells were transfected with the p12.3.a/CDM8 construct or mock transfected with the CDM8 vector alone using the DEAE-dextran method as described in Example 1. A ratio of 10 µg DNA/400 µg DEAE-dextran was used, with a final DEAE-dextran concentration in the media of 100 µg/ml. After 48 h, cells were suspended in 1 ml of homogenization buffer (40 mM Tris HCl, pH=7.5, 15 mM benzamidine HCl, 15 mM µ-mercaptoethanol, 0.7 µg/ml pepstatin A, 0.5 µg/ml leupeptin, and 5 mM Na$_4$EDTA) and disrupted on ice using a Dounce homogenizer. The homogenates were diluted ½ to make a final 50% (v/v) glycerol for storage at −20°C. and used either to assay for phosphodiesterase activity or to determine protein concentration. CaM-dependent and independent activities were determined as in Example 1. Cells transfected with a p12.3.a DNA had a 15-fold increase in CaM-stimulated cAMP phosphodiesterase activity and a 12-fold increase in CaM-stimulated cGMP phosphodiesterase activity over nasal levels. Mock transfected COS-7 cells showed no PDE activity over basal levels even with CaM stimulation.

EXAMPLE IV
Isolation, Purification, Sequence Determination, and Expression of cGS-PDE cDNA From Bovine Adrenal cortex Total RNA was prepared from bovine adrenal outer cortex using the method of Chomczynski et al., supra. Polyadenylated RNA was purified from total RNA preparations using the Poly(A) QuickTm MRNA purification kit according to the manufacturer's protocol. First strand cDNA was synthesized by adding 80 units of AMV reverse transcriptase to a reaction mixture (40 µl, final volume) containing 50 mM Tris-HCl (pH 8.3 @ 42°), 10 mM MgCl$_2$, 10 mM dithiothreitol, 0.5 mM (each) deoxynucleotide triphos hates, 50 mM KCl, 2.5 mM sodium pyrophosphate, 5 µg deoxythymidylic acid oligomers (12–18 bases) and 5 µg bovine adrenal cortex mRNA denatured for 15 min at 65° C. The reaction was incubated at 42° C. for 60 min. The second strand was synthesized using the method of Watson et al., *DNA Cloning: A Practical Approach*, 1:79–87 (1985) and the ends of the cDNA were made blunt with T4 DNA polymerase. EcoRI restriction endonuclease sites were methylated [Maniatis et al., supra] using a EcoRI methylase (Promega), and EcoRI linkers (50-fold molar excess) were ligated to the cDNA using T4 DNA ligase. Excess linkers were removed by digesting the cDNA with EcoRI restriction endonuclease, followed by Sepharose CL-4B chromatography. Ausubel et al., supra. The cDNA (25–50 ng per µg vector) was ligated into EcoRI-digested, dephosphorylated ZAP® II (Stratagene) arms [Short et al., *Nuc.Acids Res.*, 16:7583–7599 (1988)] and packaged [Maniatis et al., supra] with Gigapack® Gold extracts according to the manufacturer's protocol.

Initially, an unamplified bovine adrenal cortex cDNA library was made and screened with a redundant 23-mer antisense oligonucleotide probes end-labeled with γ-[$^{32}$P] ATP and T4 polynucleotide kinase. The oligomers corresponding to the amino acid sequences
SEQ ID NO: 34
  EMMMYHMK
and
SEQ ID NO: 35
  YHNWMHAF
were made using an Applied Biosystems model 380A DNA synthesizer. Their sequences are as follows:
SEQ ID NO: 36
  5'-TT CAT RTG RTA CAT CAT CAT YTC-3'
SEQ ID NO: 37
  5'-AA NGC RTG CAT CCA RTT RTG RTA-3'

Duplicate nitrocellulose filter circles bearing plaques from 12 confluent 150 mm plates (approximately 50,000 pfu/plate) were hybridized at 45° C. overnight in a solution containing 6X SSC, 1X Denhardt's solution, 100 µg/ml yeast tRNA, 0.05% sodium pyrophosphate and 10$^6$ cpm/ml radiolabeled probe (>10$^6$ cpm per pmol). The filters were washed three times in 6X SSC at room temperature, followed by a higher-stringency 6X SSC wash at 10° C. below the minimum melting temperature of the oligomer probes, and exposed to x-ray film overnight.

A single 2.1 kb CDNA clone (designated pcGS-3:2.1) was isolated and sequenced. The amino acid sequence enclosed by the large ORF of this clone was identical to peptide sequences of the cGS-PDE purified from the supernatant fraction of a bovine heart homogenate. LeTrong et al., supra.

A second, amplified, bovine adrenal cortex cDNA library was screened using the [$^{32}$P]-labeled CGS-3:2.1 partial cDNA, yielding a 4.2 kb cDNA (designated 3CGS-5).

The library was constructed, amplified as in Maniatis et al., supra, plated and screened with the bovine cDNA insert from clone CGS-3:2.1. The probe was prepared using the method of Feinberg et al., supra, and the radiolabeled DNA was purified using Elutip-D® columns. Plaques (600,000 pfu on twelve 150 mm plates) bound to filter circles were hybridized at 42° C. overnight in a solution containing 50% formamide, 20 mM Tris-HCl (pH 7.5, 1X Denhardt's solution, 10% dextran sulfate, 0.11% SDS and 10$^6$ cpm/ml [$^{32}$P]-labeled probe (10$^9$ cpm/µg). The filters were washed three times for 15 minutes with 2X SSC/0.1% SDS at room temperature, followed by two 15-minute washes with 0.1X SSC/0.1% SDS at 45° C. The filters were exposed to x-ray film overnight. Ausubel et al., supra.

From this initial screening, 52 putative clones were identified. Twenty of these clones were randomly selected, purified by several rounds of re-plating and screening [Maniatis et al., supra] and the insert cDNAs were subcloned into pBluescript SK(−) by in vivo excision [Short et al., supra] as recommended by the manufacturer. Plasmid DNA prepared from these clones were analyzed by restriction analysis and/or sequencing. From this survey, a 4.2 kb cDNA representing the largest open reading frame was identified. The cDNA inserts from the other putative clones were shorter, and appeared to be identical based on the nucleotide sequence of the insert ends.

Putative cGS-PDE cDNAs were sequenced by a modification of the Sanger method [Sanger et al., *Proc.Natl.Acad.Sci. USA*, 74:5463–5467] using Sequenase® or Taq Trak® kits as directed by the manufacturer. Templates were prepared from the cDNAs by constructing a series of nested deletions [Henikoff, *Gene*, 28:351–359 (1984)] in the vector, pBluescript SK(–) (Stratagene) using exonuclease III and mung bean nuclease according to the manufacturer's protocol. In cases where overlapping templates were not attained by this method, the cDNAs were cleaved at convenient restriction endonuclease sites and subcloned into pBluescript, or specific oligomers were manufactured to prime the template for sequencing. Single-stranded DNA templates were rescued by isolating the DNA from phagemid secreted by helper phage-infected XL1 cells harboring the pBluescript plasmid (Levinson et al., supra) as recommended by the manufacturer (Stratagene). Homology searches of GENBANK (Release 66.0), EMBL (Release 25.0), and NBRF nucleic acid (Release 36.0) and protein (Release 26.0) databases were conducted using Wordsearch, FASTA and TFASTA programs supplied with the Genetics Computer Group software package Devereux et al., *Nuc.Acids Res.*, 12:387–395 (1984).

The nucleotide sequence and deduced amino acid sequence encoded by the large open reading frame of p3CGS-5 cDNA clone insert is provided in SEQ ID NO: 38 and SEQ ID NO: 39. Starting with the first methionine codon, the cDNA encodes a 921 residue polypeptide with a calculated molecular weight of about 103,000. Although no stop codons precede this sequence, an initiator methionine consensus sequence [Kozak, *J.Cell Biol.*, 108:229–241 (1989)] has been identified. The presence of 36 adenosine residues at the 3' end of the cDNA preceded by a transcription termination consensus sequence [Birnstiel et al., *Cell*, 41:349–359 (1985)] suggests that all of the 3' untranslated sequence of the cGS-PDE mRNA is represented by this clone.

A putative phosphodiesterase-deficient (PPD) strain of S49 cells [Bourne et al., *J.Cell.Physiol.*, 85:611–620 (1975)] was transiently transfected with the cGS-PDE cDNA using the DEAE-dextran method. The cGS-PDE cDNA was ligated into the unique BamHI cloning site in a mammalian expression vector, designated pZEM 228, following a zinc-inducible metallothionine promoter and prior to an SV40 transcription termination sequence. The DNA was purified from large-scale plasmid preparations using Qiagen pack-500 columns as directed by the manufacturer. PPD-S49 cells were cultured in DMEM containing 10% heat-inactivated horse serum, 50 μg/ml penicillin G and 50 μg/ml streptomycin sulfate at 37° C. in a water-saturated 7% $CO_2$ atmosphere. Prior to transfections, confluent 100 mm dishes of cells were replated at one-fifth of the original density and incubated for 24–36 h. In a typical transfection experiment, PPD-S49 cells (50–80% confluent) were washed with Tris-buffered-saline and approximately $2 \times 10^7$ cells were transfected with 10 μg of DNA mixed with 400 μg of DEAE-dextran in one ml of TBS. The cells were incubated at 37° C. for 1 hr with gentle agitation every 20 min. Next, DMSO was added to a final concentration of 10% and rapidly mixed by pipetting up and down. After 2 min, the cells were diluted with 15 volumes of TBS, collected by centrifugation, and washed, consecutively with TBS and DMEM. The cells were resuspended in complete medium and seeded into fresh 100 mm plates (1–2×107 cells/10 ml/plate). After 24 h, the cells were treated with TBS alone, or containing zinc sulfate (final concentration=125 μM) and incubated for an additional 24 h. The cells were harvested and washed once with TBS. The final cell pellets were resuspended in two mls of homogenization buffer (40 mM Tris-HCl; pH 7.5, 15 mM benzamidine, 15 mM β-mercaptoethanol, 0.7 μg/ml pepstatin A, 0.5 μg/ml leupeptin and 5 mM EDTA) and disrupted on ice using a dounce homogenizer. The homogenates were centrifuged at 10,000×g for 5 min at 4° C. and the supernatants were assayed for phosphodiesterase activity and protein concentration.

cGS PDE activity was determined by a previously described method using [$^3$H]cAMP as the substrate as in Martins et al., *J.Biol.Chem.*, 257:1973–1979 (1982). Phosphodiesterase assays were performed in triplicate. The Bradford assay [Bradford, *Anal. Biochem.*, 72:248–254 (1976)] was used to quantitate protein using BSA as the standard.

In the absence of zinc treatment, no increase in basal activity or cGMP-stimulated phosphodiesterase activity was detected in PPD S49 cells transfected with the cGS PDE-ZEM 228 construct or the vector alone. However, zinc-treated cells transfected with cGS-PDE cDNA, but not the vector alone, expressed cGMP-enhanced cAMP phosphodiesterase activity indicating that the cDNA encodes a cGS-PDE. The total activity of the homogenates and 50,000×g supernatants was not significantly different.

Transient expression of the CGS-PDE cDNA in COS-7 cells was accomplished as in Example I. A 4.2 kb fragment of p3CGS-5 was isolated using HindIII and NotI and was inserted into plasmid pCDM8, which had been digested with the same enzymes. The character of products produced in COS-7 cells transformed with the p3CGS-5pCDM8 construct is discussed in Example V, infra.

EXAMPLE V

Isolation, Purification, and Partial Sequence Determination of cGS-PDE cDNA from Bovine Brain A. Isolation of Bovine Brain cGSPDE cDNA Clone, pBBCGSPDE-5

A bovine brain cDNA library constructed with the λ ZAP vector (kindly provided by Ronald E. Diehl, Merck, Sharp & Dohme) was screened with a 450 bp EcoRI/ApaI restriction endonuclease cleavage fragment of the p3CGS-5 cDNA corresponding to (p3CGS-5) nucleotide position numbers 1–452. The probe was prepared using the method of Feinberg et al., supra, and the [$^{32}$P]-labeled DNA was purified using Elutip D® columns. Plaques (a total of 600,000 plaques on 12–150 mm plates) bound to filter circles were hybridized at 42° overnight in a solution containing 50% formamide, 20 mM Tris HCl (pH 7.5), 1X Denhardt's solution, 10% dextran sulfate, 0.1% SDS and $10^6$ cpm/ml [$^{32}$P]-labeled probe ($10^9$ cpm/μg). The filters were washed three times for 15 minutes with 2X SSC/0.1% at room temperature, followed by two 15 minute washes with 0.1X SSC/0.1% SDS at 45%. The filters were exposed to x-ray film overnight.

Forty putative clones were picked from this first screen, of which six were randomly selected and purified by several rounds of re-plating and screening [Maniatis et al., supra]. The insert cDNAs were subcloned into pBluescript SK(–) by in vivo excision as recommended by the manufacturer. Plasmid DNA prepared from cultures of each clone was sequenced from the ends using Sequenase and Taq Trak sequencing kits. The sequence obtained from this experiment confirmed that the bovine brain cDNA clone, pBBCGSPDE-5 was a cGS-PDE cDNA, and that it was different than the adrenal cGS-PDE cDNA at the five-prime end.

Partial sequence analysis of the pBBCGSPDE-5 insert at its 5' end (encoding the amino terminal region of the protein) revealed the sense strand set out in SEQ ID NO: 40, while sequencing of the 3' end of the insert revealed the antisense sequence of SEQ ID NO: 41.

B. Isolation of Bovine Brain cGS-PDE cDNA Clone, pBBCGSPDE-7

Each of the forty putative clones selected from the first round of purification described above was spotted individually onto a lawn of host XL1 cells and incubated overnight at 37°. The plaques were screened with a 370 bp PstI/SmaI restriction endonuclease cleavage fragment of the p3CGS-5 cDNA (corresponding p3CGS-5 nucleotide position numbers 2661–3034). The probe was prepared using the method of Feinberg et al., supra, and the [$^{32}$P]-labeled DNA was purified using Elutip-D® columns. Plaques bound to filter circles were hybridized at 42° overnight in a solution containing 50% formamide, 20 mM Tris-HCl (pH 7.5), 1X Denhardt's solution, 10% dextran sulfate, 0.1% SDS and 106 cpm/ml [$^{32}$P]-labeled probe ($10^9$ cpm/µg). The filters were washed three times for 15 minutes with 2X SSC/0.1% SDS at room temperature, followed by two 15-minute washes with 0.1X SSC/0.1% SDS at 45°. The filters were exposed to x-ray film overnight.

After several rounds of plating and rescreening, six putative clones were purified and sequenced from the ends. The sequence of the five-prime end of the cDNA clone pBBCGSPDE-7 was identical to clone pBBCGSPDE-5, but not the adrenal gland-derived clone, p3CGS-5. The sequence of the three-prime end of the pBBCGSPDE-7 cDNA clone was identical to the p3CGS-5 insert sequence.

Sequence analysis of the pBBCGSPDE-7 insert revealed the DNA sequence set out in SEQ ID NO: 42 and the amino acid sequence of SEQ. ID NO: 43.

The large open reading frame encodes a 942-residue polypeptide that is nearly identical to the adrenal gland cGS-PDE isozyme (921 residues). The difference in the primary structure of these two isozymes lies in the amino-terminal residues 1–46 of the brain cGS-PDE, and residues 1–25 of the adrenal cGS-PDE. The remaining carboxy-terminal residues of the brain and adrenal cGS-PDE are identical.

For transient expression in COS-7 cells, a 3.8 kb fragment of pBBCGSPDE-7 was isolated using HindIII and NotI and inserted into plasmid pCDM8 which had been cut with HindIII and NotI restriction endonucleases. The recombinant pBBCGSPDE-7/CDM8 construct was used to transiently transfect COS-7 cells. The properties of the pBBCGSPDE-7/CDM8 construct and the p3CGS-5/CDM8 construct prepares in Example IV products were subsequently compared. Membrane and supernatant fractions were prepared from extracts of transfected COS-7 cells and assayed for cGS-PDE activity. Both the pBBCGSPDE-7/CDM8 and p3CGS5/CDM8 plasmid constructs produced cGS-PDE activities in COS-7 cell extracts, and most of the activity was detected in the supernatant fractions. However, a 10-fold greater percentage of total cGS-PDE activity was detected in membranes from COS-7 cell extracts transfected with the pBBCGSPDE-7/CDM8 construct than in membranes prepared from p3CGS-5/CDM8-transfected COS-7 cells. These results indicate that, relative to the adrenal cGS-PDE, the isozyme encoded by the pBBCGSPDE-7 cDNA preferentially associates with cellular membranes.

EXAMPLE VI
Use of cGS-PDE Bovine Adrenal cDNA to Obtain Human cGS-PDE cDNAs

Several human cDNA clones, homologous to a cDNA clone encoding the bovine cyclic GMP-stimulated phosphodiesterase, were isolated by hybridization using a nucleic acid probe derived from the bovine cDNA. A combination of sequence analysis and hybridization studies indicates that these human cDNA clones encompass an open reading frame corresponding to a human phosphodiesterase.

cDNA libraries were probed with DNA from plasmid p3CGS-5 which contains a 4.2-kb cDNA insert encoding the bovine CGS-PDE. This plasmid was digested with the restriction enzymes SmaI and EcoRI. The approximately 3.0 kb fragment derived from the cDNA insert was isolated and purified by agarose gel electrophoresis. This fragment contains the entire open reading-frame of the PDE. The fragment was labeled with radioactive nucleotides by random priming.

The cDNA libraries were plated on a 150 mm petri dishes at a density of approximately 50,000 plaques per plate. Duplicate nitrocellulose filter replicas were prepared. The radioactive nucleic acid probe was used for hybridization to the filters overnight at 42° C. in 50% formamide, 5x SSPE (0.9 M NaCl, 0.05 M NaH$_2$PO$_4$H$_2$O, 0.04 M NaOH, and 0.005 M Na$_2$EDTA$_2$H$_2$O), 0.5% SDS, 100 µg/ml salmon testes DNA, and 5x Denhardt's solution. The filters were washed initially at room temperature and subsequently at 65° C. in 2x SSC containing 0.1% SDS. Positive plaques were purified and their inserts were subcloned into an appropriate sequencing vector for DNA sequence analysis by standard techniques.

First, a λgt10 cDNA library prepared from human hippocampus mRNA (clontech, random and dT primed) was screened. Of the approximately 500,000 plaques examined, 33 hybridized to the probe. One of these phages was digested with EcoRI to remove the cDNA insert. This insert-containing EcoRI fragment was cloned into Bluescript KS that had been digested with EcoRI and then treated with calf intestine alkaline phosphatase. One product of this reaction was the plasmid pGSPDE9.2, which showed two major differences when compared to the bovine cGS-PDE cDNA. The 5'0.4 kb of the pGSPDE9.2 insert diverged from the bovine cDNA. Approximately 0.7 kb from the 5' end of the human cDNA there is a 0.7 kb region that diverges from the bovine cDNA. This region may be an intron. Twenty-five of the remaining hippocampus plaques that had hybridized to the bovine probe were examined by PCR, hybridization and/or sequencing. None were found to extend through the regions that differed between the bovine and human cDNAs.

Phages λ GSPDE7.1 and λ GSPDE7.4, two other phages from the hippocampus library, were digested with EcoRI and HindIII. Each yielded a 1.8-kb fragment that contains most of the cDNA insert and approximately 0.2-kb of phage lambda DNA. The λ DNA is present in the fragment because in each case one of the EcoRI sites that typically bracket a cDNA insert had been destroyed, possibly when the library was constructed. The EcoRI/HindIII fragments were cloned into Bluescript KS digested with EcoRI and HindIII. This procedure gave rise to the plasmids pGSPDE7.1 and pGSPDE7.4. The cDNA inserts encode DNA homologous to the 3' portion of the bovine phosphodiesterase cDNA. Both of the cDNA inserts in these clones begin at an EcoRI site and the sequences are homologous adjacent this site.

Portions of pGSPDE7.1 and pGSPDE7.4 cDNA inserts were sequenced and are identical except for a short region of their 3' ends. The cDNA insert in pGSPDE7.1 ends with a sequence of approximately 70 adenine bases, while the cDNA insert in pGSPDE7.4 ends with three additional nucleotides not present in pGSPDE7.1 followed by a sequence of approximately 20 adenine bases.

Next, a cDNA library prepared in λ ZapII (Stratagene) from human heart mRNA yielded one hybridizing plaque from the approximately 500,000 screened. The Bluescript SK(-) plasmid pGSPDE6.1 containing the hybridizing insert was excised in vivo from the λ ZapII clone. Sequence analysis showed that the insert is homologous to the bovine phosphodiesterase cDNA. The homologous region spans the position of the EcoRI found in the sequence formed by joining the sequence of the insert from pGSPDE9.2 to the sequence of the insert in pGSPDE7.1 or pGSPDE7.4. Thus, it is thought that the two clones from the hippocampus form a complete open reading frame.

A third λ gt10 library derived from human placenta mRNA yielded five hybridizing plaques from approximately 800,000 screened. These placental cDNA clones were short and their sequences were identical to portions of the hippocampus cDNA pGSPDE9.2. Screening 5×10⁵ plaques from U118 glioblastoma cDNA library, 5×10⁵ from a spleen cDNA library and 5×10⁵ from an adrenal library (Cushings Disease) gave no hybridization plaques.

Given the homology between the bulk of human and bovine cGS-PDE sequence, it was decided to obtain multiple independent CDNA clones containing the 5' end of the human CGS-PDE to determine if the 0.4 kb 5' sequence was an artifact. An approximately 0.95 kb EcoRI-HindII fragment from the 5' end of the bovine cGS cDNA plasmid p3cgs5 was random primed and used as a probe to screen a number of human cDNA libraries. Hippocampus library screening was carried out under the same screening conditions as described above. All remaining screenings were carried out as described with respect to human heart cDNA library screenings in Example VII, infra. No positives were obtained screening 5×10⁵ plaques from a human T cell library (Hut78, dT-primed), 106 plaques from the hippocampus cDNA library (random and dT-primed), 5×10⁵ plaques from a human liver cDNA library (dT-primed, 5' stretch, Clontech), 5×10⁵ plaques from a human SW1088 glioblastoma cDNA library (dT-primed), 5×10⁵ plaques from the same heart cDNA library (random and dT-primed), and 1.5×10⁶ plaques from a human lung cDNA library (random primed). Two positives were obtained from screening 5×10⁵ plaques from a human fetal brain cDNA library (random and dT-primed, Stratagene). These were designated as HFB9.1 and HFB9.2.

Bluescript SK(-) plasmids pHFB9.2 and pHFB9.1 were excised in vivo from the λZapII clones. DNA sequence analysis revealed that HFB9.1 starts about 80 nucleotides further 3' than does HFB9.2 and reads into an intron approximately 1.9 kb of the way into HFB9.2. HFB9.2 covers the entire open reading frame of the cGS-PDE, but reads into what may be an intron 59 nucleotides after the stop codon. Both of them lack the 5'0.4 kb and the presumed intron found in pGSPDE9.2. The entire open reading frame of HFB9.2 was isolated and assembled into yeast expression vector pBNY6N. The resulting plasmid, designated pHcgs6n, includes the coding region of the cDNA as an EcoRI/XhoI insert. DNA and deduced amino acid sequences for the insert are provided in SEQ.ID No: 44 and 45, respectively.

EXAMPLE VII
Use of CaM-PDE 61 kDa Bovine Brain cDNA to Obtain Human CaM-PDE 61 kDa cDNA Human cDNA clones, λ CaM H6a and λ CaM H3a, which are homologous to the cDNA encoding the bovine 61 kDa CaM-PDE, were obtained by hybridization using a nucleic acid probe derived from the cDNA encoding the bovine species enzyme. A combination of sequence analysis and hybridization studies indicate that λ Cam H6a contains most of an open reading frame encoding a human CaM-PDE.

The hybridization probe used to isolate the human DNA was derived from first strand cDNA of bovine lung tissue by PCR treatment. More specifically, the 23-mer oligonucleotide designated PCR-2S in Example I (see, SEQ ID NO: 1) was combined in a PCR reaction with bovine lung cDNA and a redundant antisense 23-mer oligonucleotide (PCR-5AS) based on the pCAM insert sequence with SEQ ID NO: 46
5'TCRTTNGTNGTNCCYTTCATRTT-3'
representing the amino acid sequence
SEQ ID NO: 47
NMKGTTND,
according to the general procedures of Examples I and III, to generate a 1098 bp cDNA fragment representing a large portion of the coding region of the pCAM-40 insert. The PCR products were purified on a 1% agarose gel using 0.4 M Tris-acetate/0.001 M EDTA buffer containing 0.5 µg/ml ethidium bromide. The DNA products were visualized with UV light, cleanly excised from the gel with a razor blade, purified using Geneclean II reagent kit and ligated into EcoRV-cut pBluescript vector DNA.

To determine if the PCR amplification products were CAM-PDE cDNAs, the subcloned PCR DNA products were sequenced from the ends using T3 and T7 promoter primers and either Sequenase or Taq Polymerase sequencing kits. Approximately 250 bases from each end of this DNA were then compared to the amino acid sequence of bovine CAM-PDE, confirming that the PCR DNA product was a partial CAM PDE cDNA. This clone was designated pCAM-1000 and contained a 1.1-kb insert of nucleic acid that corresponds to nucleotides 409 to 1505 of the insert of pCAM-40. pCaM1000 was digested with the restriction enzymes HinDIII and BamHI. The 1.1-kb fragment was purified by agarose gel electrophoresis and then digested with the restriction enzyme AccI. The two fragments were separated and purified by agarose gel electrophoresis. These separated fragments were labeled with radioactive nucleotides by random priming.

Human cDNA libraries were plated on 150 mm petri dishes at a density of approximately 50,000 plaques per dish and duplicate nitrocellulose filter replicas were prepared. Each probe was hybridized to a separate set of the duplicate filters. The filters were hybridized overnight at 65° C. in 3x SSC, 0.1% sarkosyl, 50 µg/ml salmon testes DNA, 10x Denhardt's solution, 20 mM sodium phosphate (pH 6.8). They were washed at 65° C. in 2x SSC containing 0.1% SDS.

A λ gt10 library prepared from human hippocampus mRNA yielded three hybridizing plaques of the approximately 500,000 screened. Of these three hybridizing plaques, two hybridized to both probes and the third hybridized to the longer of the two probes. The λ Cam H6a clone contains an approximately 2 kb insert that is homologous to the cDNA encoding the bovine clone of pCAM-40.

The λ cam H6a cDNA was subcloned into the plasmid Bluescript KS for sequence analysis. Although the cDNA library had been constructed with EcoRI linkers, one of the EcoRI sites that should have flanked the cDNA insert did not cut with EcoRI. Thus, the cDNA was subcloned as two fragments: an approximately 0.7 kb EcoRI/HindIII fragment (pcamH6C) and an approximately 1.6 kb HindIII fragment that contained approximately 1.3 kb of cDNA and 0.25 kb of flanking λgt10 vector DNA (pcamH6B). DNA sequence analysis revealed that it encoded most of a human CaM-PDE homologous to the bovine 61 k CaM-PDE, except that the human cDNA appeared to be missing two base pairs in the middle of the coding region. These missing nucleotides correspond to positions 626 and 627 of the human cDNA sequence if it is aligned with the pCAM-40 bovine 61 kDa CaM-PDE (SEQ. ID NO: 5 for maximum homology.

Another of the cDNA clones from the hippocampus cDNA library that had been screened with the bovine 61 kDa CaM-PDE probes was λcamH2a. It contained an approximately 1.0 kb insert. As was the case for λcamH6a cDNA, only one of the two EcoRI sites that should be present at the ends of the insert would cut. The original subcloning and DNA sequence analysis for this cDNA utilized PCR fragments generated with oligos in the flanking λgt10 vector arms. This cDNA overlaps much of the 5' end of the insert in λcamH6a and contained the additional two-nucleotides predicted by the bovine sequence and required to maintain the PDE open reading frame. The λcamH2a insert also appeared to contain two introns; one 5' of the initiator methionine and one downstream of the HindIII site. The EcoRI/HindIII fragment from λcamH2a (corresponding to the region covered by pcamH6C) was subcloned into the plasmid Bluescript SK⁻ and designated pcamH2A-16. This was then used as the source of the two additional bp in the construction of yeast expression plasmids described below.

Two different plasmids were constructed for human CaM-PDE expression in yeast. One plasmid, pHcam61-6N-7, contains the entire open reading frame. The second plasmid, pHcam61met140, starts at an internal methionine (beginning at nucleotide position 505) and extends to the end of the open reading frame. These expression plasmids were constructed by modifying the 3' portion of the open reading frame and then adding the two differently modified 5' ends to the 3' end. The sequence of the cDNA insert of pHcam61-6N-7 is set out in SEQ. ID NO: 48 and the deduced amino acid sequence of the CaM-PDE encoded thereby is set out in SEQ. ID NO: 49. During construction of the cDNA insert, the nucleotide at position 826 was altered from T to C, but the encoded amino acid was conserved. Plasmid pHcam61met140, as noted above, has a cDNA insert lacking the first 140 codons of the coding region of the pHcam61-6N-7 but is otherwise identical thereto.

A third cDNA, λcamH3a, contained an approximately 2.7 kb insert. This cDNA insert was subcloned for sequence analysis. Although the cDNA library had been constructed with EcoRI, the inserted cDNA in λcamH3a could not be excised with EcoRI. Presumably one of the EcoRI sites was destroyed during the construction of the library. The cDNA insert was excised from the λ clone by digestion with HindIII and EcoRI. This digestion yields two relevant fragments, a 0.6 kb HindIII fragment which contains a portion of DNA from the left arm of λgt10 attached to the cDNA insert and an approximately 2.4 kb HindIII/EcoRI fragment containing the remainder of the cDNA insert. These two fragments were assembled in the plasmid Bluescript KS to yield an approximately 3 kb fragment. The orientation of the small HindIII fragment was the same as the original λ clone. This subclone is known as pcamH3EF. Although this cDNA hybridizes to the bovine probe from the bovine CaM-PDE 61 kDa cDNA, sequence analysis revealed that it appeared to be the product of a different CaM-PDE gene. Plasmid pcamH3EF contains what may be the entire open reading frame and would encode a protein approximately 75% homologous to the protein encoded by the insert of pHcam61-6N-7 over much of its lengths. DNA and deduced amino acid sequences are set out in SEQ. ID NOS: 50 and 51, respectively. The DNA sequence of the region between nucleotide 80 and 100 of pcamH3EF is uncertain. This area is 5' to the initiator methionine codon and thus does not effect the open reading frame.

An approximately 2.4 kb fragment of pcamH3EF was gel purified following digestion with the restriction enzymes HindIII and EcoRI. This fragment was used to screen additional human cDNA libraries in a similar manner to the screen described above. Screening approximately 5×10⁵ plaques from a human heart cDNA library (Stratagene) yielded two plaques that hybridized to the pcamH3EF probe. The Bluescript SK⁻ plasmid pcamHella was excised in vivo from one of these positive λZapII clones. DNA and deduced amino acid sequences for the cDNA insert are set out in SEQ. ID NO: 52 and 53, respectively. Sequence analysis of pcamHella showed that the insert began at nucleotide position 610 of pcamH3EF and was nearly identical through nucleotide position 2066, at which point the DNA sequence diverged from that of pcamH3EF. The cDNA insert of pcamHella continued for approximately 0.6 kb. The consequence of this divergence is to alter the carboxy terminus of the protein that would be encoded by the open reading frame within the cDNA. The pcamH3EF cDNA could encode a protein of 634 amino acids (MW72,207). Assuming the 5' end of the pcamHella cDNA is the same as that of the 5' end of pcamH3EF (5' to nucleotide position 610), pcamHella could encode a 709 amino acid protein (MW80,759). These divergent 3' ends may be the consequence of alternative splicing, lack of splicing, or unrelated DNA sequences being juxtaposed during the cloning process.

EXAMPLE VIII

Expression of Bovine and Human PDE cDNAs for Complementation of Yeast Phenotypic Defects The present example relates to the expression of bovine and PDE clones in yeast demonstrating the capacity of functional PDE expression products to suppress the heat shock phenotype associated with mutation of yeast phosohodiesterase genes and also relates to the biochemical assay of expression products. The host cells used in these procedures were S. cerevisiae yeast strains 10DAB (ATCC accession No. 74049) and YKS45, both of which were pd¹⁻ pde²⁻ resulting in a phenotype characterized by heat shock sensitivity, i.e., the inability of cells to survive exposure to elevated temperatures on the order of 55–56° C. In these complementation procedures, the inserted gene product was noted to conspicuously modify the heat shock phenotype. This capacity, in turn, demonstrates the feasibility of systems designed to assay chemical compounds for their ability to modify (and especially the ability to inhibit) the in vivo enzymatic activity of mammalian Ca²⁺/calmodulin stimulated and cGMP stimulated cyclic nucleotide phosphodiesterases.

A. Yeast Phenotype Complementation by Expression of a cDNA Encoding CaM-PDE

A 2.2 kb cDNA fragment, adapted for insertion into yeast expression plasmids pADNS (ATCC accession No. 68588) and pADANS (ATCC accession No. 68587) was derived from plasmid pCAM-40 (Example I) by polymerase chain reaction. Briefly, the following PCR amplification was employed to alter the pCAM-40 DNA insert to align it appropriately with the ADH1 promoter in the vectors.

One oligonucleotide primer (Oligo A) used in the PCR reaction

SEQ ID NO: 54

5'-TACGAAGCTTTGATGGGGTCTACTGCTAC-3' anneals to the pCaM-40 cDNA clone at base pair positions 100–116 and includes a HindIII site before the initial methionine codon. A second oligonucleotide primer (Oligo B)

SEQ ID NO: 55

5'-TACGAAGCTTTGATGGTTGGCTTGGCATATC-3' was designed to anneal at positions 520–538 and also includes a HindIII site two bases before a methionine codon. The third oligonucleotide

SEQ ID NO: 56

5'-ATTACCCCTCATAAAG-3' annealed to a position in the plasmid that was 3' of the insert. For one reaction, Oligo A and Oligo C were used as primers with pCAM-40 as the template. The nucleic acid product of this reaction included the entire open reading frame. A second reaction used Oligo B and Oligo C as primers on the template pCAM-40 and yielded a nucleic acid product that lacked the portion of the cDNA sequence encoding the calmodulin binding domain. These amplified products were digested with HindIII and NotI and ligated to HindIII/NotI-digested yeast expression vectors pADNS and pADANS. Plasmid clones containing inserts were selected and transformed into S. cerevisiae strain 10DAB by lithium acetate transformation.

Transformed yeast were streaked in patches on agar plates containing synthetic medium lacking the amino acid leucine (SC-leucine agar) and grown for 3 days at 30° C. Replicas of this agar plate were made with three types of agar plates: one replica on SC-leucine agar, one replica on room temperature YPD agar, and three replicas on YPD agar plates that had been warmed to 56° C. The three warmed plates were maintained at 56° C. for 10, 20, or 30 minutes. These replicas were than allowed to cool to room temperature and then all of the plates were placed at 30° C. Yeast transformed with plasmids constructed to express the CaM-PDE were resistant to the thermal pulse. More specifically, both the construct designed to express the complete open reading frame and that designed to express the truncated protein (including the catalytic region but not the calmodulin binding domain), in either pADNS or pADANS, complemented the heat shock sensitivity phenotype of the 10DAB host cells, i.e., rendered them resistant to the 56° C. temperature pulse.

In a like manner, plasmids pHcam61-6N-7 and pHcam61met140 (Example VII) were transformed into yeast host 10DAB. Heat shock phenotypes were suppressed in both transformants.

B. Biochemical Assay of Expression Products

The bovine CaM-PDE expression product was also evaluated by preparing cell-free extracts from the 10DAB yeast cells and measuring the extracts' biochemical phosphodiesterase activity. For this purpose, 200 ml cultures of transformed yeast were grown in liquid SC-leucine to a density of about 6 million cells per ml. The cells were collected by centrifugation and the cell pellets were frozen. Extracts were prepared by thawing the frozen cells on ice, mixing the cells with 1 ml of PBS and an equal volume of glass beads, vortexing them to disrupt the yeast cells, and centrifuging the disrupted cells at approximately 12,000×g for 5 min to remove insoluble debris. The supernatant was assayed for phosphodiesterase activity.

Extracts of yeast cells, up to 50 $\mu$l, were assayed for phosphodiesterase activity in 50 mM Tris (pH 8.0), 1.0 mM EGTA, 0.01 mg/mL BSA (bovine serum albumin), [$^3$H]-cyclic nucleotide (4–10,000 cpm/pmol), and 5 mM $MgCl_2$ in a final volume of 250 $\mu$l at 30° C. in 10×75 mm glass test tubes. The incubations were terminated by adding 250 $\mu$l of 0.5 M sodium carbonate pH 9.3, 1M NaCl, and 0.1% SDS. The products of the phosphodiesterase reaction were separated from the cyclic nucleotide by chromatography on 8×33 mm columns of BioRad Affi-Gel 601 boronic acid gel. The columns were equilibrated with 0.25M sodium bicarbonate (pH 9.3) and 0.5 M NaCl. The reactions were applied to the columns. The assay tubes were rinsed with 0.25M sodium bicarbonate (pH 9.3) and 0.5 M NaCl and this rinse was applied to the columns. The boronate columns were washed twice with 3.75 ml of 0.25 M sodium bicarbonate (pH 9.3) and 0.5 M NaCl followed by 0.5 ml of 50 mM sodium acetate (pH 4.5). The product was eluted with 2.5 ml of 50 mM sodium acetate (pH 4.5) containing 0.1 M sorbitol and collected in scintillation vials. The eluate was mixed with 4.5 ml Ecolite Scintillation Cocktail and the radioactivity measured by liquid scintillation spectrometry.

Both the construct designed to express the complete bovine open reading frame and that designed to express a truncated protein, in either pADNS or pADANS, expressed active protein as determined by biochemical phosphodiesterase assay of cell extracts. Extracts of 10DAB harboring pcam61met140 yielded measurable phorphodiesterase activity (see, infra, second method of part D) while the extract of 10DAB cells harboring pcamH61-6N-7 lacked detectable activity.

C. Yeast Phenotype Complementation by Expression of a cDNA Encoding a cGS-PDE The plasmid p3CGS-5, which contains a 4.2-kb DNA fragment encoding the bovine cGS-PDE, was adapted for cloning into PADNS and pADANS by replacing the first 147 bases of the cDNA with a restriction site suitable for use in insertion into plasmids. The oligonucleotide BS1, having the sequence SEQ ID NO: 57
5'TACGAAGCTTTGATGCGCCGACAGCCTGC,
encodes a HindIII site and anneals to positions 148–165 of the cDNA insert. An oligonucleotide designated BS3

SEQ ID NO: 58
GGTCTCCTGTTGCAGATATTG,
anneals to positions 835–855 just 3' of a unique NsiI site. The resulting PCR-generated fragment following digestion with HindIII and NsiI was then ligated to HindIII- and NsiI-digested p3CGS-5 thereby replacing the original 5' end of the bovine cDNA. A plasmid derived from this ligation was digested with HindIII and NotI to release the modified cDNA insert. The insert was cloned into pADNS and pADANS at their HindIII and NotI sites. These plasmids were then transformed into the yeast strain 10DAB by the lithium acetate method and the transformed cells were grown and subjected to elevated temperatures as in Section A, above. Yeast transformed with plasmids constructed to express the bovine cGS-PDE were resistant to the thermal pulse.

In a like manner, plasmid pHcgs6n (Example VI) was transformed into yeast host strain YKS45 by lithium acetate transformation. Heat shock analysis was performed as above except that the plates were initially grown two days at 30° C. and the warmed plates were maintained at 56° C. for 10, 20, 30 and 45 minutes. Yeast transformed with the plasmid designed to express the full length human cGS-PDE was resistant to thermal pulse.

D. Biochemical Assay of Expression Product

The expression of the bovine cGS-PDE was also evaluated by preparing cell-free extracts from the yeast and measuring the extracts' biochemical phosphodiesterase activity. For this purpose, 50 ml cultures of transformed 10DAB yeast cells were grown in liquid SC-leucine to a density of about 10 million cells per ml. Sherman et al., Methods in Yeast Genetics, Cold Spring Harbor Laboratory, Cold Spring Harbor, N.Y. (1986). The cells were collected by centrifugation, the cell pellets were washed once with water, and the final cell pellets were frozen. To prepare an extract, the frozen cells were thawed on ice, mixed with 1 ml of PBS and an equal volume of glass beads, vortexed to disrupt the yeast cells, and centrifuged to remove debris. The supernatant was then assayed for phosphodiesterase activity as in Section B, above. Constructs in either pADNS or pADANS expressed active protein as determined by biochemical phosphodiesterase assay of cell extracts.

YKS45 transformed with plasmid pHcgs6n were grown in SC-leu medium to 1–2×10$^7$ cells/ml. The cells were harvested by centrifugation and the cell pellets were frozen. A frozen cell pellet, typically containing 10$^{10}$ cells, was mixed with lysis buffer (25 mM Tris HCl pH 8, 5 mM EDTA, 5 mM EGTA, 1 mM o-phenathroline, 0.5 mM AEBSF, 0.01 mg/mL pepstatin, 0.01 mg/mL leupeptin, 0.01 mg/mL aprotinin, 0.1% 2-mercaptoethanol) to bring the total volume to 2.5 ml. The mixture was thawed on ice and then added to an equal volume of glass beads. The cells were disrupted by cycles of vortexing and chilling on ice, then additional lysis buffer was mixed with the disrupted cells to bring the total lysis buffer added to 5 ml. The suspension was centrifuged for 5 min. at 12,000 xg. The supernatant was removed and either assayed immediately or frozen rapidly in a dry ice ethanol bath and stored at −70° C.

Phosphodiesterase activity was assayed by mixing an aliquot of cell extract in (40 mM Tris-Cl pH 8.0, 1 mM EGTA, 0.1 mg/mL BSA) containing 5 mM MgCl$_2$ and radioactive substrate, incubating at 30° C. for up to 30 min. and terminating the reaction with stop buffer (0.1M ethanolamine pH 9.0, 0.5M ammonium sulfate, 10 mM EDTA, 0.05% SDS final concentration). The product was separated from the cyclic nucleotide substrate by chromatography on BioRad Affi-Gel 601. The sample was applied to a column containing approximately 0.25 ml of Affi-Gel 601 equilibrated in column buffer (0.1M ethanolamine pH 9.0 containing 0.5M ammonium sulfate). The column was washed five times with 0.5 ml of column buffer. The product was eluted with four 0.5 ml aliquots of 0.25M acetic acid and mixed with 5 ml Ecolume (ICN Biochemicals). The radioactive product was measured by scintillation counting. Extracts from yeast expressing the human cGS-PDE hydrolyzed both cyclic AMP and cyclic GMP, as expected for this isozyme.

EXAMPLE IX

Tissue Expression Studies Involving CaM-PDE and cGS-PDE Polynucleotides

A. Northern Blot Analysis

DNAs isolated in Examples I, III, and IV above were employed to develop probes for screening total or poly A-selected RNAs isolated from a variety of tissues and the results are summarized below.

1. Northern analysis was performed on mRNA prepared from a variety of bovine adrenal cortex, adrenal medulla, heart, aorta, cerebral cortex, basal ganglia, hippocampus, cerebellum, medulla/spinal cord, liver, kidney cortex, kidney medulla, kidney papillae, trachea, lung, spleen and T-lymphocyte tissues using an approximately 3 kb radiolabeled cDNA fragment isolated from plasmid p3CGS-5 upon digestion with EcoRI and SmaI. A single 4.5 kb mRNA species was detected in most tissues. The size of the cGS-PDE mRNA appeared to be slightly larger (approximately 4.6 kb) in RNA isolated from cerebral cortex, basal ganglia and hippocampus. The cGS PDE mRNA was most abundant in adrenal cortex. It was also abundant in adrenal medulla and heart. It appeared to be differentially expressed in anatomically distinct regions of the brain and kidney. Among RNAs isolated from five different brain regions, cGS PDE mRNA was most abundant in hippocampus, cerebral cortex, and basal ganglia. Very little cGS PDE transcript was detected in cerebellum or medulla and spinal cord RNAs. Although the cGS PDE mRNA was detected in all regions of the kidney, it appeared to be most abundant in the outer red medulla and papillae. The cGS PDE mRNA was also detected in liver, trachea, lung, spleen, and T-lymphocyte RNA. Very little cGS PDE mRNA was detected in RNA isolated from aorta.

2. Radiolabeled DNA probes were prepared from random hexamer primed fragments extended on heat denatured 1.6 kb EcoRI restriction endonuclease fragments of the cDNA insert of plasmid pCAM-40. In Northern analysis, the DNA probes hybridized with 3.8 and 4.4 kb mRNAs in brain and most of the other tissues analyzed including cerebral cortex, basal ganglia, hippocampus, cerebellum, medulla and spinal cord, heart, aorta, kidney medulla, kidney papillae, and lung. Hybridization of probe with the 3.8 kb mRNA from liver, kidney cortex and trachea was only detected after longer autoradiographic exposure.

3. Northern blot analysis of mRNA from several tissues of the central nervous system was carried out using a subcloned, labeled p12.3a DNA fragment (containing most of the conserved PDE catalytic domain) as a probe. The most intense hybridization signal was seen in mRNA from the basal ganglia and strong signals were also seen in mRNA from other tissues including kidney papilla and adrenal medulla.

B. RNAse Protection

1. Three antisense riboprobes were constructed. Probe III corresponds to the catalytic domain-encoding region of p3cGS-5 (273 bp corresponding to bases 2393 through 2666 of SEQ. ID NO: 38); probe II to the cGMP-binding domain encoding (468 bp corresponding to bases 959 through 1426; and probe I to the 5' end and portions of amino terminal-encoding region (457 bases corresponding to bases 1 through 457).

Total RNAs extracted from all of the examined tissues completely protected probes II and III. Nearly complete protection (457 bases) of riboprobe I with RNAs isolated from adrenal cortex, adrenal medulla, and liver was also observed. However, RNA isolated from cerebral cortex, basal ganglia, and hippocampus only protected an approximately 268-base fragment of riboprobe I. A relatively small amount of partially protected probe I identical in size with the major fragments observed in the brain RNA samples was also detected in RNAs isolated from all of the examined tissues except liver. Interestingly, heart RNA yielded both completely protected (457 base) riboprobe and, like brain RNA, a 268-base fragment. Unlike the protection pattern observed using RNAs isolated from any of the other tissues, however, the partially protected riboprobe I fragment appeared to be more abundant. The results suggest that two different cGS-PDE RNA species are expressed.

2. Radiolabeled antisense riboprobes corresponding to a portion of either the CaM-binding domain on the catalytic domain of CaM-PDE were constructed from restriction endonuclease cleavage fragments (AccI/SstI and Tth111I/HincII) of pCAM-40cDNA. Total RNAs isolated from five different brain regions (cerebral cortex, basal ganglia, hippocampus, cerebellum, and medulla/spinal cord) completely protected the antisense riboprobes encoding both the CaM-binding and catalytic domains. Total RNAs from heart, aorta, lung, trachea and kidney completely protected the riboprobe corresponding to the catalytic domain but only protected about 150 bases of the CaM-binding domain riboprobe, suggesting that an isoform structurally related to the 61 kD CaM-PDE is expressed in these tissues.

3. Antisense riboprobes were generated based on plasmid p12.3a and corresponding to bases -1 through 363 and 883–1278 of SEQ. ID NO: 26. The former probe included 113 bases of the 5' noncoding sequence as well as the start methionine codon through the putative CaM-binding domain, while the latter encoded the catalytic domain. Among all tissues assayed, RNA from basal ganglia most strongly protected each probe. Strong signals of a size corresponding to the probe representing the amino terminus were observed in protection by cerebral cortex, cerebellum, basal ganglia, hippocampus and adrenal medulla RNA. No protection was afforded to this probe by kidney papilla or testis RNA even though the tissue showed signals on the Northern analysis and RNAse protection of the conserved domain probe, suggesting that a structurally related isozyme is expressed in this tissue.

While the present invention has been described in terms of specific methods and compositions, it is understood that variations and modifications will occur to those skilled in the art upon consideration of the invention. Consequently only such limitations as appear in the appended claims should be placed thereon. Accordingly, it is intended in the appended claims to cover all such equivalent variations which come within the scope of the invention as claimed.

What is claimed is:

1. An assay method for identifying a chemical agent which modifies the enzymatic activity of a mammalian cyclic GMP stimulated nucleotide phosphodiesterase said method comprising:
   (a) stably transforming with a polynucleotide encoding a mammalian cyclic GMP stimulated nucleotide phosphodiesterase selected from the group consisting of:
      (i) a polynucleotide encoding the amino acid sequence of SEQ ID NO: 39;
      (ii) a polynucleotide encoding the amino acid sequence of SEQ ID NO: 43;
      (iii) a polynucleotide encoding the amino acid sequence of SEQ ID NO: 45;
      (iv) a polynucleotide which hybridizes under stringent hybridization conditions to an antisense strand of the DNA insert in vector p3CGS-5 (A.T.C.C. 68579), pHcgs6n (A.T.C.C. 68962), pGSPDE6.1 (A.T.C.C. 68583), pGSPDE7.1 (A.T.C.C. 68585), or pBBCGSPDE-5 (A.T.C.C. 68578); and
      (v) a polynucleotide encoding the same polypeptide as (iv) by means of degenerate codons;
   a eukaryotic host cell having a heat-shock sensitivity phenotypic character susceptible to alteration, such that upon expression of said polynucleotide sequence said cell exhibits an altered heat-shock phenotype;
   (b) growing the transformed host cell formed in step (a) in a nutrient medium under conditions allowing expression of said polynucleotide sequence in said transformed host cell accompanied by the corresponding alteration in the transformed host cell phenotype;
   (c) contacting the transformed host cells grown according to step (b) with a chemical agent to be assayed; and
   (d) determining if the chemical agent step (c) modifies the enzymatic activity of the enzyme of step (a) by determining if the altered heat-shock phenotype of the cells of step (c) has been modified.

2. An assay method according to claim 1 wherein the host cell is a yeast host cell.

3. An assay method for identifying a chemical agent which modifies the enzymatic activity of a mammalian cyclic GMP stimulated nucleotide phosphodiesterase said method comprising:
   (a) stably transforming with a polynucleotide encoding a mammalian cyclic GMP stimulated nucleotide phosphodiesterase selected from the group consisting of:
      (i) a polynucleotide encoding the amino acid sequence of SEQ ID NO: 39;
      (ii) a polynucleotide encoding the amino acid sequence of SEQ ID NO: 43;
      (iii) a polynucleotide encoding the amino acid sequence of SEQ ID NO: 45;
      (iv) a polynucleotide which hybridizes under stringent hybridization conditions to an antisense strand of the DNA insert in vector p3CGS-5 (A.T.C.C. 68579), pHcgs6n (A.T.C.C. 68962), pGSPDE6.1 (A.T.C.C. 68583), pGSPDE7.1 (A.T.C.C. 68585), or pBBCGSPDE-5 (A.T.C.C. 68578); and
      (v) a polynucleotide encoding the same polypeptide as (iv) by means of degenerate codons;
   a eukaryotic host cell having a heat-shock sensitivity phenotypic character susceptible to alteration, such that upon expression of said polynucleotide sequence said cell exhibits an altered heat-shock phenotype;

(b) growing the transformed host cell formed in step (a) in a nutrient medium under conditions allowing expression of said polynucleotide sequence in said transformed host cell accompanied by the corresponding alteration in the host cell phenotype;

(c) identifying said transformed host cells having an altered heat-shock phenotype;

(d) disrupting said transformed host cells;

(e) isolating cytosol from said disrupted transformed host cells;

(f) contacting said cytosol with said chemical agent; and (g) determining whether said enzymatic activity has been altered.

4. An assay method according to claim 3 wherein the host cell is a yeast host cell.

* * * * *

UNITED STATES PATENT AND TRADEMARK OFFICE
CERTIFICATE OF CORRECTION

PATENT NO. : 6,015,677
DATED : January 18, 2000
INVENTOR(S) : Beavo et al.

It is certified that error appears in the above-identified patent and that said Letters Patent is hereby corrected as shown below:

Title page,
Item [75] Inventors, replace "Kelley J. Bentley", with -- J. Kelley Bentley --.

OTHER PUBLICATIONS, under Beavo, J.A., replace "Sond" with -- Sons --.
Under Epstein, P.M. *et al.*, replace "Ca2+" with -- $Ca^{2+}$ --.

Column 1,
Line 40, replace "througnout" with -- throughout --.

Column 2,
Line 2, replace "CGMP" with -- cGMP --.
Line 7, replace "cells-" with -- cells --.

Column 3,
Line 61, replace "isolate-" with -- isolate --.
Line 65, replace "of-phosphodiesterases" with -- of phosphodiesterases --.

Column 4,
Line 10, replace "Ovchinnikow" with -- Ovchinnikov --.
Line 28, replace "phospho-diesterase" with -- phosphodiesterase --.
Line 64, replace "DNA-sequences" with -- DNA sequences --.

Column 5,
Line 43, "13. Plasmid" should begin a new paragraph.
Line 47, replace "CDNA" with -- cDNA --.

Column 6,
Line 10, replace "products." with -- products --.
Line 40, replace "MRNA" with -- mRNA --.

Column 7,
Line 63, replace "RNAS" with -- RNAs --.

Column 8,
Line 12, in Table I, replace "G or T Keto" with -- K G or T Keto --.

Column 9,
Line 33, replace "CDNA" with -- cDNA --.

UNITED STATES PATENT AND TRADEMARK OFFICE
CERTIFICATE OF CORRECTION

PATENT NO. : 6,015,677
DATED : January 18, 2000
INVENTOR(S) : Beavo et al.

It is certified that error appears in the above-identified patent and that said Letters Patent is hereby corrected as shown below:

Column 10,
Line 18, replace "M1" with -- µl --.
Line 58, replace "CAMP" with -- cAMP --.

Column 11,
Line 52, replace "CDNA" with -- cDNA --.

Column 12,
Line 2, replace "MRNA" with -- mRNA --.

Column 13,
Line 13, replace "5'$^{32}$p_labelled" with -- 5'$^{32}$P-labelled --.
Lines 43 and 47, replace "CDNA" with -- cDNA --.

Column 15,
Line 26, replace "µ-mercaptoethanol" with -- β-mercaptoethanol --.
Line 45, replace "MRNA" with -- mRNA --.
Line 50, replace "triphos hates" with -- triphosphates --.
Line 59, replace "a" with -- an --.

Column 16,
Line 29, replace "CDNA" with -- cDNA --.

Column 17,
Line 59, replace "107" with -- $10^7$ --.

Column 18,
Line 23, replace "p3CGS-5pCDM8" with -- p3CGS-5/pCDM8 --.

Column 19,
Line 11, replace "106" with -- $10^6$ --.
Line 41, replace "prepares" with -- prepared --.

Column 21,
Line 15, replace "CDNA" with -- cDNA --.
Line 26, replace "106" with -- $10^6$ --.

UNITED STATES PATENT AND TRADEMARK OFFICE
CERTIFICATE OF CORRECTION

PATENT NO. : 6,015,677
DATED : January 18, 2000
INVENTOR(S) : Beavo et al.

It is certified that error appears in the above-identified patent and that said Letters Patent is hereby corrected as shown below:

Column 23,
Line 6, replace "two-nucleotides" with -- two nucleotides --.
Line 60, replace "effect" with -- affect --.

Column 24,
Line 31, replace "pd$^{1-}$" with -- pde$^{1-}$ --.

Column 26,
Line 12, replace "phorphodiesterase" with -- phosphodiesterase --.
Line 22, replace "PADNS" with -- pADNS --.

Signed and Sealed this

Twenty-sixth Day of February, 2002

Attest:

JAMES E. ROGAN
Attesting Officer
Director of the United States Patent and Trademark Office